(12) United States Patent
Guo et al.

(10) Patent No.: US 11,545,640 B2
(45) Date of Patent: Jan. 3, 2023

(54) PHOTOISOMERIC COMPOUNDS AND DEVICE COMPRISING THE SAME

(71) Applicant: PEKING UNIVERSITY, Beijing (CN)

(72) Inventors: Xuefeng Guo, Beijing (CN); Chuancheng Jia, Beijing (CN); Na Xin, Beijing (CN); Hongliang Chen, Beijing (CN); Mingliang Li, Beijing (CN); Dahui Qu, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 17/160,174

(22) Filed: Jan. 27, 2021

(65) Prior Publication Data

US 2021/0234109 A1 Jul. 29, 2021

Related U.S. Application Data

(62) Division of application No. 16/303,597, filed as application No. PCT/CN2017/085720 on May 24, 2017, now abandoned.

(30) Foreign Application Priority Data

May 24, 2016 (CN) .......................... 201610346549.5
Jun. 1, 2016 (CN) .......................... 201610383815.1

(51) Int. Cl.
*H01L 51/00* (2006.01)
*H01L 51/05* (2006.01)
(Continued)

(52) U.S. Cl.
CPC ........ *H01L 51/0098* (2013.01); *C07D 333/16* (2013.01); *C07F 15/0046* (2013.01);
(Continued)

(58) Field of Classification Search
CPC . H01L 51/00; H01L 51/0068; H01L 51/0071; H01L 51/0072; H01L 51/0074;
(Continued)

(56) References Cited

U.S. PATENT DOCUMENTS 7,101,497 B2   9/2006  Tanaka et al.
7,355,775 B2 * 4/2008  Yam .................... C07D 471/04
                                                     546/88

(Continued)

FOREIGN PATENT DOCUMENTS

CA         2635037         10/2008
WO    WO 2014/035224      3/2014

OTHER PUBLICATIONS

Akazawa et al. ("Photoresponsive dithienylethene-urea-based organogels with 'reversed' behavior," Org. Biomol. Chem., 2008, 6, 1544-1547) (Year: 2008).*

(Continued)

*Primary Examiner* — Matthew R Diaz
(74) *Attorney, Agent, or Firm* — Norton Rose Fulbright US LLP

(57) ABSTRACT

Disclosed are a series of photoisomeric compounds, preparation method therefor and device comprising the compounds, wherein a photoisomeric compound-graphene molecular junction device is formed by linking the photoisomeric compound to a gap of two-dimensional monolayer graphene having a nano-gap array via an amide covalent bond. When a single photoisomeric compound is bridged to the gap of the two-dimensional monolayer graphene having a nano-gap array, the devices have a reversible light-controlled switching function and a reversible electrically-controlled switching function. A molecular switch device prepared by the method can achieve a high reversibility and a good reproducibility. The number of light-controlled switching cycles can exceed $10^4$, and the number of elec- (Continued)

trically-controlled switching cycles can reach about $10^5$ or greater. Moreover, the above-mentioned reversible molecular switch device remains stable within a period of more than one year. In addition, flexible non-losable organic memory transistor devices and light-responsive organic transistor devices can be constructed using the above-mentioned series of photoisomeric compounds.

8 Claims, 5 Drawing Sheets

(51) Int. Cl.
    *C07D 333/16*     (2006.01)
    *C07F 15/00*     (2006.01)

(52) U.S. Cl.
    CPC ...... *H01L 51/0068* (2013.01); *H01L 51/0086* (2013.01); *H01L 51/0595* (2013.01)

(58) Field of Classification Search
    CPC ............. H01L 51/0083; H01L 51/0084; H01L 51/0085; H01L 51/0086; H01L 51/0087; H01L 51/0088; H01L 51/0089; H01L 51/0098; H01L 51/0512; H01L 51/0595; C07D 333/16; C07F 15/0046; H01B 1/12; H01B 1/121; H01B 1/122; H01B 1/124; H01B 1/125; H01B 1/127; H01B 1/128
    See application file for complete search history.

(56) References Cited

U.S. PATENT DOCUMENTS

| | | | | |
|---|---|---|---|---|
| 7,777,055 | B2 * | 8/2010 | Branda | C08G 61/02 549/49 |
| 8,441,707 | B2 | 5/2013 | Lam et al. | |
| 9,227,986 | B2 * | 1/2016 | Branda | G02F 1/0126 252/500 |
| 2003/0118924 | A1 | 6/2003 | Kim et al. | |
| 2014/0000696 | A1 * | 1/2014 | Wong et al. | C07D 519/00 |
| 2015/0070743 | A1 * | 3/2015 | Branda et al. | H01L 51/0086 977/948 |

OTHER PUBLICATIONS

Li et al. ("New light on the ring-chain equilibrium of a hydrogen-bonded supramolecular polymer based on a photochromic dithienylene unit and its energy-transfer properties as a storage material," Chem. Eur. J., 2011, 17, 10716-10723) (Year: 2011).*

Motta et al. ("Conductance of a photochromic molecular switch with graphene leads," Physical Review B, 2011, 84, 113408) (Year: 2011).*

Meng et al. ("Photo-modulable molecular transport junctions based on organometallic molecular wires," Chem. Sci., 2012, 3, 3113-3118) (Year: 2012).*

Jia et al. ("Conductance switching and mechanisms in single-molecule junctions," Angew. Chem. Int. Ed., 2013, 52, 8666-8670) (Year: 2013).*

Liu et al. ("Diarylethene-containing carbon-rich ruthenium organometallics: tuning of electrochromism," Inorg. Chem., 2014, 53, 8172-8188) (Year: 2014).*

Cao et al., "Building High-Throughput Molecular Junctions Using Indented Graphene Point Contacts," *Angew. Chem. Int. Ed.,* 2012, 51:12228-12232.

Chen et al., "Design of a Photoactive Hybrid Bilayer Dialectric for Flexible Nonvolatile Organic Memory Transistors," *ACS Nano,* 2016, 10(1):436-445. (Abstract Only).

Chen et al., "Self-assembly of cationic pyrene nanotubes," *J. Mater. Chem.,* 2012, 22:4927-4931. (Abstract Only).

Davis et al., "Force-induced activation of covalent bonds in mechanoresponsive polymeric materials," *Nature,* 2009, 459(7243):68-72. (Abstract Only).

International Search Report and Written Opinion issued in International Patent Application No. PCT/CN2017/085720, dated Aug. 10, 2017.

Jia & Guo, "Conductance switching and Mechanisms in Single-Molecule Junctions," The twenty-ninth annual academic meeting of China Chemical Society, Center for Nanochemistry, College of Chemistry and Molecular Engineering, 2013. (Abstract Only).

Jia et al., "Covalently bonded single-molecule junctions with stable and reversible photoswitched conductivity," *Science,* 2016, 352:1443.

Li et al., "New Light on the Ring-Chain Equilibrium of a Hydrogen-Bonded Supramolecular Polymer Based on a Photochromic Dithienylethene Unit and its Energy-Transfer Properties as a Storage Material," *Chem. Eur. J.,* 2011, 17:10716-10723.

Liu et al., "Diarylethene-containing carbon-rich ruthenium organometallics: tuning of electrochromism," *Inorg Chem.,* 2014, 53(15):8172-8188. (Abstract Only).

Lucas et al., "A new class of photochromic 1,2-diarylethenes; synthesis and switching properties of bis(3-thienyl)cyclopentenes," *Chem. Commun.,* 1998, 2313-2314.

Meng et al., "Orthogonally modulate molecular transport junctions for resettable electronic logic gates," *Nature Communications,* 2014, 5:3023.

Meng et al., "Photo-modulable Molecular Transport Junctions based on Organometallic Molecular Wires," *The Royal Society of Chemistry,* 2012, 3(10):3113-3118.

Office Action issued in corresponding Japanese application No. 2018-561551, dated Jan. 7, 2020 (English translation provided).

Search Report issued in Corresponding European Patent Application No. 17802186, dated Apr. 29, 2019.

Shimogaki et al., "Intercalation of Mono-and Difunctional Azobenzenes as Photoresponsible Guest Molecules into Poly (muconic acid) Host Crystals" *Macromol. Chem. Phys.,* 2011, 212:1767-1777. (Abstract Only).

Yoshida et al., "Development of Field-Effect Transistor-Type Photorewritable Memory Using Photochromic Interface Layer" *Japanese Journal of Applied Physics* 2010, 49, 4 pages.

Zhang et al., "Photocontrol of charge injection/extraction at electrode/semiconductor interfaces for high-photoresponsivity organic transistors," *Journal of Materials Chemistry C,* 2016, 4:5289-5296. (Abstract Only).

* cited by examiner

PHOTOISOMERIC COMPOUNDS AND DEVICE COMPRISING THE SAME

CROSS-REFERENCE TO RELATED APPLICATIONS

This application is a divisional of U.S. patent application Ser. No. 16/303,597, filed Nov. 20, 2018, which is a national phase under 35 U.S.C. § 371 of International Application No. PCT/CN2017/085720, filed May 24, 2017, which claims priority to Chinese Patent Application No. 201610346549.5, entitled "PHOTOISOMERIC COMPOUNDS AND DEVICES COMPRISING THE SAME", filed on May 24, 2016 before the China National Intellectual Property Administration, and Chinese Patent Application No. 201610383815.1, entitled "PHOTOISOMERIC COMPOUNDS AND DEVICES COMPRISING THE SAME", filed on Jun. 1, 2016 before the China National Intellectual Property Administration, the entire contents of each of which are incorporated herein by reference.

TECHNICAL FIELD

The invention relates to the field of single-molecule photoswitch, and particularly to photoisomeric compounds and devices comprising the same.

BACKGROUND OF THE INVENTION

Rapidly growing research in nanoscience has implications for the development of computing devices, solar energy harvesting, chemical sensing, photonics and optoelectronics, biomedical electronics (e.g. cell-chip connections, cyborg cells, electroceuticals and prosthetics) and biofuel cells. The development of electronic devices based on controllable molecular conduction aims to meet the urgent demand of further device miniaturization on one hand, and the need to effectively interface organic and inorganic materials for biomedical and nanoelectronic applications on the other. To this end, diverse approaches to molecular nanodevices have been proposed and have faced important issues of reproducibility and stability.

Switches are the basic components of almost all electronic devices. The manufacturing of reliable electronic switches is crucial for the possibility to use molecules as electronic devices. Molecular switches have been investigated for two decades, but only a few studies have demonstrated unidirectional switches (namely, irreversible changes) in molecular conduction. One of the most challenging problems in fabricating reliable (namely, stable and reproducible) molecular switches is the lack of effective control of properties of the molecule-electrode interface. Particularly, only unidirectional optoelectronic switching (from closed and conductive diarylethene to open and nonconductive diarylethene) is observed for single diarylethenes sandwiched between gold electrodes via Au—S bonds. This response is due to quenching of the excited state of the open molecular configuration in the presence of the gold electrode. Therefore, the development of reversible, reproducible and stable molecular switches has become an urgent problem to be solved in the art.

Flexible memory is a major development direction in the field of information storage in the future. Flexible nonvolatile organic memory transistors, as an important type of flexible memory, are cost effective and have excellent performance in processibility at low temperature and in large-scale, bendability and the like, in addition to the advantages of a general field-effect transistor memory. Despite of broad application prospects in the aspects of RFID tags, flexible integrated circuits and flexible displays, and the like, flexible non-volatile organic memory transistors are still at the experimental development stage, and their storage stability, erasability and reproducibility still need to be further improved and optimized. Therefore, the development of flexible nonvolatile organic memory transistors with high storage stability, good erasability and good reproducibility is still a problem to be solved in the field.

Photo-responsive organic transistors, also known as light-sensitive field-effect transistors, are working based on photoinduction, and widely used. Organic photosensitive field-effect transistors fabricated by various organic and polymeric semiconductors have been reported. However, the device is still unsatisfactory in the light response rate, reversibility and reproducibility. Therefore, it is necessary to further develop a photo-responsive organic transistor having a high photo-responsive rate, good reversibility, and good reproducibility.

SUMMARY OF THE INVENTION

The object of the present invention is to provide a plurality of photoisomeric compounds and to prepare a molecular switch device with reversible photoelectric conversion, a transistor device with a good reproducibility, such as a flexible non-volatile organic memory transistor device and a photo-responsive organic transistor device, by using a photoisomeric compound.

Firstly, the present invention provides a diarylethene compound having any one of the following general formulas:

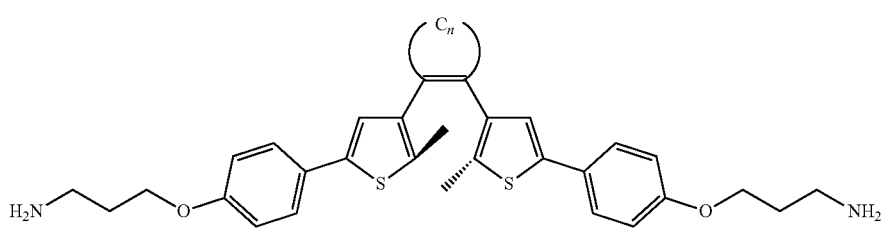

Formula 1

-continued

Formula 2

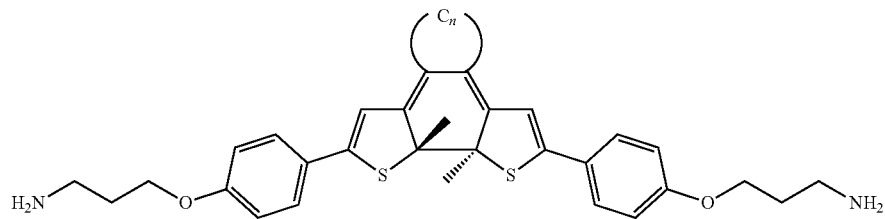

Formula 3

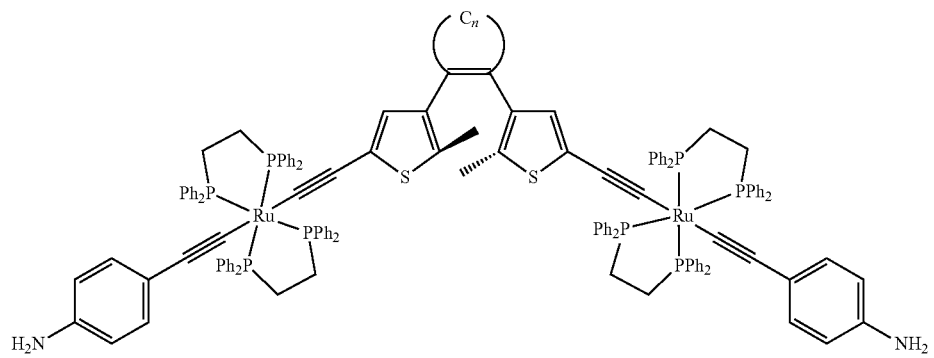

Formula 4

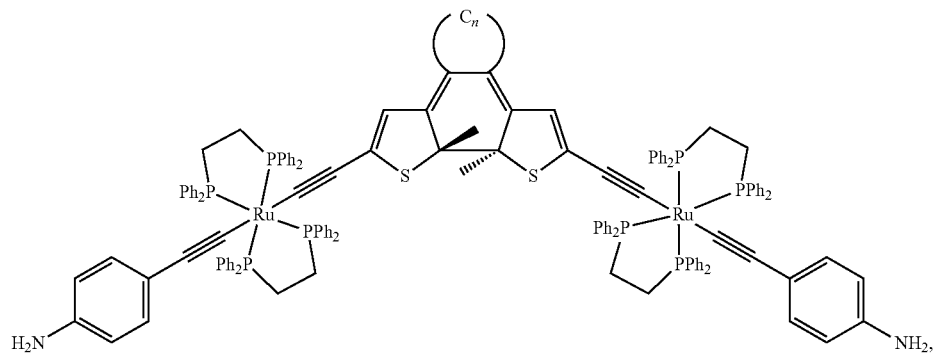

wherein $C_n$ represents a linear alkylene group having 3-4 carbon atoms, and H of this alkylene group can be substituted with at least one F, Cl, Br or I.

Under certain light conditions, the compounds of Formula 1 and Formula 2 can be converted into each other, and the compounds of Formula 3 and Formula 4 can be converted into each other.

In a specific embodiment of the present invention, the compounds of the above general formulas can be any one of the structures represented by the following formulas:

Formula I-1

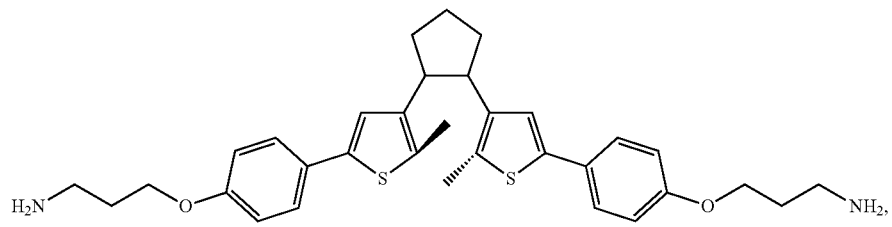

-continued
Formula I-2
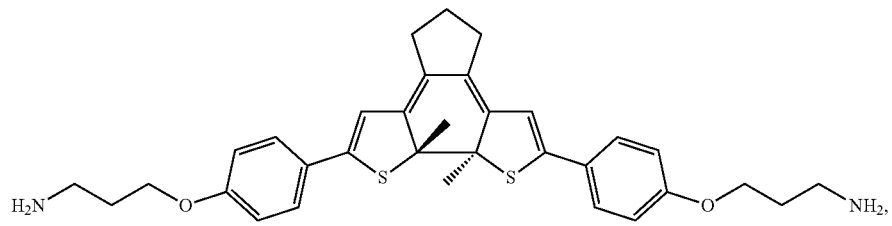
Formula II-1
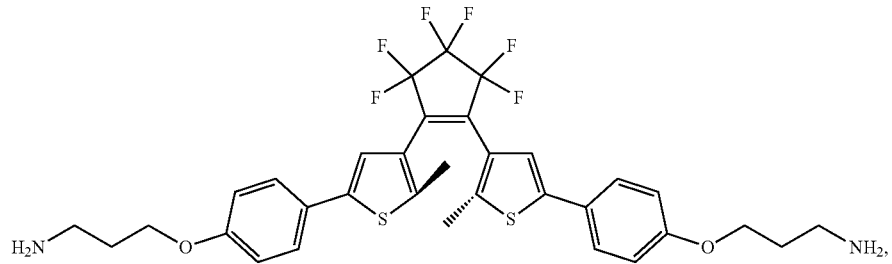
Formula II-2
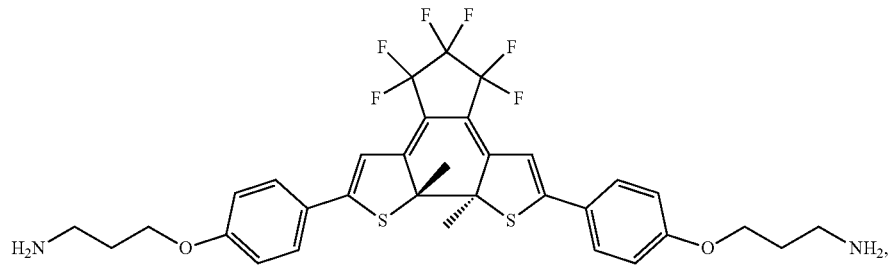
Formula III-1
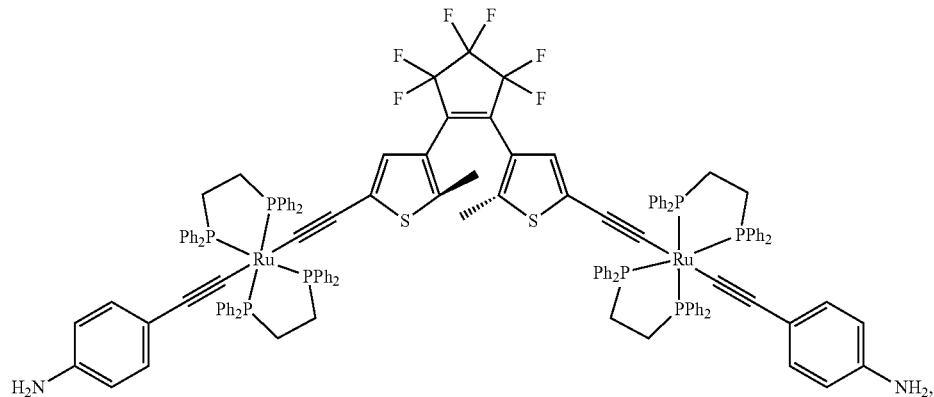
Formula III-2
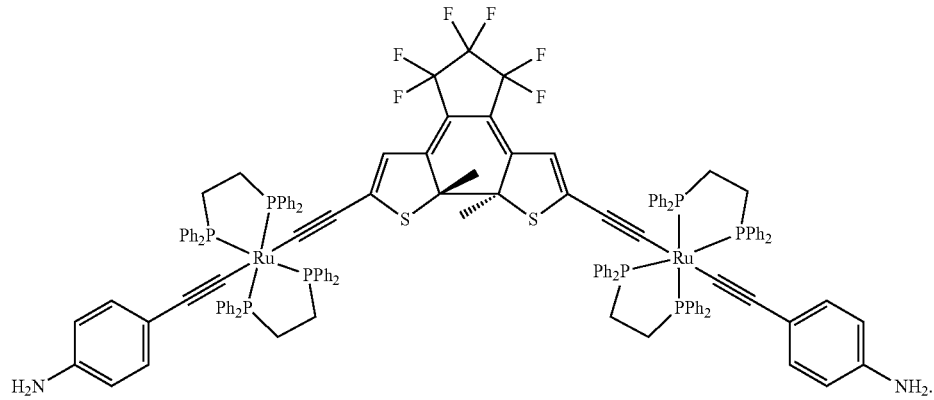

The diarylethene compounds of Formula I-1, Formula II-1 and Formula III-1 above will undergo a ring-closure reaction to form the compounds of Formula I-2, Formula II-2 and Formula III-2 respectively under certain conditions, for example, under ultraviolet light radiation, preferably under ultraviolet light with a wavelength of 365 nm.

The diarylethene compounds of Formula I-2, Formula II-2, and Formula III-2 will undergo a ring-opening reaction to form the structures represented by Formula I-1, Formula II-1, and Formula III-1 respectively under other conditions, for example, under visible light radiation, preferably under visible light with a wavelength no less than 540 nm.

It should be understood that, unless otherwise specified, the diarylethene compounds of the present invention comprise both the diarylethene compounds in open configuration (e.g., as shown by Formula 1, Formula 3, Formula I-1, Formula II-1, and Formula III-1) and the diarylethene compounds in closed configuration (e.g., as shown by Formula 2, Formula 4, Formula I-2, Formula II-2, and Formula III-2).

The present invention also provides a first reversible light-controlled molecular switch device using a diarylethene-graphene junction device provided by the present invention, comprising any one of the diarylethene-graphene junction devices mentioned above. The first reversible light-controlled molecular switch device exhibits a high-conductive state under ultraviolet light radiation; and the first reversible light-controlled molecular switch device exhibits a low-conductive state under visible light radiation.

The term "under ultraviolet light radiation" according to the present invention includes after radiation with ultraviolet light or under continuous radiation with ultraviolet light. The term "under visible light radiation" according to the present invention includes after radiation with visible light or under continuous radiation with visible light.

The terms "high-conductive state" and "low-conductive state" mentioned in the present invention refer to two relative conductive states of any one of the switch devices of the present invention under a certain condition. In order to illustrate the relative correlation between the two conductive states, the present invention hereby defines a technical term "conductance", which refers to the ratio of a current to a voltage corresponding to the current. The conductance of the high-conductive low-conductive state herein is greater than that of low-conductive state. Further, unless otherwise specified, the voltage mentioned or concerned in the present invention has the same meaning as the "bias" and "source-drain bias" present herein.

For a first reversible light-controlled molecular switch device provided by the present invention, the conductance ratio of the high-conductive state to the low-conduction state is not less than 100.

In a specific embodiment of the present invention, the first reversible light-controlled molecular switch device further comprises a visible light generating means and an ultraviolet light generating means for emitting visible light or ultraviolet light to the first reversible light-controlled molecular switch device. When exposed to visible light, the diarylethene compound contained in the first reversible light-controlled molecular switch device of the present invention turns to an open configuration as represented by Formula 1, Formula 3, preferably Formula I-1, Formula II-1 or Formula III-1, and the light-controlled molecular switch device exhibits a low conductive state; and when exposed to ultraviolet light, the diarylethene compound contained in the first reversible light-controlled molecular switch device of the present invention turns to a closed configuration as represented by Formula 2, Formula 4, preferably Formula I-2, Formula II-2 or Formula III-2, and the light-controlled molecular switch device exhibits a high conductive state.

The present invention provides a reversible electrically-controlled molecular switch device by using a diarylethene-graphene molecular junction device provided by the present invention. The reversible electrically-controlled molecular switch device comprises the diarylethene-graphene molecular junction device mentioned above and a voltage generating means connected to the molecular junction device. The voltage generating means is used to supply:

(a) a voltage of 0.2 V to 1.5 V or a voltage of −0.2 V to −1.5 V; or (b) a voltage of −0.9 V to 0.9 V, or a voltage greater than 1.5 V or less than −1.5 V, across the molecular junction device.

In the circumstance that the voltage generating means supplies a voltage of 0.2 V to 1.5 V or a voltage of −0.2 V to −1.5 V across the molecular junction device, when the reversible electrically-controlled molecular switch device comprises the diarylethene compound of Formula 1 or Formula 2, preferably Formula I-1 or Formula I-2, the reversible electrically-controlled molecular switch device exhibits random switching between a high conductive state and a low conductive state at a temperature of 160 K to 220 K; and when the electrically-controlled molecular switch device comprises a diarylethene compound of any of Formulas 1-4, preferably Formula II-1, Formula II-2, Formula III-1 or Formula III-2, the reversible electrically-controlled molecular switch device exhibits random switching between a high conductive state and a low conductive state at a temperature of 100 K to 300 K.

In the circumstance that the voltage generating means supplies a voltage of −0.9 V to 0.9 V, or a voltage greater than 1.5 V or less than −1.5 V across the molecular junction device, when the reversible electrically-controlled molecular switch device comprises the diarylethene compound of Formula 1 or Formula 2, preferably Formula I-1 or Formula I-2, the reversible electrically-controlled molecular switch device exhibits a low conductive state in a voltage range of −0.9 V to 0.9 V and exhibits a high conductive state in a voltage of greater than 1.5 V or less than −1.5 V at a temperature of 160 K to 220 K; when the reversible electrically-controlled molecular switch device comprises a diarylethene compound of any of Formulas 1-4, preferably Formula II-1, Formula II-2, Formula III-1 or Formula III-2, the reversible electrically-controlled molecular switch device exhibits a low conductive state under a voltage ranging from −0.9 V to 0.9 V and exhibits a high conductive state under a voltage of greater than 1.5 V or less than −1.5 V at a temperature of 100 K to 300 K.

Preferably, the diarylethene compound in the reversible electronically-controlled molecular switch device has a structure represented by Formula I-2, Formula II-2 or Formula III-2.

In a specific embodiment of the present invention, the present invention provides a first reversible electrically-controlled molecular switch device by using a diarylethene-graphene molecular junction device of the present invention. The first reversible electrically-controlled molecular switch device comprises the diarylethene-graphene molecular junction device mentioned above and a voltage generating means connected to the molecular junction device. The voltage generating means is to supply a voltage of 0.9 V to 1.5 V or a voltage of −0.9 V to −1.5 V across the molecular junction device containing diarylethene-graphene of Formula 1 or Formula 3, preferably Formula I-1, Formula II-1 or Formula III-1, or to supply a voltage of 0.2 V to 1.5 V or a voltage of −0.2 V to −1.5 V across the molecular junction device containing diarylethene-graphene of Formula 2 or Formula 4, preferably Formula I-2, Formula II-2 or Formula III-2; wherein the voltage is also referred as source-drain bias voltage. In the circumstance that the first reversible electrically-controlled molecular switch device comprises the diarylethene compound of Formula 1 or Formula 2, preferably Formula I-1 or Formula I-2, when a voltage of 0.9 to 1.5 V or a voltage of −0.9 to −1.5 V is supplied across the molecular junction device containing the diarylethene compound of Formula 1, preferably Formula I-1, or when a voltage of 0.2 to 1.5 V or a voltage of −0.2 to −1.5 V is supplied across the molecular junction device containing the diarylethene compound of Formula 2, preferably Formula I-2, the first reversible electrically-controlled molecular switch device exhibits random switching between a high conductive state and a low conductive state at a temperature of 160 K to 220 K. In the circumstance that the first reversible electrically-controlled molecular switch device comprises a diarylethene compound of any of Formulas 1-4, preferably Formula II-1, Formula II-2, Formula III-1 or Formula III-2, when a voltage of 0.9 V to 1.5 V or a voltage of −0.9 V to −1.5 V is supplied across the molecular junction device containing the diarylethene compound of Formula 1 or Formula 3, preferably Formula II-1 and Formula III-1, or when a voltage of 0.2 V to 1.5 V or a voltage of −0.2 V to −1.5 V is supplied across the molecular junction device containing the diarylethene compound of Formula 2 or Formula 4, preferably Formula II-2 and Formula III-2, the first reversible electrically-controlled junction exhibits random switching between a high conductive state and a low conductive state at a temperature of 100 K to 300 K. For the first reversible electrically-controlled molecular switch device of the present invention, a conductance ratio of the high conductive state to the low conductive state is not less than 6.

It should be noted that, regardless the corresponding diarylethene compound of the molecular junction device is of open or closed configuration, theoretically, random switching between a high conductive state and a low conductive state can be achieved under a specific source-drain bias voltage.

The source-drain bias voltage value corresponding to the diarylethene compound of open configuration is larger than that of the diarylethene compound of closed configuration.

In a preferred embodiment of the present invention, for the first reversible electrically-controlled molecular switch device mentioned above, the diarylethene compound in the diarylethene-graphene molecular junction device is that of closed configuration, i.e., the diarylethene compound of Formula I-2, Formula II-2 or Formula III-2.

In a specific embodiment of the present invention, the present invention provides a second reversible electrically-controlled molecular switch device by using a diarylethene-graphene molecular junction device provided by the present invention. The second reversible electrically-controlled molecular switch device comprises the diarylethene-graphene molecular junction device mentioned above and a voltage generating means connected to the molecular junction device. The voltage generating means is to supply a voltage of −0.9 V to 0.9 V across the molecular junction device containing diarylethene-graphene of Formula 1 or Formula 3, preferably Formula I-1, Formula II-1 or Formula III-1, or to supply a voltage of −0.2 V to 0.2 V, or a voltage of more 1.5 V or less than −1.5 V across the molecular junction device containing diarylethene-graphene of Formula 2 or Formula 4, preferably Formula I-2, Formula II-2 or Formula III-2. In the circumstance that the second reversible electrically-controlled molecular switch device comprises a diarylethene compound of Formula 1 or Formula 2, preferably Formula I-1 or Formula I-2, at a temperature of 160 K to 220 K, when a voltage of −0.9 V to 0.9 V is supplied across the molecular junction device containing the diarylethene compound of Formula 1, preferably Formula I-1, or when a voltage of −0.2 V to 0.2 V is supplied across a molecular junction device containing the diarylethene compound of Formula 2, preferably Formula I-2, the electrically-controlled molecular switch device exhibits a low conductive state; and when a voltage of more than 1.5 V or less than −1.5 V is supplied across the molecular junction device, the second reversible electrically-controlled molecular switch device exhibits a high conductive state. In the circumstance that the second reversible electrically-controlled molecular switch device comprises a diarylethene compound of any of Formulas 1-4, preferably Formula II-1, Formula II-2, Formula III-1 or Formula III-2, at a temperature of 100 K to 300 K, when a voltage of −0.9 V to 0.9 V is supplied across the molecular junction device containing the diarylethene compound of Formula 1 or Formula 3, preferably Formula II-1 and Formula III-1, or when a voltage of −0.2 V to 0.2 V is supplied across the molecular junction device containing the diarylethene compound of Formula 2 or Formula 4, preferably Formula II-2 and Formula III-2, the second reversible electrically-controlled molecular switch device exhibits a low conductive state; and when a voltage of more than 1.5 V or less than −1.5 V is supplied across the molecular junction device, the second reversible electrically-controlled molecular switch device exhibits a high conductive state. The conductance of the high conductive state of the second reversible electrically-controlled molecular switch device provided by the present invention is not less than that of the first reversible electrically-controlled molecular switch device provided by the present invention under ±1.5 V. The conductance of the low conductive state of the second reversible electrically-controlled molecular switch device provided by the present invention is not greater than that of the first reversible electrically-controlled molecular switch devices provided by the present invention under ±0.2 V.

In a preferred embodiment of the present invention, for the second reversible electrically-controlled molecular switch device mentioned above, the diarylethene compound in the diarylethene-graphene molecular junction device is that of closed configuration, i.e., the diarylethene compound of Formula I-2, Formula II-2 or Formula III-2.

The present invention also provides a first reversible temperature-controlled molecular switch device by using a diarylethene-graphene molecular junction device provided by the present invention. The first reversible temperature-controlled molecular switch device comprises the diarylethene-graphene molecular junction device mentioned above. In the circumstance that the first reversible temperature-controlled molecular switch device comprises the diarylethene compound of Formula 1 or Formula 2, preferably Formula I-1 or Formula I-2, the first reversible temperature-controlled molecular switch device exhibits a low conductive state at a temperature below 160 K, and a high conductive state at a temperature above 220 K. In the circumstance that the first reversible temperature-controlled molecular switch device comprises a diarylethene compound of any of Formulas 1-4, preferable Formula II-1, Formula II-2, Formula III-1 or Formula III-2, the temperature-controlled molecular switch device exhibits a low conductive state at a temperature below 100 K, and a high conductive state at a temperature above 300 K. The conductance of the high conductive state of the first reversible temperature-controlled molecular switch device provided by the present invention is not less than that of the first reversible electrically-controlled molecular switch device provided by the present invention under ±1.5 V. The conductance of the low conductivity state of the first reversible temperature-controlled molecular switch device is not greater than that of the first reversible electrically-controlled molecular switch device of the present invention under ±0.2 V.

In a specific embodiment of the present invention, the first reversible temperature-controlled molecular switch device mentioned above may further comprise a temperature control means for providing the device with a temperature below 160 K or a temperature above 220 K, or providing the device with a temperature below 100 K or a temperature above 300 K. In the present invention, the expression of "temperature of . . . K" refers to the thermodynamic temperature in Kelvin (K).

The present invention also provides a transistor device comprising any one of the above-mentioned diarylethene compounds, which is assembled between a dielectric layer and a semiconductor layer of an organic field-effect transistor, or assembled between an electrode and a semiconductor layer of an organic field-effect transistor.

In a specific embodiment of the invention, the transistor device is a first flexible non-volatile organic memory transistor device (also referred to as a flexible non-volatile organic memory device) comprising any one of the above-mentioned diarylethene compounds assembled between a dielectric layer and a semiconductor layer of an organic field-effect transistor. The first flexible non-volatile organic memory transistor device is obtained by assembling any one of the above-mentioned diarylethene compounds as a photoactive layer between a dielectric layer and a semiconductor layer of an organic field-effect transistor, and it has a function of light-controlled and electrically-controlled memory storage.

In a specific embodiment of the present invention, the transistor device can be a first photo-responsive organic transistor device (also referred to as an organic field-effect transistor device) comprising any one of the above-mentioned diarylethene compounds assembled between an electrode and a semiconductor layer of an organic field-effect transistor. The first photo-responsive organic transistor device is obtained by assembling any one of the above-mentioned diarylethene compounds as a photoactive layer between an electrode and a semiconductor layer of an organic field-effect transistor, and it has a function of reversible photo-response.

The three methylene groups (or Ru-coordinated groups) at both ends of the functional center of the diarylethene compound play a pivotal role in endowing the molecular switch device comprising the diarylethene compound a function of reversible light-controlled switching and electrically-controlled switching. Similarly, a function of reversible light-controlled switching and electrically-controlled switching is also achieved in a system of photoisomerized azobenzene molecule and a system of photoisomerized spiropyran molecule by using such design.

Therefore, in addition to the diarylethene compounds mentioned above, the present invention also provides an azobenzene compound having any one of

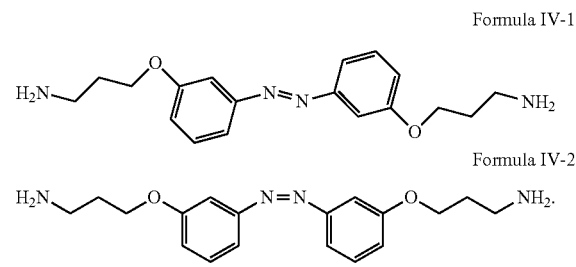

Formula IV-1

Formula IV-2

The azobenzene compound of Formula IV-1 turns to a configuration represented by Formula IV-2 under ultraviolet light (preferably with a wavelength of 365 nm); and the azobenzene compound of Formula IV-2 turns to a configuration represented by Formula IV-1 under visible light (with a wavelength >460 nm).

The present invention further provides an azobenzene-graphene molecular junction device by using an azobenzene compound of the present invention. The molecular junction device comprises any one of the aforementioned azobenzene compounds which is linked via an amide covalent bond between a gap of a two-dimensional monolayer graphene having nanogap array.

The present invention further provides a second reversible light-controlled molecular switch device by using an azobenzene-graphene molecular junction device of the present invention. A second reversible light-controlled molecular switch device comprises any one of the azobenzene-graphene molecular switch devices mentioned above. A second reversible light-controlled molecular switch device exhibits a low conductive state under ultraviolet light, and in a high conductive state under visible light. In a second reversible light-controlled molecular switch device of the present invention, a conductance ratio of the high conductive state to the low conductive state is not less than 3.

In a specific embodiment of the present invention, a second reversible light-controlled molecular switch device further comprises a visible light generating means and an ultraviolet light generating means for respectively emitting visible light or ultraviolet light to the second reversible light-controlled molecular switch device. When exposed to visible light, the azobenzene compound contained in a second reversible light-controlled molecular switch device of the present invention turns to a configuration of Formula Iv-1, and the light-controlled molecular switch device exhibits a high conductive state. When exposed to ultraviolet light, the azobenzene compound contained in the second reversible light-controlled molecular switch device of the present invention turns to a configuration of Formula IV-2, and the light-controlled molecular switch device exhibits a low conductive state.

The present invention also provides a reversible electrically-controlled molecular switch device by using an azobenzene-graphene molecular junction device of the present invention. The reversible electrically-controlled molecular switch device comprises an azobenzene-graphene molecular junction device mentioned above, and a voltage generating means connected to the molecular junction device. The voltage generation means is used to supply:
(a) a voltage of 0.2 V to 1.5 V or −0.2 V to −1.5 V; or
(b) a voltage of −0.9 V to 0.9 V, or a voltage greater than 1.5 V or less than −1.5 V, across the molecular junction device.

When the voltage generating means supplies a voltage of 0.2 V to 1.5 V or a voltage of −0.2 V to −1.5 V across the molecular junction device, the reversible electrically-controlled molecular switch device exhibits random switching between a high conductive state and a low conductive state at a temperature of 100 K to 300 K.

When the voltage generating means supplies a voltage of −0.9 V to 0.9 V across the molecular junction device, or supplies a voltage greater than 1.5 V or less than −1.5 V across the molecular junction device, the reversible electrically-controlled molecule switch device exhibits a low conductive state under the voltage ranging from −0.9 V to 0.9 V, and exhibits a high conductive state under a voltage of more than 1.5 V or less than −1.5 V at a temperature of 100 K to 300 K.

Preferably, the azobenzene compound in the azobenzene-graphene molecular junction devices has a structure represented by Formula IV-1.

In a specific embodiment of the present invention, it provides a third reversible electrically-controlled molecular switch device by using an azobenzene-graphene molecular junction device of the present invention. The third reversible electrically-controlled molecular switch device comprises an azobenzene-graphene molecular junction device mentioned above and a voltage generating means connected to the molecular junction device. The voltage generating means is used to supply a voltage of 0.2 V to 1.5 V or −0.2 V to −1.5 V across the molecular junction device containing azobenzene-graphene of Formula IV-1, or to supply a voltage of 0.9 V to 1.5 V or −0.9 V to −1.5 V across the molecular junction device containing azobenzene-graphene of Formula IV-2. In this instance, the third reversible electrically-controlled molecular switch device exhibits random switching between a high conductive state and a low conductive state at a temperature of 100 K to 300 K. In the third reversible electrically-controlled molecular switch device provided by the present invention, the conductance ratio of the high conductive state to the low conductive state is not less than 2.

In a specific embodiment of the present invention, for the third reversible electrically-controlled molecular switch device, the azobenzene compound in the azobenzene-graphene molecular junction device has a structure represented by Formula IV-1.

The present invention provides a fourth reversible electrically-controlled molecular switch device by using an azobenzene-graphene molecular junction device of the present invention. The fourth reversible electrically-controlled molecular switch device comprises an azobenzene-graphene molecular junction device mentioned above and a voltage generating means connected to the molecular junction device. The voltage generating means is used to supply a voltage of −0.2 V to 0.2 V across the molecular junction device containing azobenzene-graphene of Formula IV-1, or to supply a voltage of −0.9 V to 0.9 V across the molecular junction device containing azobenzene-graphene of Formula IV-2. In this instance, the fourth reversible electrically-controlled molecular switch device exhibits a low conductive state at a temperature of 100 K to 300 K. The voltage generating means is also used to supply a voltage of more than 1.5 V or less than −1.5 V across the molecular junction device, in this instance, the fourth reversible electrically-controlled molecular switch device exhibits a high conductive state at a temperature of 100 K to 300 K. The conductance of the high conductive state of the fourth reversible electrically-controlled molecular switch device of the present invention is not less than that of the third reversible electrically-controlled molecular switch device of the present invention under ±1.5 V. The conductance of the low conductive state of the fourth reversible electrically-controlled molecular switch device of the present invention is not greater than that of the third reversible electrically-controlled molecular switch devices of the present invention under ±0.2 V.

In a specific embodiment of the present invention, for the fourth reversible electrically-controlled molecular switch device, the azobenzene compound in the azobenzene-graphene molecular junction device has a structure represented by Formula IV-1.

The present invention provides a second reversible temperature-controlled molecular switch device by using an azobenzene-graphene molecular junction device of the present invention. The second reversible temperature-controlled molecular switch device comprises an azobenzene-graphene molecular junction device mentioned above, and exhibits a low conductive state at a temperature below 100 K, and a high conductive state at a temperature above 300 K. The conductance of the high conductive state of the second reversible temperature-controlled molecular switch device provided by the present invention is not less than that of the third reversible electrically-controlled molecular switch device of the present invention under ±1.5 V. The conductance of the low conductivity state of the second reversible temperature-controlled molecular switch device provided by the present invention is not greater than that of the third reversible electrically-controlled molecular switch device of the present invention under ±0.2 V.

In a specific embodiment of the present invention, the second reversible temperature-controlled molecular switch device may further comprise a temperature control means for providing the device with a temperature below 100 K or a temperature above 300 K.

The present invention also provides a transistor device comprising any one of the above-mentioned azobenzene compounds assembled between a dielectric layer and a semiconductor layer of an organic field-effect transistor, or assembled between an electrode and a semiconductor layer of an organic field-effect transistor.

In a specific embodiment of the present invention, the transistor device is a second flexible non-volatile organic memory transistor device comprising any one of the above-mentioned azobenzene compounds assembled between the dielectric layer and the semiconductor layer of the organic field-effect transistor. The second flexible non-volatile organic memory transistor device is obtained by assembling any one of the above-mentioned azobenzene compounds as a photoactive layer between a dielectric layer and a semiconductor layer of an organic field-effect transistor, and has a function of light-controlled and electrically-controlled memory storage.

In a specific embodiment of the invention, the transistor device is a second photo-responsive organic transistor device comprising any one of the above-described azobenzene compounds assembled between the electrode and the semiconductor layer of the organic field-effect transistor. The second photo-responsive organic transistor device is obtained by assembling any one of the above-mentioned azobenzene compound as a photoactive layer between an electrode and a semiconductor layer of an organic field-effect transistor, and has a function of reversible photo-response.

The present invention further provides a spiropyran compound having any one of the following structures:

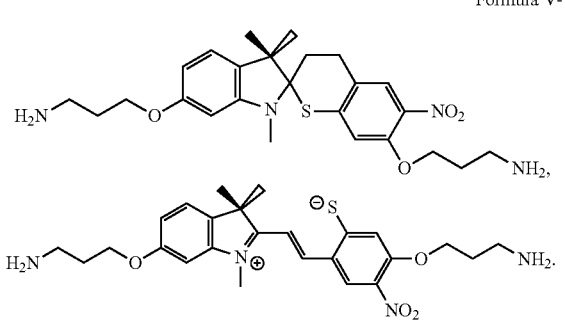

Formula V-1

Formula V-2

The spiropyran compound of Formula V-1 turns to an open configuration of Formula V-2 under ultraviolet light (preferably with a wavelength of 365 nm); and the spiropyran compound of Formula V-2 turns to a closed configuration of Formula V-1 under visible light (with a wavelength >520 nm).

The present invention further provides an spiropyran-graphene molecular junction device by using a spiropyran compound of the present invention. The molecular junction device comprises any one of the above-mentioned spiropyran compounds linked via an amide covalent bond between a gap of a two-dimensional monolayer graphene having nanogap array.

The present invention further provides a third reversible light-controlled molecular switch device by using a spiropyran-graphene molecular junction device of the present invention. The third reversible light-controlled molecular switch device comprises any one of the spiropyran-graphene molecular junction devices mentioned above, and exhibits a high conductive state under ultraviolet light, and a low conductive state under visible light. In the third reversible light-controlled molecular switch devices of the present invention, a conductance ratio of the high conductive state to the low conductive state is not less than 10.

In a specific embodiment of the present invention, the third reversible light-controlled molecular switch device further comprises a visible light generating means and an ultraviolet light generating means for respectively emitting visible light or ultraviolet light to the third reversible light-controlled molecular switch device. When exposed to visible light, the spiropyran compound contained in the third reversible light-controlled molecular switch device of the present invention turns to a closed configuration of Formula V-1, and the light-controlled molecular switch device exhibits a low conductive state. When exposed to ultraviolet light, the spiropyran compound contained in the third reversible light-controlled molecular switch device of the present invention turns to an open configuration of Formula V-2, and the light-controlled molecular switch device exhibits a high conductive state.

The present invention also provides a reversible electrically-controlled molecular switch device by using a spiropyran-graphene molecular junction device of the present invention. The reversible electrically-controlled molecular switch device comprises a spiropyran-graphene molecular junction device mentioned above, and a voltage generating means connected to the molecular junction device. The voltage generation means is used to supply:

(a) a voltage of 0.2 V to 1.5 V or −0.2 V to −1.5 V; or
(b) a voltage of −0.9 V to 0.9 V, or a voltage greater than 1.5 V or less than −1.5 V, across the molecular junction device.

When the voltage generating means supplies a voltage of 0.2 V to 1.5 V or a voltage of −0.2 V to −1.5 V across the molecular junction device, the reversible electrically-controlled molecular switch device exhibits random switching between a high conductive state and a low conductive state at a temperature of 100 K to 300 K; When the voltage generating means supplies a voltage of −0.9 V to 0.9 V across the molecular junction device, or supplies a voltage greater than 1.5 V or less than −1.5 V, the reversible electrically-controlled molecular switch device exhibits a low conductive state under a voltage ranging from −0.9 V to 0.9 V, and exhibits a high conductive state under a voltage of more than 1.5 V or less than −1.5 V at a temperature of 100 K to 300 K.

Preferably, the spiropyran compound in the spiropyran-graphene molecular junction device has a structure represented by Formula V-2.

In a specific embodiment of the present invention, the present invention provides a fifth reversible electrically-controlled molecular switch device by using a spiropyran-graphene molecular junction device of the present invention. The fifth reversible electrically-controlled molecular switch device comprises a spiropyran graphene molecular junction device mentioned above and a voltage generating means connected to the molecular junction device.

The voltage generating means is used to supply a voltage of 0.9 V to 1.5 V or a voltage of −0.9 V to −1.5 V across the molecular junction device containing spiropyran-graphene of Formula V-1, or to supply a voltage of 0.2 V to 1.5 V or a voltage of −0.2 V to −1.5 V across the molecular junction device containing spiropyran-graphene of Formula V-2. In this instance, the fifth reversible electrically-controlled molecular switch device exhibits random switching between a high conductive state and a low conductive state at a temperature of 100 K to 300 K. In the fifth reversible electrically-controlled molecular switch device of the present invention, the conductance ratio of the high conductive state to the low conductive state is not less than 3.

In a specific embodiment of the present invention, for the fifth reversible electrically-controlled molecular switch device, the spiropyran compound in the spiropyran-graphene molecular junction device has a structure of Formula V-2.

In a specific embodiment of the present invention, the present invention provides a sixth reversible electrically-controlled molecular switch device by using a spiropyran-graphene molecular junction device of the present invention. The sixth reversible electrically-controlled molecular switch device comprises the spiropyran-graphene molecular junction device mentioned above and a voltage generating means connected to the molecular junction device. The voltage generating means is used to supply a voltage of −0.9 V to 0.9 V across the molecular junction device containing spiropyran-graphene of Formula V-1, or to supply a voltage of −0.2 V to 0.2 V across the molecular junction device containing spiropyran-graphene of Formula V-2. In this instance, the sixth reversible electrically-controlled molecular switch device exhibits a low conductive state at a temperature of 100 K to 300 K. The voltage generating means is also used to supply a voltage of more than 1.5 V or less than −1.5 V across the molecular junction device. In this instance, the sixth reversible electrically-controlled molecular switch device exhibits a high conductive state at a temperature of 100 K to 300 K. The conductance of the high conductive state of the sixth reversible electrically-controlled molecular switch device of the present invention is not less than that of the fifth reversible electrically-controlled molecular switch device of the present invention under ±1.5 V. The conductance of the low conductive state of the sixth reversible electrically-controlled molecular switch device of the present invention is not greater than that of the fifth reversible electrically-controlled molecular switch devices of the present invention under ±0.2 V.

In a specific embodiment of the present invention, for the sixth reversible electrically-controlled molecular switch device, the spiropyran compound in the spiropyran-graphene molecular junction device has a structure represented by Formula V-2.

The present invention provides a third reversible temperature-controlled molecular switch device by using the spiropyran-graphene molecular junction device of the present invention. The third reversible temperature-controlled molecular switch device comprises a spiropyran-graphene molecular junction device mentioned above, and exhibits a low conductive state at a temperature below 100 K, and a high conductive state at a temperature above 300 K. The conductance of the high conductive state of the third reversible temperature-controlled molecular switch device of the present invention is not less than that of the fifth reversible electrically-controlled molecular switch device of the present invention under ±1.5 V. The conductance of the low conductivity state of the third reversible temperature-controlled molecular switch device of the present invention is not greater than that of the fifth reversible electrically-controlled molecular switch device of the present invention under ±0.2 V.

In a specific embodiment of the present invention, the third reversible temperature-controlled molecular switch device further comprises a temperature control means for providing the device with a temperature below 100 K or a temperature above 300 K.

The present invention also provides a transistor device comprising any one of the above-mentioned spiropyran compounds assembled between a dielectric layer and a semiconductor layer of an organic field-effect transistor, or assembled between an electrode and a semiconductor layer of an organic field-effect transistor.

In a specific embodiment of the present invention, the transistor device is a third flexible non-volatile organic memory transistor device comprising any one of the above-mentioned spiropyran compounds assembled between the dielectric layer and the semiconductor layer of the organic field-effect transistor. The third flexible non-volatile organic memory transistor device is obtained by assembling any one of the above-mentioned spiropyran compounds as a photoactive layer between a dielectric layer and a semiconductor layer of an organic field-effect transistor, and has a function of light-controlled and electrically-controlled memory storage.

In a specific embodiment of the invention, the transistor device is a third photo-responsive organic transistor device comprising any one of the above-described spiropyran compounds assembled between the electrode and the semiconductor layer of the organic field-effect transistor. The third photo-responsive organic transistor device is obtained by assembling any one of the above-mentioned spiropyran compound as a photoactive layer between an electrode and a semiconductor layer of an organic field-effect transistor, and has a function of reversible light-response.

The diarylethene-graphene molecular junction device provided by the present invention has a function of reversible photoelectric conversion, and the molecular switch device prepared thereby can realize reversibility and a good reproducibility of a molecular switch. For the light-controlled molecular switch device provided, the number of light-controlled molecular switching cycles can exceed $10^4$. For the electrically-controlled molecular switch device provided, the random switching between a high conductive state and a low conductive state can reach about $10^6$ to $10^7$ times. Furthermore, the reversible molecular switch device of the present invention remains stable for more than one year.

The azobenzene-graphene molecular junction device provided by the present invention also has a function of reversible light-controlled molecular switching and electrically-controlled molecular switching. The switch device exhibits a low conductive state under ultraviolet light, and exhibits a high conductive state under visible light. For the light-controlled molecular switch device provided, the number of light-controlled molecular switching cycles can exceed $10^4$. For the electrically-controlled molecular switch device provided, the random switching between a high conductive state and a low conductive state can reach about $10^4$ to $10^5$ times.

The spiropyran-graphene molecular junction device provided by the present invention also has a function of reversible light-controlled molecular switching and electrically-controlled molecular switching. The switch device exhibits a high conductive state under ultraviolet light, and exhibits a low conductive state under visible light. For the light-controlled molecular switch device provided, the number of light-controlled molecular switching cycles can exceed $10^4$. For the electrically-controlled molecular switch device provided, the random switching between a high conductive state and a low conductive state can reach about $10^4$ to $10^5$ times.

It should be noted that the first to the third flexible non-volatile organic memory transistor devices of the present invention can be constructed according to the flexible non-volatile organic memory transistor device shown in the literature (H. Chen et al., 2016). All devices constructed can achieve more than $10^4$ memory cycles. This article is hereby incorporated by reference in its entirety, and will not be described in details herein.

It should be noted that the first to the third photo-responsive organic transistor devices of the present invention can be constructed according to the photo-responsive organic transistor device shown in the literature (H. Zhang et al., 2016). All devices constructed can achieve more than $10^3$ cycles of reversible photo-response. This article is hereby incorporated by reference in its entirety in its entirety, and will not be described herein.

BRIEF DESCRIPTION OF THE DRAWINGS

In order to more definitely illustrate the technical solutions in the examples of the present invention and the prior art, the drawings used in the following examples and the prior art are briefly introduced. Obviously, the drawings in the following description are only parts of examples in the present invention, and those skilled in the art can obtain other drawings according to these drawings without any creative work.

FIG. 1A shows I-V characteristics of a molecular junction device containing a diarylethene compound represented by Formula I-1 (dashed line) or a diarylethene compound represented by Formula I-2 (solid line), when the gate voltage is $V_G=0$ V; $V_D$ is source-drain voltage, and $I_D$ is source leakage current. FIG. 1B shows a real-time measurement of the current through a molecular junction device comprising a diarylethene compound in an open ring form or a diarylethene compound in a closed ring form upon exposure to ultraviolet (UV) and visible (Vis) radiation, respectively; $V_D$=100 mV, $V_G$=0 V. In FIG. 1, "UV on" represents starting radiation with ultraviolet light, "UV off" represents stopping radiation with ultraviolet light, "Vis on" represents starting radiation with visible light, and "Vis off" represents stopping radiation with visible light.

FIGS. 3A-3H are the conductance-time (G-t) curves under the bias voltages of 0.1 V, 0.3 V, 0.5 V, 0.7 V, 0.9 V, 1.2 V, 1.5 V and 1.8 V, respectively, with a time interval of 100 ms.

DETAILED DESCRIPTION OF THE INVENTION

Figure 1A:
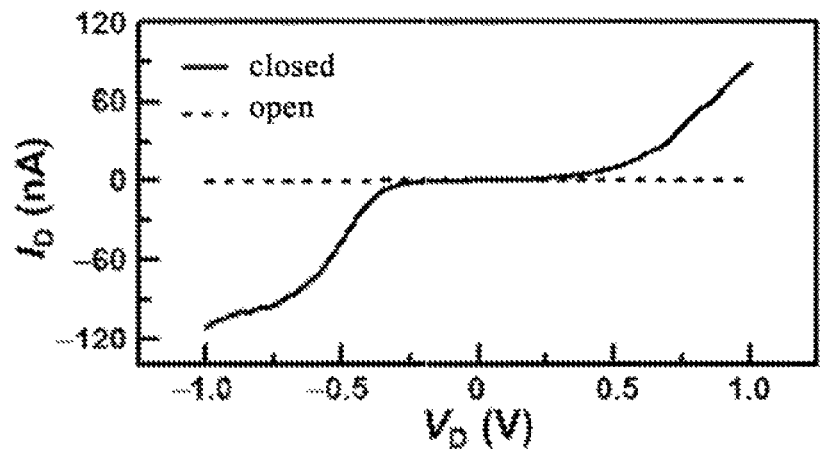
FIGS. 1A-1B are a characteristic diagram of an light-controlled reversible switching of a diarylethene-graphene molecular junction device prepared in Example 2.

The present invention will be further described in detail below with reference to the accompanying drawings. It is apparent that the described examples are only parts of not all the examples of the invention. All other examples obtained by those skilled in the art based on the examples of the present invention without creative efforts are within the scope of the present invention.

The present invention firstly provides a method for preparing a compound of Formula I-1, comprising the steps as follows.

Starting compound 1 and starting compound 3 are prepared, wherein the starting compound 1 is 1,2-bis(5-chloro-2-methylthiophen-3-yl)cyclopentene, and the starting compound 3 is tert-butyl-3-(4-bromophenoxy)propyl-carbamate. The starting compound 1 can be prepared by the method described in the literature (L. N. Lucas et al., 1998); and the starting compound 3 can be prepared by the method described in the literature (Y. Chen et al., 2012). The entire disclosure of these literatures is hereby incorporated by reference in its entirety, and will not be described in detail herein.

The starting compound 1 is reacted with trimethyl borate in the presence of n-butyllithium. After the reaction is completed, a mixture containing the starting compound 3, tetrakis(triphenylphosphine)palladium and potassium carbonate is added to obtain an intermediate product 4 having the following structure:

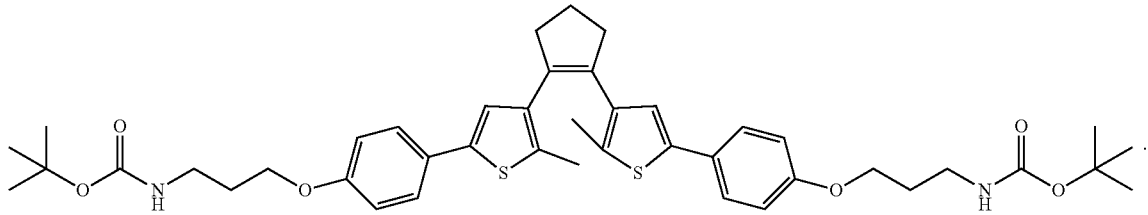

4

In a specific embodiment of the present invention, the starting compound 1 is dissolved in dehydrated THF, and stirred under an inert atmosphere and at a low temperature, e.g., −10° C. to 0° C. (this can be achieved by an ice-salt bath). Then, n-butyllithium is slowly added, stirred at room temperature for a period of time, preferably 20 to 60 minutes, and B (OCH$_3$)$_3$ is added for further reaction of 2 h to 6 h to obtain an intermediate reaction system.

The starting compound 3, tetrakis(triphenylphosphine) palladium and potassium carbonate are dissolved in a mixed solvent of THF and H$_2$O to obtain a mixture. The obtained intermediate reaction system is heated to 50° C. to 80° C., before the above mixture containing the starting compound 3 is added thereto, then is heated to reflux, and react for 8 h to 24 h. After the reaction is completed, the reaction products are poured into water, and extracted with an organic solvent, preferably dichloroethane, to obtain an organic layer. The organic layer is dried to remove various solvent to give the crude. The crude is purified by silica gel column chromatography to obtain intermediate product 4.

The intermediate product 4 is reacted with trifluoroacetic acid in an organic solvent, preferably dichloromethane, for 1 h to 4 h. The whole system is then slowly added into a saturated aqueous solution of NaHCO$_3$, and then extracted with dichloromethane. The organic layer is washed with saturated aqueous NaHCO$_3$ and brine. The diarylethene compound having a structure of Formula I-1 provided by the present invention is obtained by drying and removing the solvent.

The invention also provides a method for preparing a diarylethene-graphene molecular junction device, comprising the following steps:

preparing a two-dimensional monolayer graphene having a nanogap array;

dissolving any one of the diarylethene compound provided by the present invention, and then radiating the diarylethene compound solution obtained with visible light at a wavelength of not less than 520 nm; and adding a two-dimensional monolayer graphene with a nanogap array and 1-ethyl-3-(3-dimethylaminopropyl) carbodiimide hydrochloride into a solution of a diarylethene compound for reaction for 1-4 days in dark, and then washing and drying the resultant.

In the present invention, the "two-dimensional monolayer graphene having a nanogap array" can be prepared by the method described in the literature (C. Jia et al., 2013; or Y. Cao et al., 2012). This literature is hereby incorporated by reference in its entirety, and will not be described in detail herein.

In a particular embodiment of the invention, pyridine can be used to dissolve the diarylethene compound. Absence of light can also be understood as being in dark conditions. Those ordinary skilled in the art know the meaning for absence of light or dark conditions.

In a specific embodiment of the present invention, after the reaction in dark is completed, a two-dimensional monolayer graphene having a nanogap array is taken out from the solution, washed with a large amount of acetone and ultrapure water, and dried in $N_2$ gas stream. In the present invention, the ultrapure water used preferably has a resistivity of more than 18 MΩ·cm.

Example 1: Synthesis of the Diarylethene Compound of Formula I-1

All reagents and chemicals were obtained commercially and used without further purification, unless otherwise indicated. All reactions were carried out in dry solvent and in an inert atmosphere of argon using standard Schlenk technology (also known as Chirac technique or double row tube operation technique). $^1H$ and $^{13}C$ NMR spectra were recorded on a Variance Mercury plus 300 MHz and Bruker ARX 500 NMR spectrometer. All chemical shifts of $^1H$ NMR were referenced to tetramethylsilane (TMS, δ=0.00 ppm) or $CDCl_3$ (δ=7.26 ppm), and $^{13}C$ NMR chemical shifts were referenced to $CDCl_3$ (δ=77.00 ppm). Mass spectra were recorded on a Bruker APEX IV mass spectrometer. Elemental analysis was performed by using the Flash EA1112 analyzer.

The synthetic route of an amino-terminated diarylethene compound (compound 5 in an open configuration, namely, the compound of Formula I-1) having three methylene ($CH_2$) groups on each side is as follows:

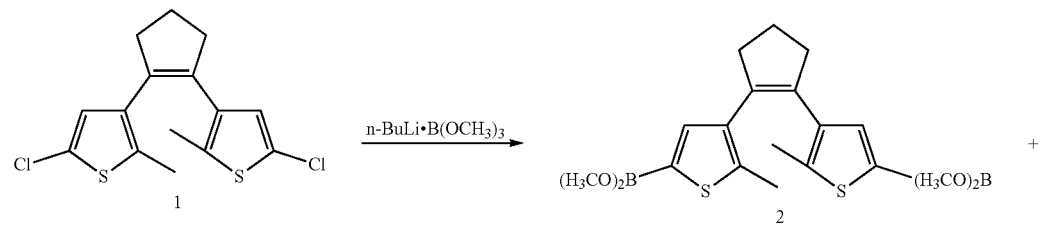

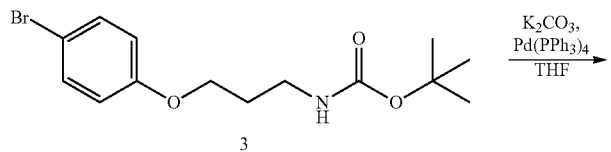

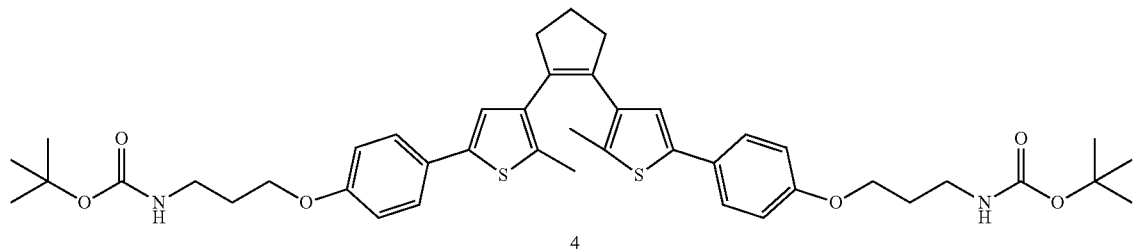

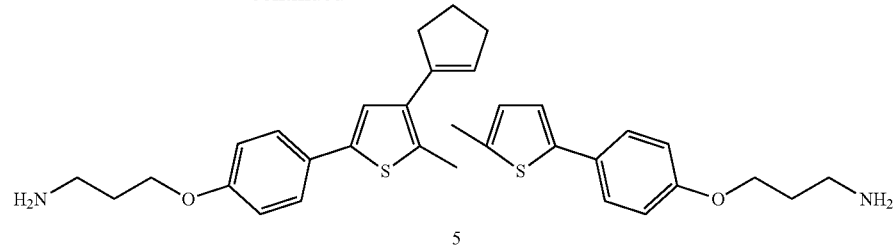

5

1,2-bis(5-chloro-2-methylthiophen-3-yl)cyclopentene (compound 1) and tert-butyl-3-(4-bromophenoxy)propyl-carbamate (compound 3) were synthesized according to the method described in the previously reported literatures.

Compound 1 (0.328 g, 1 mmol) was dissolved in 5 mL of dry THF. After being stirred for 10 minutes in an ice-salt bath in an argon atmosphere, 2.5 M n-butyl lithium (0.96 mL, 2.4 mmol) was injected slowly, followed by stirring for 45 minutes at room temperature. Then, B(OCH$_3$)$_3$ (0.6 mL, 3 mmol) was added and stirred for further 4 hours to afford compound 2. After that, the reaction mixture was heated up to 60° C. Compound 3 (0.729 g, 2.4 mmol), Pd(PPh$_3$)$_4$ (83 mg, 0.072 mmol) and K$_2$CO$_3$ (1.0 g, 7.2 mmol) were dissolved in THF/H$_2$O (10 mL/4 mL), the mixture was injected into the above reaction mixture and stirred at reflux overnight. After cooling, the reaction mixture was poured into water (50 mL), and extracted with CH$_2$Cl$_2$ (3×30 mL). The combined organic layers were dried over Na$_2$SO$_4$ and solvent was removed under reduced pressure. The crude product was purified by chromatography on a silica gel column to afford compound 4 as a yellow solid.

$^1$H NMR (400 MHz, CDCl$_3$, 298 K): δ 7.41 (d, J=8.7 Hz, 4H), 6.92 (s, 2H), 6.86 (d, J 8.7 Hz, 4H), 4.81 (s, 2H), 4.02 (t, J=5.9 Hz, 4H), 3.33 (d, J=6.0 Hz, 4H), 2.84 (t, J 7.4 Hz, 4H), 2.06 (m, 2H), 1.98 (s, 6H), 1.45 (s, 18H), 0.87 (dd, J=14.5, 7.3 Hz, 4H).

$^{13}$C NMR (100 MHz, CDCl$_3$, 298 K): δ 157.99, 156.03, 139.42, 136.58, 134.59, 133.49, 127.64, 126.59, 123.02, 114.77, 79.25, 65.92, 38.47, 38.03, 29.52, 28.43, 23.03, 14.38. HRMS (TOF-ESI$^+$) (m/z): C$_{43}$H$_{55}$N$_2$O$_6$S$_2$ calcd for: 959.3505 [M+H$^+$]; found 959.3502.

After that, trifluoroacetic acid (1.0 mL, 0.34 g, 3.73 mmol) was added dropwise to a solution of compound 4 (0.1 g) in dichloromethane (10 mL), and the mixture was stirred for 2 h at room temperature, and then added dropwise into saturated aqueous solution of NaHCO$_3$ (20 mL). The solution was extracted with dichloromethane (50 mL). The organic layer was washed with saturated aqueous solution of NaHCO$_3$ (30 mL) and brine, and dried over MgSO$_4$. The solvent was evaporated in vacuum to give the target compound 5 (i.e., compound of Formula I-1) as a dark brown solid.

$^1$H NMR (400 MHz, DMSO, ppm): δ 7.92 (s, 4H, —NH$_2$), 7.45 (d, J=8.6 Hz, 4H), 7.13 (s, 2H), 6.94 (d, J=8.6 Hz, 4H). 4.06 (t, J=5.7 Hz, 4H), 2.97 (t, J=6.9 Hz, 4H), 2.82 (t, J=7.0 Hz, 4H), 2.01 (m, 4H), 1.91 (s, 6H), 1.23 (m, 2H). $^{13}$C NMR (100 MHz, DMSO, ppm): δ 157.61, 138.76, 136.52, 134.11, 132.35, 128.77, 126.66, 126.12, 123.10, 115.01, 64.67, 38.01, 36.27, 26.80, 13.93. HRMS (MALDI-TOF-ESI$^+$) (m/z): C$_{33}$H$_{39}$N$_2$O$_2$S$_2$ calcd for: 559.2448 [M+H$^+$]; found: 559.2466.

Example 2: Fabrication of the Diarylethene-Graphene Molecular Junction Device of Formula I-1

A two-dimensional monolayer graphene having a nanogap array was fabricated by using a dash-line lithographic (DLL) method as described detailedly in the aforementioned literatures. For molecular reconnection, the diarylethene compound of Formula I-1 was first dissolved in pyridine at a concentration of about 10$^{-4}$ M. The solution was then radiated with visible light (>520 nm) to ensure that the diarylethene compound of Formula I-1 was in open configuration. Finally, the graphene devices and 1-ethyl-3-(3-dimethylaminopropyl)carbodiimide hydrochloride (EDCI), a well-known carbodiimide dehydrating/activating agent, were added to the solution of the diarylethene compound of Formula I-1 for reconnection for two days in dark. Thereafter, the reconnected graphene devices was taken out from the solution, washed with copious acetone and ultrapure water, and dried in N$_2$ gas stream.

Characterization of the Diarylethene-Graphene Molecular Junction Device Prepared in Example 2

(1) Characterization of Switching Characteristics of Light-Controlled Molecular Molecular Junction Devices The characterization of the molecular junction devices at room temperature was performed by using an Agilent 4155C semiconductor characterization system and a Karl Suss (PM5) manual probe station in ambient atmosphere. Light radiation was performed with a hand-held UV lamp (WFH-2048, Shanghai Tanghui Electronics Co., Ltd.) (~100 μW/cm$^2$, λ=365 nm) and with a monochromatic visible light (~240 μW/cm$^2$, λ=540 nm). The monochromatic light was generated by a grating monochromator with a 150 W halogen incandescent lamp (TLS 1509-150A, Zolix instruments Ltd., Beijing). To avoid heating during the radiation, visible light was focused and guided by a long optical fiber up to about 2 cm from the molecular junction devices. For typical real-time measurements of switching characteristics of light-controlled molecular junction devices at room temperature, ultraviolet and visible lights were toggled back and forth at standard atmospheric conditions. For stability measurements, the molecular junction devices were kept in a dark metal box under standard atmospheric conditions for more than a year. Then the molecular junction devices were taken out and subjected to similar measurements.

Figure 1B:
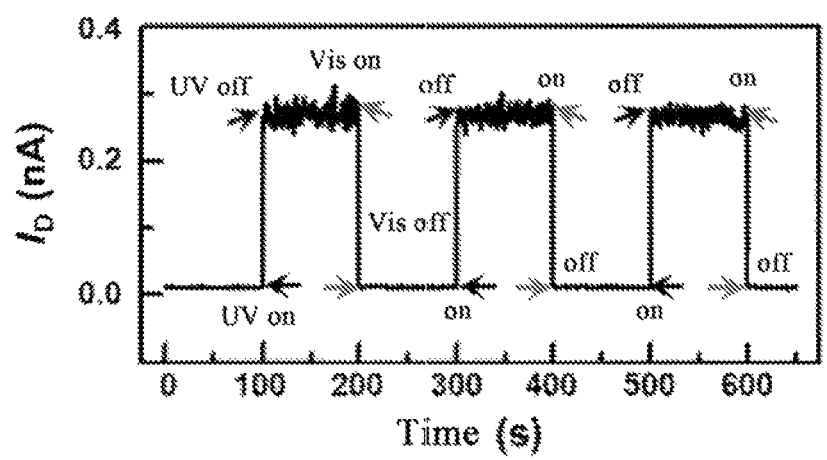
Figure 2A:
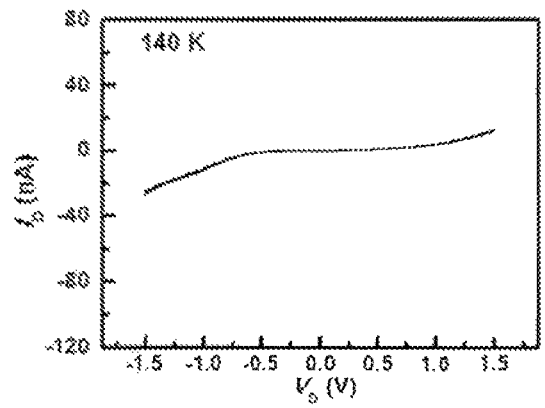
FIGS. 2A-2F show current-voltage (I-V) curves of a molecular junction device comprising the diarylethene compound represented by Formula I-2 prepared in Example 2 at different temperatures, 140 K, 160 K, 180 K, 200 K, 220 K and 240 K, respectively.
Figure 2B:
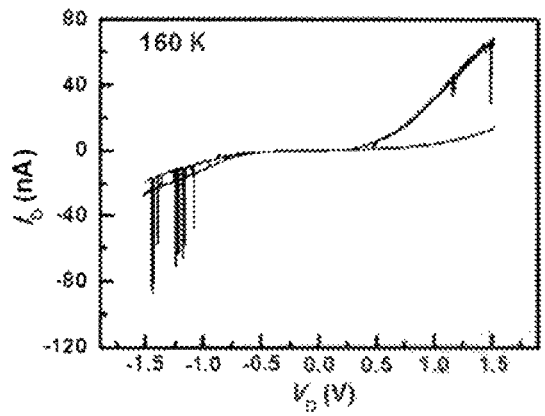
Figure 2C:
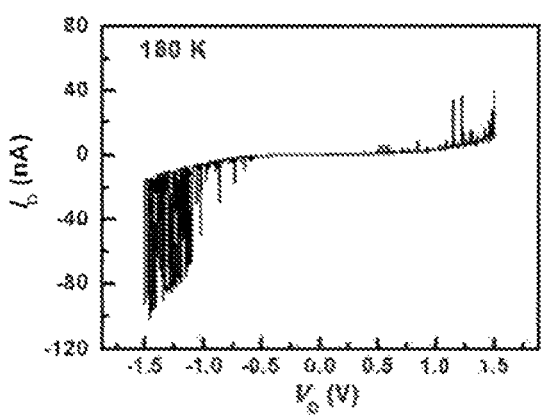
Figure 2D:
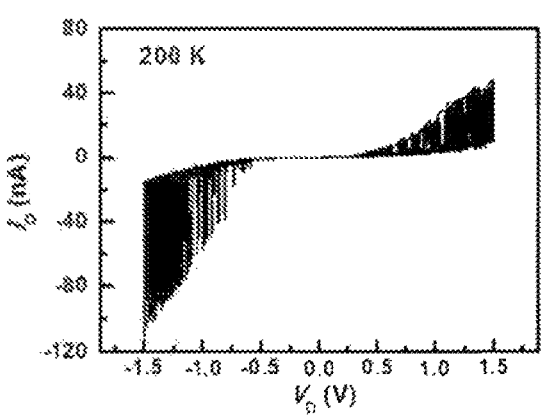
Figure 2E:
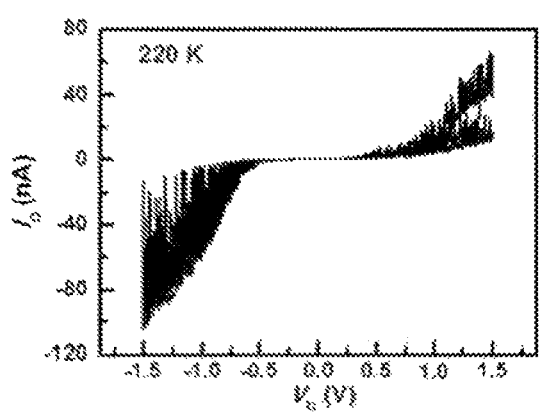
Figure 2F:
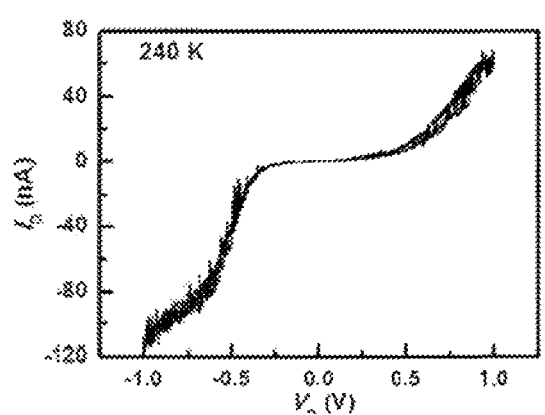
Figure 3A:
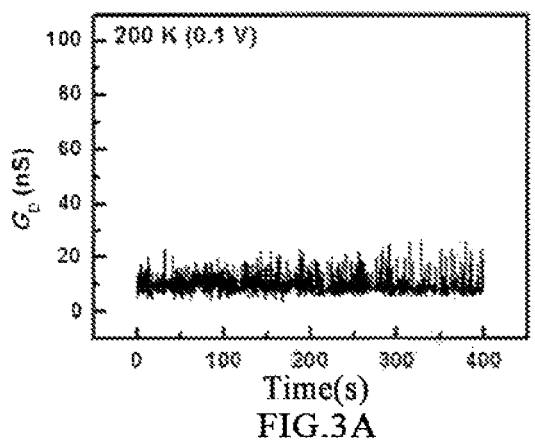
FIGS. 3A-3H show real-time measurement results of electrically-controlled switching performance of a molecular junction device comprising the diarylethene compound of Formula I-2 prepared in Example 2 under different bias voltages at 200 K.
Figure 3B:
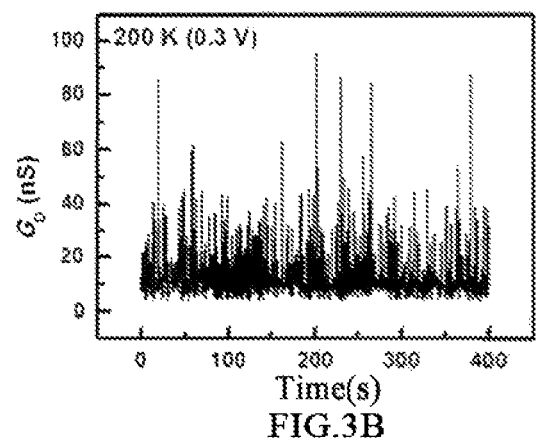
Figure 3C:
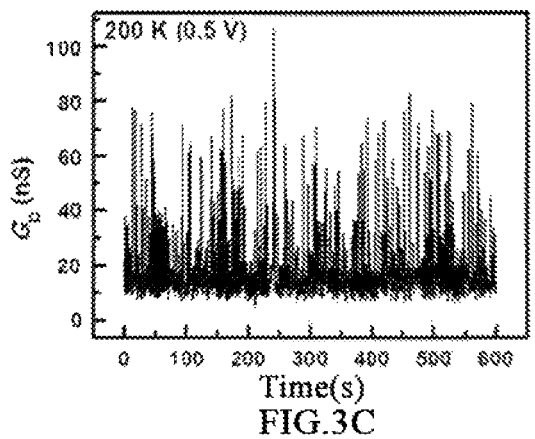
Figure 3D:
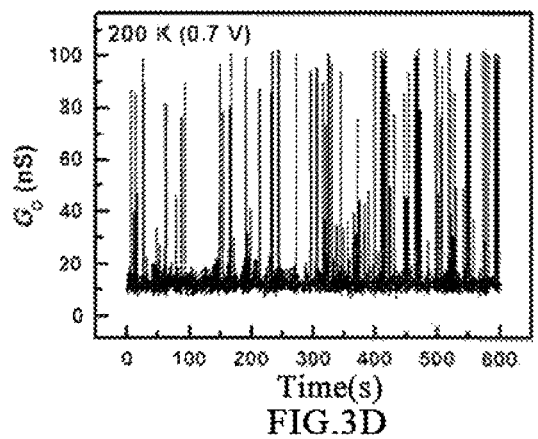
Figure 3E:
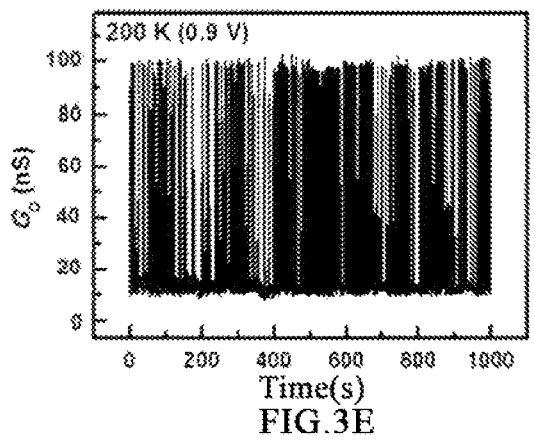
Figure 3F:
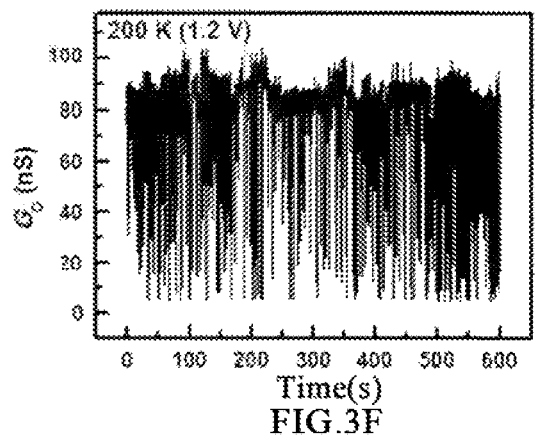
Figure 3G:
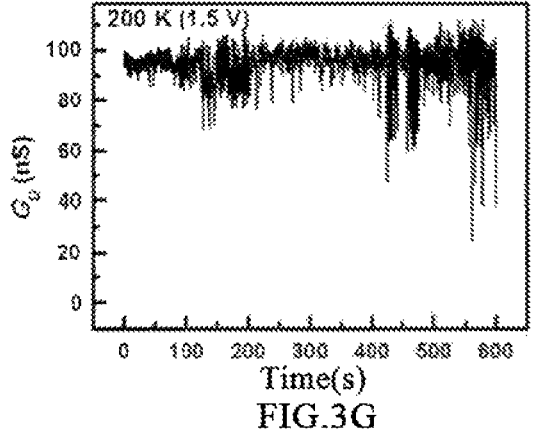
Figure 3H:
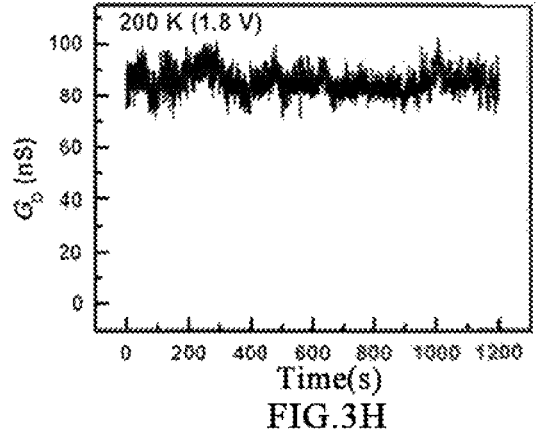

The results are shown in FIG. 1. As can be seen from FIG. 1A, the diarylethene compound turns to an open configuration under visible light, the I$_D$ changes little with V$_D$, and the molecular junction device exhibits a low conductive state. Under ultraviolet light, the diarylethene compound turns to a closed configuration, the I$_D$ changes greatly with V$_D$, and the molecular junction device exhibits a high conductive state. As can be seen from FIG. 1B, the switching of the whole molecular junction device is reversible and reproducible.

Based on this, a reversible light-controlled molecular switch device was prepared in an example of the present invention, comprising at least the diarylethene-graphene molecular junction device prepared in Example 2 (containing an diarylethene compound of Formula I-1 or Formula I-2). The light-controlled molecular switch device exhibits a high conductive state under ultraviolet light, equivalent to switch on; and the light-controlled molecular switch device exhibits a low conductive state under visible light, equivalent to switch off. Accordingly, reversible switching is achieved. Moreover, the reversible light-controlled molecular switch device may further comprise a visible light generating means and an ultraviolet light generating means for radiating the reversible light-controlled molecular switch device with visible light or ultraviolet light. The visible light generating means and the ultraviolet light generating means can be obtained by an ordinary skilled person in the art in accordance with the invention herein, without any creative work, and are not limited herein. For example, the visible light generating means and the ultraviolet light generating means can utilize a 50 W xenon light source PLS-SXE300/300 UV light source (Beijing Bofeilai Technology Co., Ltd.) and then provide ultraviolet light at 365 nm and visible light at 540 nm using a monochromator.

(2) Characterization of Switching Characteristics of an Electrically-Controlled Molecular Junction Devices (Containing the Diarylethene Compound of Formula I-2)

Characterization of temperature-dependent I-V characteristics of the diarylethene-graphene molecular junction devices (the diarylethene compound turns to a closed configuration under UV radiation) was carried out by using an Agilent 4155C semiconductor characterization system and ST-500-probe station (Janis Research Company) with liquid nitrogen and liquid helium cooling. Real-time recording of random switching was performed at a low temperature and in vacuum (at a pressure of less than $1*10^{-4}$ Pa). The results are shown in FIGS. 2 and 3.

The following conclusions can be drawn from the above results.

(1-1) It can be seen from the current-voltage (I-V) curve (e.g., shown in FIG. 2) and the corresponding conductance-time (G-t) curve at different bias voltages (e.g., shown in FIG. 3) that, at the temperature of 160 K to 220 K, the molecular junction device exhibits the characteristics of random switching between a high conductive state and a low conductive state under a source-drain voltage of 0.2 V to 1.5 V or a source-drain voltage of −0.2 V to −1.5 V.

(1-2) When the temperature is below 160 K, the molecular junction device exhibits a continuously low conductive state, and when the temperature is above 220 K, the molecular junction device exhibits a continuously high conductive state.

(1-3) At a temperature of 160 K to 220 K, when the source-drain voltage is between −0.2 V and 0.2 V, the molecular junction device exhibits a low conductive state; it can be seen from the current-voltage (I-V) curve (e.g., shown in FIG. 2) and the corresponding conductance-time (G-t) curve (e.g., shown in FIG. 3) at different bias voltages that, the proportion of the high conductive state increases as the bias voltage increases. When the source-drain voltage is greater than 1.5 V or less than −1.5 V, the molecular junction device exhibits a continuously high conductivity state.

Based on the conclusion (1-1), an example of the present invention provides a reversible electrically-controlled molecular switch device, comprising the diarylethene-graphene molecular junction device provided by example 2 of the present invention. The diarylethene compound turns to a closed configuration, i.e., the structure represented by Formula I-2, under ultraviolet light. When a voltage of 0.2 V to 1.5 V or −0.2 V to −1.5 V is supplied across the molecular junction device, the electrically-controlled molecular switch device exhibits random switching between the high conductive state and the low conductive state at a temperature of 160 K to 220 K. The switch device has the characteristics of random switching of conductive states, and thus can be used for performing logic operations and the like. In addition, the electrically-controlled molecular switch device may further comprise a voltage generating means connected to the molecular junction device for supplying a voltage of 0.2 V to 1.5 V or a voltage of −0.2 V to −1.5 V across the molecular junction device.

Based on the conclusion (1-2), an example of the present invention provides a reversible temperature-controlled molecular switch device, comprising the diarylethene-graphene molecular junction device provided by example 2 of the present invention. The diarylethene compound turns to a closed configuration, i.e., the structure represented by Formula I-2, under ultraviolet light. The temperature-controlled molecular switch device exhibits a low conductive state at a temperature below 160 K; and the temperature-controlled molecular switch device exhibits a high conductive state at a temperature above 220 K. The temperature-controlled molecular switch device can exhibit different switching characteristics at different temperatures. At a temperature below 160 K, the temperature-controlled molecular switch device exhibits a low conductive state, and only has a very small $I_D$, equivalent to switch on. At a temperature above 220 K, the temperature-controlled molecular switch device exhibits a high conductive state, and has a large $I_D$, equivalent to switch off. Thus, the temperature-controlled molecular switch device can be used as a temperature sensor or a temperature sensitive switch. The temperature-controlled molecular switch device can also comprise a temperature control means for providing a temperature below 160 K or a temperature above 220 K for the temperature-controlled molecular switch device. Thus, the regulation of the temperature-controlled molecular switch device can be achieved by adjusting the temperature.

Based on the conclusion (1-3), an example of the present invention provides another reversible electrically-controlled molecular switch device, comprising the diarylethene-graphene molecular junction device provided by example 2 of the present invention. The diarylethene compound turns to a closed configuration, i.e., the structure represented by Formula I-2, under ultraviolet light. At a temperature of 160 K to 220 K, the electrically-controlled molecular switch device exhibits a low conductive state when a voltage of −0.2 V to 0.2 V is supplied across the molecular junction device; and the electrically-controlled molecular switch device exhibits a high conductive state when a voltage of greater than 1.5 V or less than −1.5 V is supplied across the molecular junction device. That is to say, when the applied bias voltage is a low threshold voltage (~0.2 V to 0.2 V), the electrically-controlled molecular switch device is switched-off (low conductive); and when the bias voltage is a high threshold voltage (greater than 1.5 V or less than −1.5 V), the electrically-controlled molecular switch device is switched-on (high conductive). Further, the electrically-controlled molecular switch device may further comprise a voltage generating means connected to the molecular junction device, which is used to supply a voltage of −0.2 V to 0.2 V, or a voltage of greater than 1.5 V or less than −1.5 V to the molecular junction device.

It should be noted that the voltage generating means connected to the molecular junction devices in the above switch devices, can be implemented by using the prior art in this field, for example, a lock-in amplifier, preferably an HF2LI lock-in amplifier (Zurich Instruments Ltd.) can be used as the voltage generating means of the switch device mentioned above. The voltage generating means are not limited in the present invention. Those skilled in the art can obtain the voltage generating means according to the description herein and connect it to the molecular junction device, without any creative work. Further, an ultraviolet light generating means may also be included in the above switch device for radiating the diarylethene compound, so that the diarylethene compound therein turns to a closed configuration, i.e., the structure represented by Formula I-2.

(3) Characterization of Switching Characteristics of Electrically-Controlled Molecular Molecular Junction Devices (Containing the Diarylethene Compounds of Formula I-1)

Characterization of temperature-dependent I-V characteristics of the diarylethene-graphene molecular junction devices (the diarylethene compound turns to an open configuration, i.e., the structure represented by Formula I-1, under visible light radiation) was carried out by using an Agilent 4155C semiconductor characterization system and ST-500-probe station (Janis Research Company) with liquid nitrogen and liquid helium cooling. Real-time recording of random switching was performed at a low temperature and in vacuum (at a pressure of less than $1*10^{-4}$ Pa), and the test results were not shown. The following conclusions can be drawn from the test results.

(1-4) Under a source-drain voltage ranging from 0.9 V to 1.5 V or ranging from −0.9 to −1.5 V, at a temperature of 160 K to 220 K, the molecular junction device exhibits random switching between a high conductive state and a low conductive state.

(1-5) When the temperature is below 160 K, the molecular junction device exhibits a continuously low conductivity state; and when the temperature is above 220 K, the molecular junction device exhibits a continuously high conductive state.

(1-6) At a temperature of 160 K to 220 K, the molecular junction device exhibits a low conductive state under a source-drain voltage ranging from −0.9 V to 0.9 V; and the molecular junction device exhibits a continuously high conductive state under a source-drain voltage of greater than 1.5 V or of less than −1.5 V.

Based on the conclusions (1-4), an example of the present invention provides a reversible electrically-controlled molecular switch device, comprising the diarylethene-graphene molecular junction device provided by example 2 of the present invention. The diarylethene compound turns to an open configuration, i.e., the structure represented by Formula I-1, under visible light. When a voltage ranging from 0.9 V to 1.5 V or from −0.9 V to −1.5 V is supplied across the molecular junction device, the electrically-controlled molecular switch device exhibits random switching between a high conductive state and a low conductive state at a temperature of 160 K to 220 K. The switch device has the characteristics of random switching of conductive states, which can be used for logic operations and the like. In addition, the electrically-controlled molecular switch device may further comprise a voltage generating means connected to the molecular junction device for supplying a voltage ranging from 0.9 to 1.5 V or from −0.9 to −1.5 V to the molecular junction device.

Based on the conclusions (1-5), an example of the present invention provides a reversible temperature-controlled molecular switch device, comprising the diarylethene-graphene molecular junction device provided by example 2 of the present invention. The diarylethene compound turns to an open configuration, i.e., the structure of Formula I-1, under visible light. The temperature-controlled molecular switch device exhibits a low conductive state at a temperature below 160 K, and exhibits a high conductive state at a temperature above 220 K. The temperature-controlled molecular switch device can exhibit different switching characteristics at different temperatures.

When the temperature is below 160 K, the temperature-controlled molecular switch device exhibits a low conductive state and only has a very small $I_D$, which is equivalent to switch on; and when the temperature is above 240 K, the temperature-controlled molecular switch device exhibits a high conductive state and has a large $I_D$, which is equivalent to switch off. Thus, it can be used as a temperature sensor or a temperature sensitive switch. The temperature-controlled molecular switch device can also comprise a temperature control means for providing the temperature-controlled molecular switch device with a temperature below 160 K or a temperature above 220 K. Thus, regulation of the temperature-controlled molecular switch device can be achieved by adjusting the temperature.

Based on the conclusions (1-6), the example of the present invention provides another reversible electrically-controlled molecular switch device, comprising the diarylethene-graphene molecular junction device provided by example 2 of the present invention. The diarylethene compound turns to an open configuration, i.e., the structure represented by Formula I-1, under visible light radiation. At a temperature of 160 K to 220 K, the electrically-controlled molecular switch device exhibits a low conductive state when a voltage ranging from −0.9 to 0.9 V is supplied across the molecular junction device; and the device exhibits a high conductive state when a voltage of greater than 1.5 V or less than −1.5 V across the molecular junction device. That is to say, when the applied bias voltage is a low threshold voltage (~0.9 V to 0.9 V), the electrically-controlled molecular switch device is switched-off (low conductive); and when the bias voltage is a high threshold voltage (greater than 1.5 V or less than −1.5 V), the electrically-controlled molecular switch device is switched-on (high conductive). Further, the electrically-controlled molecular switch device may further comprise a voltage generating means connected to the molecular junction device for supplying a voltage ranging from −0.9 V to 0.9 V, or a voltage of greater than 1.5 V or less than −1.5 V to the molecular junction device.

It should be noted that the voltage generating means connected to the molecular junction devices in the above switch devices, can be implemented by using the prior art in this field, for example, a lock-in amplifier, preferably an HF2LI lock-in amplifier (Zurich Instruments Ltd.) can be used as the voltage generating means of the switch device mentioned above. The voltage generating means are not limited in the present invention. Those skilled in the art can obtain the voltage generating means according to the description herein and connect it to the molecular junction device, without any creative work. Further, a visible light generating means to the above switch device can be included for radiating the diarylethene compound when the diarylethene compound in the above switch devices is needed to exhibit an open configuration.

Flexible non-volatile organic memory transistor devices prepared from the diarylethene compound of Formula I-1 and characterization thereof. The flexible substrate and the hafnium oxide dielectric layer of the organic memory tube were prepared by using the method described in detail in the aforementioned literatures. For molecule assembly, after the preparation of the hafnium oxide dielectric layer, the $HfO_2$ surface was activated with an oxygen plasma etcher (RIE) at a power of 30 W for 3 minutes to produce —OH for the self-assembly reaction. The activated substrate was immersed in a THF/ethanol mixed solution containing the diarylethene compound represented by Formula I-1 (with a concentration of 0.1 mM, THF/ethanol=1:1 (V/V), THF and ethanol were strictly dehydrated) in dark for 24 hours for self-assembly within a glove box under argon. The substrate was taken out, the surface of which was washed with ethanol for three times until no visible particulate impurities was observed. The substrate was annealed at 120° C. on the heating stage for 3 minutes to make the amino anchoring group and the cerium oxide substrate link more firmly. Then, a 30 nm thick of pentacene was vacuum evaporated on the above-mentioned substrate in which the diarylethene monomolecular film was assembled within a thermal evaporater. Finally, a metal electrode was evaporated at a predetermined position of the substrate by thermal evaporation.

Characterization of organic memory transistor devices was performed in ambient atmosphere using an Agilent 4155C semiconductor characterization system and a Karl Suss (PM5) manual probe station at room temperature.

The obtained flexible non-volatile organic memory transistor device uses 633 nm light as a means for writing information. The light radiation conditions in the specific experiment are as follows: the ultraviolet light source is a hand-held UV lamp (energy density I=100 W $cm^{-2}$, wavelength=365 nm); the white light source is a halogen incandescent lamp (energy density I=30 mW $cm^{-2}$, wavelength >420 nm); global light source at 633 nm is a 150 W halogen incandescent light source with a 633 nm cut-off light filter.

Figure 4:
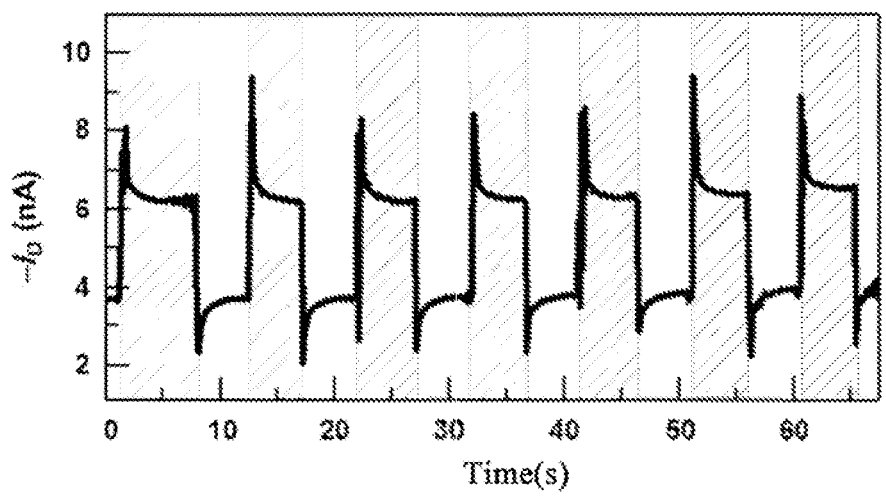
FIG. 4 is a signal storage characteristic diagram of a flexible non-volatile organic transistor device prepared from the diarylethene compound represented by Formula I-1. The device is firstly "preset" by ultraviolet light (365 nm). When the device is exposed to the visible light at 633 nm, the source-drain current increases linearly and rapidly, and the device reaches a high conductive state; after the radiation is stopped, the high conductive state is continuously maintained, thereby realizing the non-volatile light "write". Visible light radiation (540 nm) makes the device switch to its initial electrical state, which in turn serves as an "erase" means of memory devices. Then the next cycle starts by a new "preset".

Characterizations of processes of presetting, writing, and erasing for the flexible non-volatile organic memory transistor devices are described below. Firstly, ultraviolet light (365 nm) was applied to "preset" the device, so as to allow the device to work as a memory device. After the device was preset, visible light radiation at 633 nm can be used to "write" the information thereto. As shown in FIG. 4, when the device was radiated with visible light at 633 nm, the source-drain current increases linearly and reaches a high conductive state; and after the radiation was stopped, the high conductive state was continuously maintained. This result demonstrates the non-volatile storage performance of a photoactive hybrid dielectric layer. Visible light radiation (≥520 nm) makes the diarylethene monomolecular film be switched from Off to On, meanwhile make the device be back to the initial electrical state, and therefore it serves as an "erasing" means for the memory device. At the same time, when a negative gate voltage ($V_G$) is supplied to the gate, the erasing of information can also be achieved.

A Photo-Responsive Organic Transistor Device Prepared from a Diarylethene Compound Represented by Formula I-1 and Characterization Thereof The substrate and the gold electrode of the organic field-effect transistor with a bottom gate bottom contact structure were prepared by using the method described in detail in the aforementioned literatures. For molecule assembly, the surface of the obtained gold electrode was washed with ethanol, and then etched by an oxygen plasma etcher (RIE) at a power of 30 W for 5 minutes to clean the organic substances adsorbed thereon. The cleaned substrate containing the patterned gold electrode pair was immersed in an ethanol solution of the diarylethene compound represented by Formula I-1 (concentration: $10^{-4}$ mol/L) for 24 hours in dark under the protection of Ar gas. The substrate was taken out, the surface of which was washed with ethanol for three times. The substrate was annealed at 100° C. on the heating stage for 2 minutes. Finally, a 40 nm thick of pentacene was vacuum evaporated on the above-mentioned substrate in which the diarylethene monomolecular film was assembled within a thermal evaporater.

Characterization of photo-responsive organic transistor devices at room temperature was performed in ambient atmosphere using an Agilent 4155C semiconductor characterization system and a Karl Suss (PM5) manual probe station. Light radiation was performed with a hand-held UV lamp (WFH-2048, Shanghai Tanghui Electronics Co., Ltd.) (~100 μW/$cm^2$, λ=365 nm) and with a monochromatic visible light (~240 μW/$cm^2$, λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device. For typical real-time measurements of switching characteristics of photo-responsive organic transistor devices at room temperature, ultraviolet and visible lights were toggled back and forth at standard atmospheric conditions.

Figure 5:
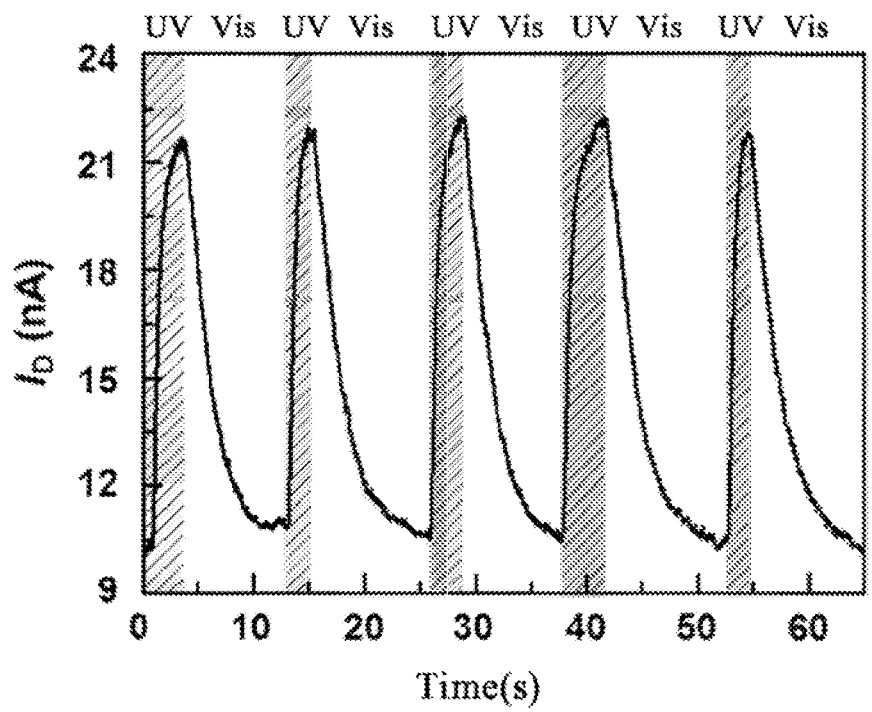
FIG. 5 is a characteristics diagram showing the light-controlled reversible switching of a photo-responsive organic transistor device prepared from the diarylethene compound represented by Formula I-1. When the device is exposed to ultraviolet or visible radiation, a real-time measurement of the current through a photo-responsive transistor device comprising a diarylethene compound in an open configuration or a diarylethene compound in a closed configuration as active layer, respectively; $V_D$=50 mV, $V_G$=0 V.
Figure 6A:
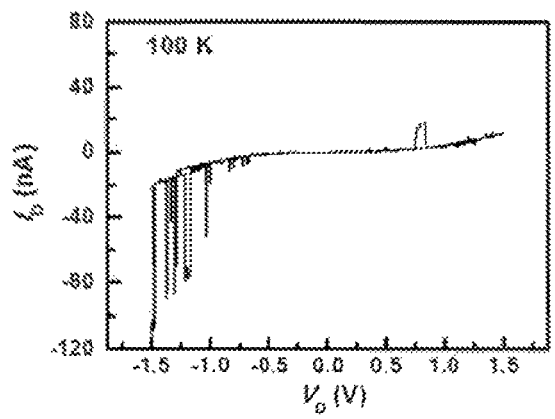
FIGS. 6A-6F show current-voltage (I-V) curves of a molecular junction device comprising the diarylethene compound represented by Formula II-2 prepared in Example 4 at different temperatures, 100 K, 150 K, 200 K, 250 K, 300 K and 320 K, respectively.
Figure 6B:
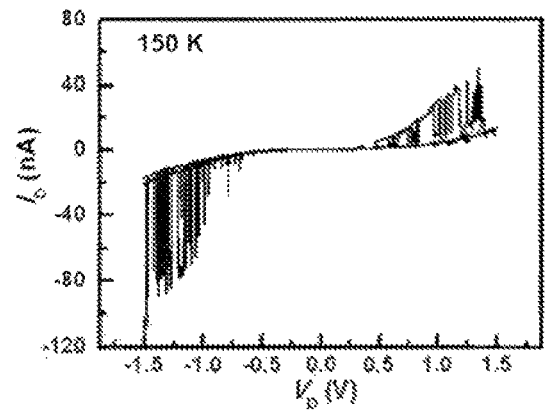
Figure 6C:
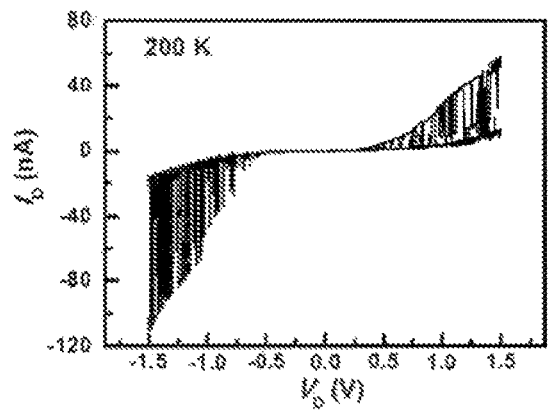
Figure 6D:
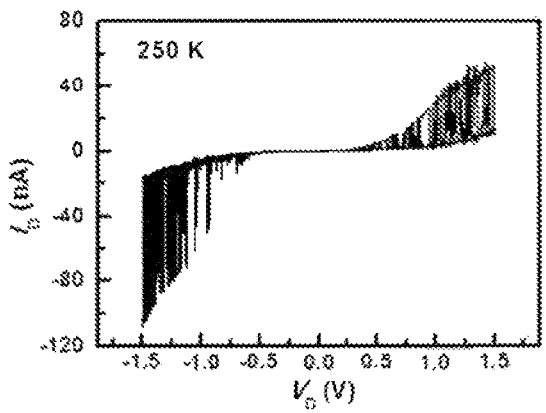
Figure 6E:
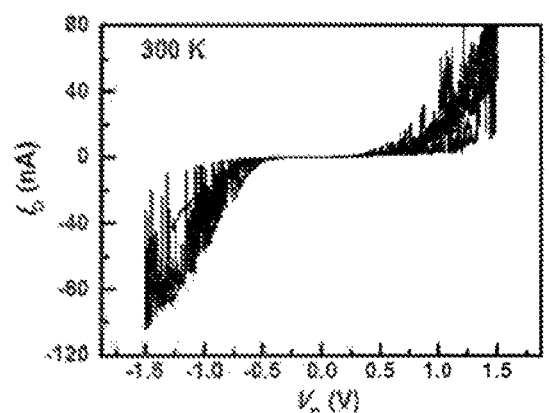
Figure 6F:
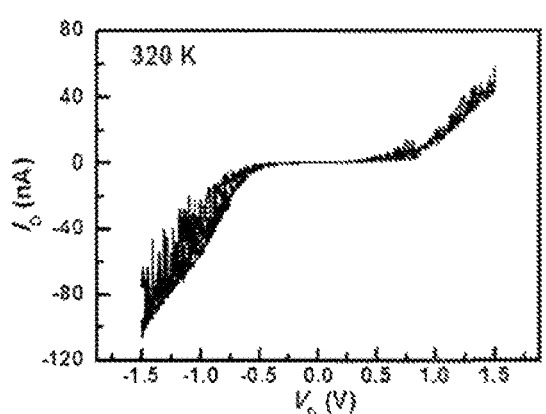

The results are shown in FIG. 5. As can be seen from FIG. 5, under ultraviolet light, the diarylethene compound of Formula I-1 becomes a closed configuration, and conductance of the device is approximately doubled. Under visible light, the diarylethene compound becomes an open configuration and the conductance of the device is reduced to approximately ½ of the conductance of the high conductive state.

Example 3: Synthesis of the Diarylethene Compound of Formula II-1

All reagents and chemicals were obtained commercially and were used without further purification, unless otherwise indicated. All reactions were carried out in a dry solvent and an inert atmosphere of argon using standard Schlenk technology (also known as Chirac technique or double row tube operation technique). $^1H$ and $^{13}C$ NMR spectra were recorded on Variance Mercury plus 300 MHz and Bruker ARX 500 NMR spectrometer. All chemical shifts of $^1H$ were referenced to tetramethylsilane (TMS, δ=0.00 ppm) or $CDCl_3$ (δ=7.26 ppm), and chemical shifts of $^{13}C$ NMR were referenced to $CDCl_3$ (δ=77.00 ppm). Mass spectra were recorded on a Bruker APEX IV mass spectrometer. Elemental analysis was performed by using the Flash EA1112 analyzer.

The synthetic route of the diarylethene compound of Formula II is as follows:

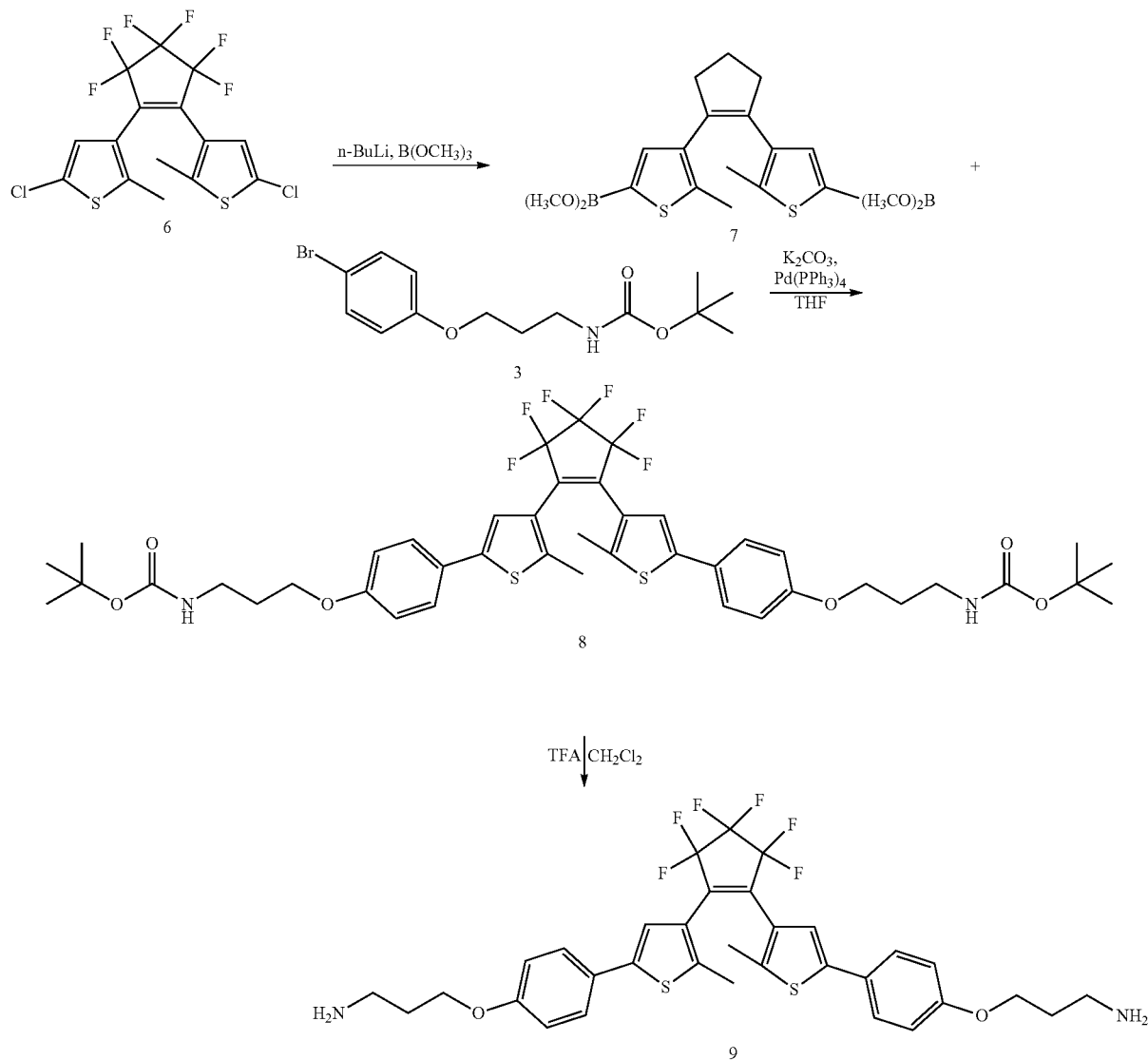

Compound 6 and tert-butyl-3-(4-bromophenoxy)propyl-carbamate (Compound 3) were synthesized according to the method described in the aforementioned literatures. Compound 6 (0.435 g, 1 mmol) was dissolved in 5 mL dry THF. After being stirred for 10 minutes in an ice-salt bath under an argon atmosphere, 2.5 M n-butyl lithium (0.96 mL, 2.4 mmol) was injected slowly, followed by stirring for 45 minutes at room temperature. Then, B(OCH$_3$)$_3$ (0.6 mL, 3 mmol) was added and stirred for further 4 hours to afford compound 7. Thereafter, the reaction mixture was heated up to 60° C. Compound 3 (0.729 g, 2.4 mmol) dissolved in THF/H$_2$O (10 mL/4 mL), Pd(PPh$_3$)$_4$ (83 mg, 0.072 mmol) and K$_2$CO$_3$ (1.0 g, 7.2 mmol) were injected into the reaction mixture and stirred at reflux overnight. After cooling, the reaction mixture was poured into water (50 mL) and extracted with CH$_2$Cl$_2$ (3×30 mL). The combined organic layers were dried over Na$_2$SO$_4$ and solvent was removed under reduced pressure. The crude was purified by chromatography on a silica gel column to afford compound 8 as a yellow solid.

$^1$H NMR (400 MHz, CDCl$_3$, 298 K): δ 7.40 (d, J=8.6 Hz, 4H), 6.92 (s, 2H), 6.88 (d, J=8.7 Hz, 4H), 4.84 (s, 2H), 4.02 (t, J=5.9 Hz, 4H), 3.23 (d, J=6.0 Hz, 4H), 1.95 (s, 6H), 1.45 (s, 18H), 0.89 (dd, J=14.5, 7.7 Hz, 4H). $^{13}$C NMR (100 MHz, CDCl3, 298 K): δ 159.4, 155.9, 136.5, 136.7, 136.0, 135.9, 128.1, 125.3, 122.6, 121.9, 114.9, 107.7, 79.5, 65.8, 38.1, 29.3, 28.4, 15.4. HRMS (TOF-ESI+) (m/z): C$_{43}$H$_{48}$F N$_2$O$_6$S$_2$ calcd for: 867.29 [M+H$^+$]; found: 867.29.

After that, trifluoroacetic acid (1.0 mL, 0.34 g, 3.73 mmol) was added dropwise to compound 8 (0.12 g) in CH$_2$Cl$_2$ (10 mL). After being stirred at room temperature for 2 h, the mixture was added dropwise into saturated NaHCO$_3$ aq. solution (20 mL). Then, the mixture was extracted with CH$_2$Cl$_2$ (50 mL). The organic layer was washed with the saturated NaHCO$_3$ aq. solution (30 mL) and brine (10 mL), and dried over MgSO$_4$. The solvent was evaporated in vacuum to give the target compound 9 (i.e., compound of Formula II-1) as a dark brown solid.

$^1$H NMR (400 MHz, DMSO, ppm): δ 7.90 (s, 4H), 7.47 (d, J=8.6 Hz, 4H), 7.15 (s, 2H), 7.01 (d, J=8.6 Hz, 4H). 4.03 (t, J=5.7 Hz, 4H), 2.96 (t, J=6.9 Hz, 4H), 2.87 (t, J=7.0 Hz, 4H), 1.91 (s, 6H).

$^{13}$C NMR (100 MHz, DMSO, ppm): δ. 159.4, 138.7, 136.7, 136.5, 136.0, 135.9, 135.6, 125.3, 128.1, 122.6, 122.3, 122.1, 119.7, 114.9, 107.7, 72.5, 49.8, 31.0, 15.4. HRMS (MALDI-TOF-ESI+) (m/z): $C_{33}H_{32}F_6N_2O_2S_2$ calcd for: 667.18 [M+H$^+$]; found: 667.18.

Example 4: Preparation of the Diarylethene-Graphene Molecular Junction Device of Formula II-1

A two-dimensional monolayer graphene having a nanogap array was fabricated by using a dash-line lithographic (DLL) method as described in detail in the aforementioned literatures. For molecular reconnection, the diarylethene compound of Formula II-1 was first dissolved in pyridine at a concentration of about $10^{-4}$ M. The solution was then radiated with visible light (>520 nm) to ensure that the diarylethene compound of Formula II-1 was in open configuration. Finally, the graphene devices and 1-ethyl-3-(3-dimethylaminopropyl)carbodiimide hydrochloride (EDCI), a well-known carbodiimide dehydrating/activating agent, were added to the solution of the diarylethene compound of Formula II-1 and reconnected for two days in dark. Thereafter, the reconnected graphene was taken out from the solution, washed with copious acetone and ultrapure water, and dried in $N_2$ gas stream.

Characterization of the Diarylethene-Graphene Molecular Junction Device Prepared in Example 4

(1) Characterization of Switching Characteristics of Light-Controlled Molecular Junction Device The characterization of the molecular junction devices at room temperature was performed by using an Agilent 4155C semiconductor characterization system and a Karl Suss (PM5) manual probe station in ambient atmosphere. Light radiation was performed with a hand-held UV lamp (WFH-2048, Shanghai Tanghui Electronics Co., Ltd.) (~100 µW/cm$^2$, λ=365 nm) and with a monochromatic visible light (~240 µW/cm$^2$, λ=540 nm). The monochromatic light was generated by a grating monochromator with a 150 W halogen incandescent lamp (TLS 1509-150A, Zolix instruments Ltd., Beijing). To avoid heating during radiation, visible light was focused and guided by a long optical fiber up to about 2 cm from the molecular junction device. For typical real-time measurements of switching characteristics of light-controlled molecular junction devices at room temperature, ultraviolet and visible lights were toggled back and forth at standard atmospheric conditions. For the stability measurements, the molecular junction devices were kept in a dark metal box under standard atmospheric conditions for more than a year. Then, the molecular junction devices were taken out and subjected to similar measurements.

Under visible light, the diarylethene compound of Formula II-1 turns to an open configuration, the $I_D$ changes little with $V_D$, and the molecular junction device exhibits a low conductive state. Under ultraviolet light, the diarylethene compound turns to a closed configuration as shown in Formula II-1, the $I_D$ changes largely with $V_D$, and the molecular junction device exhibits a high conductive state. The switching of the whole molecular junction device is reversible and reproducible.

Based on this, an example of the present invention provides a reversible light-controlled molecular switch device, comprising at least the diarylethene-graphene molecular junction device prepared in Example 4 (containing the diarylethene compound represented by Formula II-1 or 11-2). The light-controlled molecular switch device exhibits a high conductive state under ultraviolet light, which is equivalent to switch off; and the light-controlled molecular switch device exhibits a low conductive state under visible light, equivalent to switch on. Accordingly, reversible switching is achieved. Moreover, the reversible light-controlled molecular switch device may further comprise a visible light generating means and an ultraviolet light generating means for radiating the reversible light-controlled molecular switch device with visible light or ultraviolet light. The visible light generating means and the ultraviolet light generating means can be obtained by a skilled person in the art in accordance with the invention herein, without creative work, and are not limited herein. For example, the visible light generating means and the ultraviolet light generating means can utilize a 50 W xenon light source PLS-SXE300/300 UV light source (Beijing Bofeilai Technology Co., Ltd.) and then provide ultraviolet light at 365 nm and visible light at 540 nm using a monochromator.

(2) Characterization of Switching Characteristics of an Electrically-Controlled Molecular Junction Device (Containing the Diarylethene Compound Represented by Formula II-2).

Characterization of temperature-dependent I-V characteristics of the diarylethene-graphene molecular junction devices (the diarylethene compound turns to a closed configuration, i.e., the structure shown in Formula II-2, under UV radiation) was carried out by using an Agilent 4155C semiconductor characterization system and ST-500-probe station (Janis Research Company) with liquid nitrogen and liquid helium cooling. Real-time recording of stochastic switches was performed at a low temperature and in vacuum (pressure of less than 1*10$^{-4}$ Pa).

The following conclusions can be drawn from some results shown in FIG. 6:

(2-1) According to the current-voltage (I-V) curve (as shown in FIG. 6), at a temperature of 100 K to 300 K, the molecular junction device exhibits the characteristics of random switching between the high conductive state and the low conductive state under a source-drain voltage of 0.2 to 1.5 V or a source-drain voltage of −0.2 to −1.5 V.

(2-2) When the temperature is below 100 K, the molecular junction device exhibits a continuously low conductive state; and when the temperature is above 300 K, the molecular junction device exhibits a continuously high conductive state.

(2-3) At a temperature of 100 K to 300 K, when the source-drain voltage is between −0.2 and 0.2 V, the molecular junction device exhibits a low conductive state; when the source-drain voltage is greater than 1.5 V or less than −1.5 V, the molecular junction device exhibits a continuously high conductive state.

Based on the conclusions (2-1), an example of the present invention provides a reversible electrically-controlled molecular switch device, comprising the diarylethene-graphene molecular junction device provided by example 4 of the present invention. The diarylethene compound turns to a closed configuration, i.e., the structure represented by Formula II-2 under UV light. When a voltage ranging from 0.2 V to 1.5 V or ranging from −0.2 V to −1.5 V is supplied across the molecular junction device, the electrically-controlled molecular switch device exhibits random switching state between the high conduction and the low conduction at a temperature of 100 K to 300 K. The switch device has the characteristics of random switching of conductive states, and thus can be used for performing logic operations and the like. In addition, the electrically-controlled molecular switch device may further comprise a voltage generating means connected to the molecular junction device for supplying a voltage ranging from 0.2 V to 1.5 V or a voltage ranging from −0.2 V to −1.5 V across the molecular junction device.

Based on the conclusions (2-2), an example of the present invention provides a reversible temperature-controlled molecular switch device, comprising the diarylethene-graphene molecular junction device provided by example 4 of the present invention. The diarylethene compound turns to a closed configuration, i.e., the structure shown in Formula II-2 under UV light. The temperature-controlled molecular switch device exhibits a low conductive state at a temperature below 100 K, and exhibits a high conductive state at a temperature above 300 K. The temperature-controlled molecular switch device can exhibit different switching characteristics at different temperatures.

At a temperature below 100 K, the temperature-controlled molecular switch device exhibits a low conductive state and only has a very small $I_D$, which is equivalent to switch on. At a temperature above 300 K, the temperature-controlled molecular switch device exhibits a high conductive state and has a large $I_D$, which is equivalent to switch off. Thus, the temperature-controlled molecular switch device can be used as a temperature sensor or a temperature sensitive switch. The temperature-controlled molecular switch device can also comprise a temperature control means for providing a temperature below 100 K or a temperature above 300 K for the temperature-controlled molecular switch device. Thus, the regulation of the temperature-controlled molecular switch device can be achieved by adjusting the temperature.

Based on the conclusions (2-3), the example of the present invention provides another reversible electrically-controlled molecular switch device, comprising the diarylethene-graphene molecular junction device provided by example 4 of the present invention. The diarylethene compound turns to a closed configuration, i.e., the structure represented by Formula II-2 under UV radiation. At a temperature of 100 K to 300 K, when a voltage ranging from −0.2 V to 0.2 V is supplied across the molecular junction device, the electrically-controlled molecular switch device exhibits a low conductive state; and when the molecular junction device is supplied with a voltage of greater than 1.5 V or less than −1.5 V across the device, the device exhibits a high conductive state. That is to say, when the applied bias voltage is a low threshold voltage (~0.2 V to 0.2 V), the electrically-controlled molecular switch device is switched-off (low conductive), and when the bias voltage is a high threshold voltage (greater than 1.5 V or less than −1.5 V), the electrically-controlled molecular switch device is switched-on (high conductive). Further, the electrically-controlled molecular switch device may further comprise a voltage generating means connected to the molecular junction device for supplying a voltage ranging from −0.2 V to 0.2 V, or a voltage of greater than 1.5 V or less than −1.5 V.

It should be noted that the voltage generating means connected to the molecular junction devices in the above switch devices, can be implemented by using the prior art in this field, for example, a lock-in amplifier, preferably an HF2LI lock-in amplifier (Zurich Instruments Ltd.) can be used as the voltage generating means of the switch device mentioned above. The voltage generating means are not limited in the present invention. Those skilled in the art can obtain the voltage generating means according to the description herein and connect it to the molecular junction device, without any creative work.

(3) Characterization of Switching Characteristics of Electrically-Controlled Molecular Junction Device (Containing the Diarylethene Compounds of Formula II-1)

The same characterization method was performed as that of the diarylethene compound molecular junction device shown in Formula I-1, and similar conclusions were obtained as follows:

(2-4) Under a source-drain voltage ranging from 0.9 V to 1.5 V or ranging from −0.9 to −1.5 V, at a temperature of 100 K to 300 K, the molecular junction device exhibits random switching between a high conductive state and a low conductive state.

(2-5) When the temperature is below 100 K, the molecular junction device exhibits a continuously low conductivity state; and when the temperature is above 300 K, the molecular junction device exhibits a continuously high conductive state.

(2-6) At a temperature of 100 K to 300 K, the molecular junction device exhibits a low conductive state under a source-drain voltage ranging from −0.9 V to 0.9 V; and the molecular junction device exhibits a continuously high conductive state under a source-drain voltage of greater than 1.5 V or less than −1.5 V.

Flexible Non-Volatile Organic Memory Transistor Devices Prepared from the Diarylethene Compound of Formula II-1 and Characterization Thereof The flexible substrate and the hafnium oxide dielectric layer of the organic memory tube were prepared by using the method described in detail in the aforementioned literatures. For molecule assembly, after the preparation of the hafnium oxide dielectric layer, the $HfO_2$ surface was activated with an oxygen plasma etcher (RIE) at a power of 30 W for 3 minutes to produce —OH for the self-assembly reaction. The activated substrate was immersed in a THF/ethanol mixed solution containing the diarylethene compound II (concentration: 0.1 mM, THF/ethanol=1:1 (V/V), THF and ethanol were strictly dehydrated) in dark for 24 hours for self-assembly within a glove box under argon. The substrate was taken out, the surface of which was washed with ethanol for three times until no visible particulate impurities was observed. The substrate was annealed at 120° C. on the heating stage for 3 minutes to make the amino anchoring group and the cerium oxide substrate link more firmly. Then, a 30 nm thick of pentacene was vacuum evaporated on the above-mentioned substrate in which the diarylethene monomolecular film was assembled within a thermal evaporator. Finally, a metal electrode was evaporated at a predetermined position of the substrate by thermal evaporation.

Characterization of organic memory transistor devices was performed in ambient atmosphere using an Agilent 4155C semiconductor characterization system and a Karl Suss (PM5) manual probe station at room temperature.

The obtained flexible non-volatile organic memory transistor device uses light at 633 nm as a means for writing information. The light radiation conditions in the specific experiment are as follows: the ultraviolet light source is a hand-held UV lamp (energy density I=100 W cm$^{-2}$, wavelength=365 nm); the white light source is a halogen incandescent lamp (energy density I=30 mW cm$^{-2}$, wavelength >420 nm); the global light source at 633 nm is a 150 W halogen incandescent light source with a 633 nm cut-off light filter.

The characterization of processes of presetting, writing, erasing for the flexible non-volatile organic memory transistor device were as follows. Firstly, ultraviolet light (365 nm) was applied to "preset" the device, so as to allow the device to work as a memory device. After the device was preset, visible light radiation at 633 nm can be used to "write" the information thereto. When the device was radiated with visible light at 633 nm, the source-drain current increases linearly and reaches a high conductive state; and after the radiation was stopped, the high conductive state was continuously maintained. This result demonstrates the non-volatile storage performance of a photoactive hybrid dielectric layer. Visible light radiation (≥520 nm) makes the diarylethene monomolecular film be switched from Off to On, meanwhile make the device be back to the initial electrical state, and therefore it serves as an "erasing" means for the memory device. At the same time, when a negative gate voltage ($V_G$) was applied to the gate, the erasing of information can also be achieved.

A Photo-Responsive Organic Transistor Device Prepared from a Diarylethene Compound Represented by Formula II-1 and Characterization Thereof The substrate and the gold electrode of the organic field-effect transistor with a bottom gate bottom contact structure were prepared by using the method described in detail in the aforementioned literatures. For molecule assembly, the surface of the prepared gold electrode was washed with ethanol, and then etched by an oxygen plasma etcher (RIE) at a power of 30 W for 5 minutes to clean the organic substances adsorbed thereon. The cleaned substrate containing the patterned gold electrode pair was immersed in an ethanol solution of the diarylethene compound represented by Formula II-1 (concentration: $10^{-4}$ mol/L) for 24 hours in dark under the protection of Ar gas. The substrate was taken out, the surface of which was washed with ethanol for three times. The substrate was annealed at 120° C. on the heating stage for 3 minutes. Finally, a 40 nm thick of pentacene was vacuum evaporated on the above-mentioned substrate in which the diarylethene monomolecular film was assembled within a thermal evaporator.

The characterization of the photo-responsive organic field-effect transistor was performed at room temperature in ambient atmosphere using an Agilent 4155C semiconductor characterization system and a Karl Suss (PM5) manual probe station. Light radiation was performed with a hand-held UV lamp (WFH-2048, Shanghai Tanghui Electronics Co., Ltd.) (~100 μW/cm², λ=365 nm) and with a monochromatic visible light (~240 μW/cm², λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device. For typical real-time measurements of switching characteristics of the photo-responsive organic field-effect transistor at room temperature, ultraviolet and visible lights were toggled back and forth at standard atmospheric conditions.

The results show that the diarylethene compound becomes a closed configuration under ultraviolet light, and conductance of the device is approximately doubled. Under visible light, the diarylethene compound becomes an open configuration and the conductance of the device is reduced to approximately ½ of the conductance of the high conductive state.

Example 5: Synthesis of the Diarylethene Compound of Formula III-1

All reagents and chemicals were obtained commercially and were used without further purification, unless otherwise indicated. All reactions were carried out in a dry solvent and an inert atmosphere of argon using standard Schlenk technology (also known as Chirac technique or double row tube operation technique). $^1$H and $^{13}$C NMR spectra were recorded on Variance Mercury plus 300 MHz and Bruker ARX 500 NMR spectrometer. All chemical shifts of $^1$H were referenced to tetramethylsilane (TMS, δ=0.00 ppm) or CDCl$_3$ (δ=7.26 ppm), and chemical shifts of $^{13}$C NMR were referenced to CDCl$_3$ (δ=77.00 ppm). Mass spectra were recorded on a Bruker APEX IV mass spectrometer. Elemental analysis was performed by using the Flash EA1112 analyzer.

The synthetic route of the diarylethene compound of Formula III-1 is as follows:

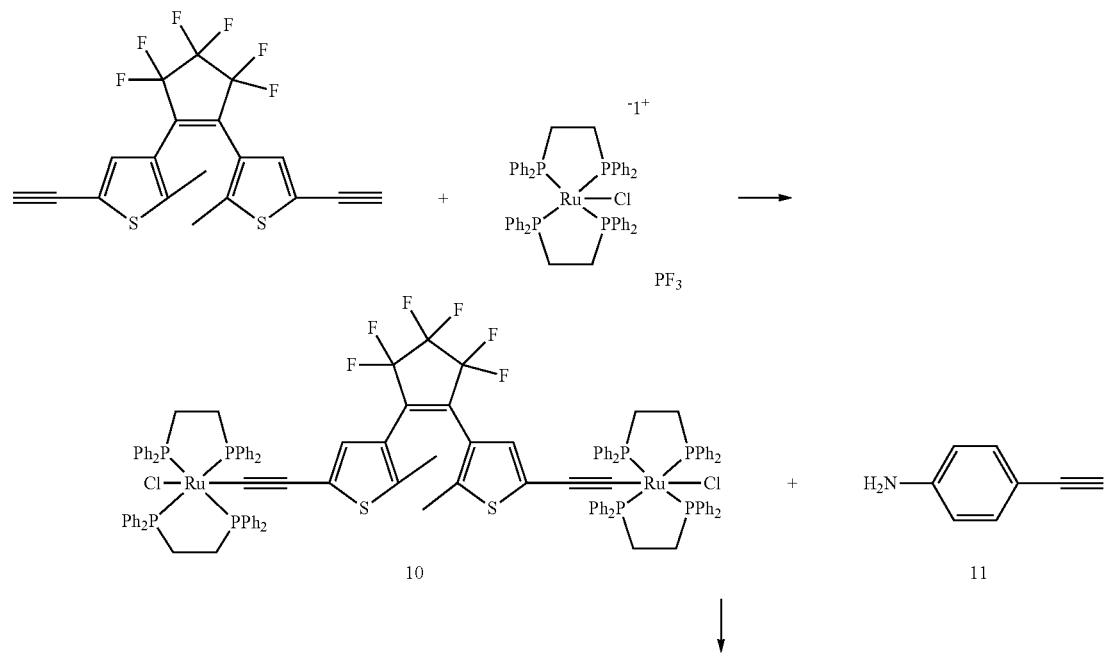

-continued

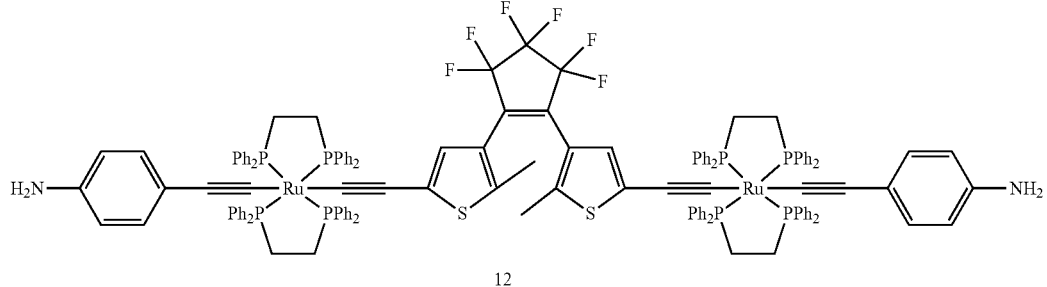

12

Compound 10 was synthesized according to the method described in the literature (F, Meng et al., 2012). Compound 10 (200 mg, 0.17 mol), compound 11 (200 mg, 0.17 mol), NaPF$_6$ (57 mg, 0.34 mmol) and triethylamine (0.12 mL, 0.85 mmol) were dissolved in 20 mL of dry dichloromethane. The mixture was stirred for 4 days in dark under an argon atmosphere. Then the solvent was evaporated. The mixture was dissolved in 40 mL of dichloromethane, and then extracted with aqueous solution of potassium carbonate (3×15 mL) and distilled water (2×10 mL) successively. The organic phase was then dried over Na$_2$SO$_4$. Dichloromethane was removed by evaporation and the crude was extracted with pentane (3×10 mL) and dried over Na$_2$SO$_4$ to afford compound 12 (i.e., compound of Formula III-1) as a green solid.

IR (KBr): $\tilde{v}$=2052 (C≡C) cm$^{-1}$. $^1$H NMR (CD$_3$SOCD$_3$): δ 239 (s, 3H), 4.25 (s, 2H), 7.07-7.27 (m, 32H), 7.57 (m, 4H), 7.69 (m, 4H), 7.84 (d, J=7.6 Hz, 2H), 9.22 (d, J=5.6 Hz, 2H) ppm. $^{31}$P NMR (CD$_3$SOCD$_3$): β 51.58 (s) ppm: HR-MS FAB+ (m/z); 2412.4166 ([M+], calcd for 2412.4254).

Example 6: Preparation of a Diarylethene-Graphene Molecular Junction Device Represented by Formula III-1

A two-dimensional monolayer graphene having a nanogap array was fabricated by using a dash-line lithographic (DLL) method as described in detail in the aforementioned literatures. For molecular reconnection, the diarylethene compound of Formula III-1 was first dissolved in pyridine at a concentration of about 10$^{-4}$ M. The solution was then radiated with visible light (>520 nm) such that the diarylethene compound of Formula III-1 was in open configuration. Finally, the graphene and 1-ethyl-3-(3-dimethylaminopropyl)carbodiimide hydrochloride (EDCI), a well-known carbodiimide dehydrating/activating agent, were added to the solution of the diarylethene compound of Formula III-1 for reconnection for two days in dark. Thereafter, the reconnected graphene was taken out from the solution, washed with copious acetone and ultrapure water, and dried in N$_2$ gas stream.

Characterization of Diarylethene-Graphene Molecular Junction Device Prepared in Example 6
(1) Characterization of Switching Characteristics of Light-Controlled Molecular Junction Device The characterization of the molecular junction devices at room temperature was performed using an Agilent 4155C semiconductor characterization system and a Karl Suss (PM5) manual probe station in ambient atmosphere. Light radiation was performed with a hand-held UV lamp (WFH-2048, Shanghai Tanghui Electronics Co., Ltd.) (100 μW/cm$^2$, λ=365 nm) and with a monochromatic visible light (240 μW/cm$^2$, λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device.

For typical real-time measurements of switching characteristics of light-controlled molecular junction device at room temperature, ultraviolet and visible lights were toggled back and forth at standard atmospheric conditions. For the stability measurements, the molecular junction device was kept in a dark metal box under standard atmospheric conditions for more than a year. Then, the molecular junction device was taken out and subjected to similar measurements.

Under visible light, the diarylethene compound of Formula III-1 turns to an open configuration, the I$_D$ changes little with V$_D$, and the molecular junction device exhibits a low conductive state. Under ultraviolet light, the diarylethene compound turns to a closed configuration, the I$_D$ changes largely with V$_D$, and the molecular junction device exhibits a high conductive state. The switching of the whole molecular junction device is reversible and reproducible.

Based on this, an example of the present invention provides a reversible light-controlled molecular switch device comprising at least the diarylethene-graphene molecular junction device prepared in Example 6 (containing the diarylethene compound represented by Formula III-1 or III-2). The light-controlled molecular switch device exhibits a high conductive state under ultraviolet light, which is equivalent to switch on; and the light-controlled molecular switch device exhibits a low conductive state under visible light, which is equivalent to switch off. Accordingly, reversible switching is achieved. Moreover, the reversible light-controlled molecular switch device may further comprise a visible light generating means and an ultraviolet light generating means for radiating the reversible light-controlled molecular switch device with visible light or ultraviolet light. The visible light generating means and the ultraviolet light generating means can be obtained by a skilled person in the art in accordance with the invention herein, without any creative work, and are not limited herein. For example, the visible light generating means and the ultraviolet light generating means can utilize a 50 W xenon light source PLS-SXE300/300 UV light source (Beijing Bofeilai Technology Co., Ltd.) and then provide ultraviolet light at 365 nm and visible light at 540 nm using a monochromator.

(2) Characterization of Switching Characteristics of an Electrically-Controlled Molecular Junction Device (Containing the Diarylethene Compound of Formula III-2).

Characterization of temperature-dependent I-V characteristics of the diarylethene-graphene molecular junction devices (the diarylethene compound turns to a closed configuration, i.e., the structure shown in Formula III-2, under UV radiation) was carried out by using an Agilent 4155C semiconductor characterization system and ST-500-probe station (Janis Research Company) with liquid nitrogen and liquid helium cooling. Real-time recording of random switches was performed at a low temperature and in vacuum (pressure of less than $1*10^{-4}$ Pa).

The following conclusions can be drawn:

(3-1) According to the current-voltage (I-V) curve, at a temperature of 100 K to 300 K, the molecular junction device exhibits the characteristics of random switching between the high and low conductive states under a source-drain voltage ranging from 0.2 V to 1.5 V or ranging from −0.2 V to −1.5 V.

(3-2) When the temperature is below 100 K, the molecular junction device exhibits a continuously low conductive state; and when the temperature is above 300 K, the molecular junction device exhibits a continuously high conductive state.

(3-3) At a temperature of 100 K to 300 K, when the source-drain voltage is between −0.2 and 0.2 V, the molecular junction device exhibits a low conductive state; when the source-drain voltage is greater than 1.5 V or less than −1.5 V, the molecular junction device exhibits a continuously high conductive state.

Based on the conclusions (3-1), an example of the present invention provides a reversible electrically-controlled molecular switch device, comprising the diarylethene-graphene molecular junction device provided by example 6 of the present invention. The diarylethene compound turns to a closed configuration, i.e., the structure represented by Formula III-2 under UV light.

When a voltage ranging from 0.2 V to 1.5 V or ranging from −0.2 V to −1.5 V is supplied across the molecular junction device, the electrically-controlled molecular switch device exhibits random switching state between the high conduction and the low conduction at a temperature of 100 K to 300 K. The switch device has the characteristics of random switching of conductive states, and thus can be used for performing logic operations and the like. In addition, the electrically-controlled molecular switch device may further comprise a voltage generating means connected to the molecular junction device for supplying a voltage ranging from 0.2 V to 1.5 V or a voltage ranging from −0.2 V to −1.5 V across the molecular junction device.

Based on the conclusions (3-2), an example of the present invention provides a reversible temperature-controlled molecular switch device, comprising the diarylethene-graphene molecular junction device provided by example 6 of the present invention. The diarylethene compound turns to a closed configuration, i.e., the structure shown in Formula III-2 under UV light. When the molecular junction device is supplied with a voltage ranging from 0.2 V to 1.5 V or ranging from −0.2 V to −1.5 V across the molecular junction device, the temperature-controlled molecular switch device exhibits a low conductive state at a temperature below 100 K, and exhibits a high conductive state at a temperature above 300 K. Moreover, The temperature-controlled molecular switch device also comprises a voltage generating means connected to the molecular junction device for supplying a voltage ranging from 0.2 V to 1.5 V or ranging from −0.2 V to −1.5 V. The temperature-controlled molecular switch device can exhibit different switching characteristics at different temperatures.

When the temperature is below 100 K, the temperature-controlled molecular switch device exhibits a low conductive state and only has a very small $I_D$, which is equivalent to switch off; and when the temperature is above 300 K, the temperature-controlled molecular switch device exhibits a high conductive state and has a large $I_D$, which is equivalent to switch on. Thus, the temperature-controlled molecular switch device can be used as a temperature sensor or a temperature sensitive switch. The temperature-controlled molecular switch device can also comprise a temperature control means for providing a temperature below 100 K or a temperature above 300 K to the device. Thus, the regulation of the temperature-controlled molecular switch device can be achieved by adjusting the temperature.

Based on the conclusions (3-3), the example of the present invention provides another reversible electrically-controlled molecular switch device, comprising the diarylethene-graphene molecular junction device supplied by example 6 of the present invention. The diarylethene compound turns to a closed configuration, i.e., the structure represented by Formula III-2 under UV radiation. At a temperature of 100 K to 300 K, when a voltage ranging from −0.2 V to 0.2 V is supplied across the molecular junction device, the electrically-controlled molecular switch device exhibits a low conductive state; and when the molecular junction device is supplied with a voltage of greater than 1.5 V or less than −1.5 V across the device, the device exhibits a high conductive state. That is to say, when the applied bias voltage is a low threshold voltage (−0.2 V to 0.2 V), the electrically-controlled molecular switch device is switched-off (low conductive), and when the bias voltage is a high threshold voltage (greater than 1.5 V or less than −1.5 V), the electrically-controlled molecular switch device is switched-on (high conductive). Further, the electrically-controlled molecular switch device may further comprise a voltage generating means connected to the molecular junction device for supplying a voltage ranging from −0.2 V to 0.2 V, or a voltage of greater than 1.5 V or less than −1.5 V.

It should be noted that the voltage generating means connected to the molecular junction devices in the above switch devices, can be implemented by using the prior art in this field, for example, a lock-in amplifier, preferably an HF2LI lock-in amplifier (Zurich Instruments Ltd.) can be used as the voltage generating means of the switch device mentioned above. The voltage generating means are not limited in the present invention. Those skilled in the art can obtain the voltage generating means according to the description herein and connect it to the molecular junction device, without any creative work.

(3) Characterization of Switching Characteristics of Electrically-Controlled Molecular Junction Device (Containing the Diarylethene Compounds of Formula III-1)

The same characterization method was performed as that of the diarylethene compound molecular junction device shown in Formula II-1, and similar conclusions were obtained as follows:

Flexible Non-Volatile Organic Memory Transistor Devices Prepared from the Diarylethene Compound of Formula III-1 and Characterization Thereof The flexible substrate and the hafnium oxide dielectric layer of the organic memory tube were prepared by using the method described in detail in the aforementioned literatures. For molecule assembly, after the preparation of the hafnium oxide dielectric layer, the $HfO_2$ surface was activated with an oxygen plasma etcher (RIE) at a power of 30 W for 3 minutes to produce —OH for the self-assembly reaction. The activated substrate was immersed in a THF/ethanol mixed solution containing the diarylethene compound III (concentration: 0.1 mM, THF/ethanol=1:1 (V/V), THF and ethanol were strictly dehydrated) in dark for 24 hours for self-assembly within a glove box under argon. The substrate was taken out, the surface of which was washed with ethanol for three times until no visible particulate impurities was observed. The substrate was annealed at 120° C. on the heating stage for 3 minutes to make the amino anchoring group and the cerium oxide substrate link more firmly. Then, a 30 nm thick of pentacene was vacuum evaporated on the above-mentioned substrate in which the diarylethene monomolecular film was assembled within a thermal evaporater. Finally, a metal electrode was evaporated at a predetermined position of the substrate by thermal evaporation.

Characterization of organic memory transistor devices was performed in ambient atmosphere using an Agilent 4155C semiconductor characterization system and a Karl Suss (PM5) manual probe station at room temperature.

The obtained flexible non-volatile organic memory transistor device uses light at 633 nm as a means for writing information. The light radiation conditions in the specific experiment are as follows: the ultraviolet light source is a hand-held UV lamp (energy density I=100 W cm$^{-2}$, wavelength=365 nm); the white light source is a halogen incandescent lamp (energy density I=30 mW cm$^{-2}$, wavelength >420 nm); the global light source at 633 nm is a 150 W halogen incandescent light source with a 633 nm cut-off light filter.

The characterization of processes of presetting, writing, erasing for the flexible non-volatile organic memory transistor device were as follows. Firstly, ultraviolet light (365 nm) was applied to "preset" the device, so as to allow the device to work as a memory device. After the device was preset, visible light radiation at 633 nm can be used to "write" the information thereto. When the device was radiated with visible light at 633 nm, the source-drain current increases linearly and reaches a high conductive state; and after the radiation was stopped, the high conductive state was continuously maintained. This result demonstrates the non-volatile storage performance of a photoactive hybrid dielectric layer. Visible light radiation (≥520 nm) makes the diarylethene monomolecular film be switched from Off to On, meanwhile make the device be back to the initial electrical state, and therefore it serves as an "erasing" means for the memory device. At the same time, when a negative gate voltage (V$_G$) was applied to the gate, the erasing of information can also be achieved.

A Photo-Responsive Organic Transistor Device Prepared from a Diarylethene Compound Represented by Formula III-1 and Characterization Thereof The substrate and the gold electrode of the organic field-effect transistor with a bottom gate bottom contact structure were prepared by using the method described in detail in the aforementioned literatures. For molecule assembly, the surface of the prepared gold electrode was washed with ethanol, and then etched by an oxygen plasma etcher (RIE) at a power of 30 W for 5 minutes to clean the organic substances adsorbed thereon. The cleaned substrate containing the patterned gold electrode pair was immersed in an ethanol solution of the diarylethene compound represented by Formula III-1 (concentration: 10$^{-4}$ mol/L) for 24 hours in dark under the protection of Ar gas. The substrate was taken out, the surface of which was washed with ethanol for three times. The substrate was annealed at 80° C. on the heating stage for 3 minutes. Finally, a 40 nm thick of pentacene was vacuum evaporated on the above-mentioned substrate in which the diarylethene monomolecular film was assembled within a thermal evaporater.

The characterization of the photo-responsive organic field-effect transistor was performed at room temperature in ambient atmosphere using an Agilent 4155C semiconductor characterization system and a Karl Suss (PM5) manual probe station. Light radiation was performed with a hand-held UV lamp (WFH-2048, Shanghai Tanghui Electronics Co., Ltd.) (~100 μW/cm$^2$, λ=365 nm) and with a monochromatic visible light (~240 μW/cm$^2$, λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device. For typical real-time measurements of switching characteristics of the photo-responsive organic field-effect transistor at room temperature, ultraviolet and visible lights were toggled back and forth at standard atmospheric conditions.

The results show that the diarylethene compound becomes a closed configuration under ultraviolet light, and conductance of the device is approximately doubled. Under visible light, the diarylethene compound becomes an open configuration and the conductance of the device is reduced to approximately ½ of the conductance of the high conductive state.

Example 7: Synthesis of the Azobenzene Compound of Formula IV-1

All reagents and chemicals were obtained commercially and were used without further purification, unless otherwise indicated. All reactions were carried out in a dry solvent and an inert atmosphere of argon using standard Schlenk technology (also known as Chirac technique or double row tube operation technique). $^1$H and $^{13}$C NMR spectra were recorded on Variance Mercury plus 300 MHz and Bruker ARX 500 NMR spectrometer. All chemical shifts of $^1$H were referenced to tetramethylsilane (TMS, δ=0.00 ppm) or CDCl$_3$ (δ=7.26 ppm), and chemical shifts of $^{13}$C NMR were referenced to CDCl$_3$ (δ=77.00 ppm). Mass spectra were recorded on a Bruker APEX IV mass spectrometer. Elemental analysis was performed by using the Flash EA1112 analyzer.

The synthetic route of the azobenzene compound of Formula IV-1 is as follows:

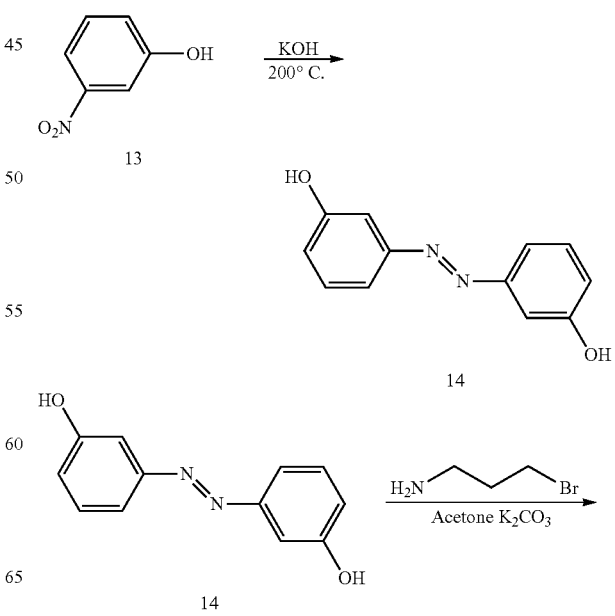

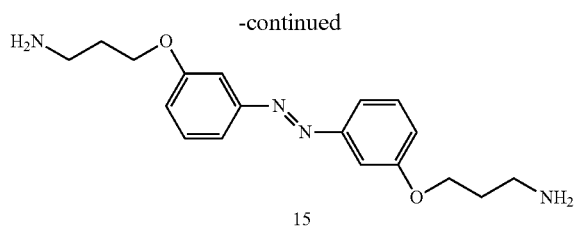

1 g (7.2 mmol) of compound 13 and 1.2 g (21.4 mmol) of KOH were refluxed overnight in ethanol solution. The product was only extracted with dichloromethane, washed three times with saturated brine, and then purified by column chromatography to afford compound 14, 0.615 g (80%).

$^1$H NMR (400 MHz, CDCl$_3$, 298 K) δ 7.56 (d, J=7.4 Hz, 2H), δ 7.50 (d, J=7.4 Hz, 2H), δ 7.33 (q, J=7.5 Hz, 2H), δ 7.15 (d, J=7.4 Hz, 2H), δ 5.35 (s, 2H). $^{13}$C NMR (100 MHz, CDCl$_3$, 298 K) 6158.8, 154.1, 130.4, 118.1, 115.6, 110.6. HRMS (TOF-ESI+) (m/z): C$_{12}$H$_{10}$N$_2$O$_2$, calcd for 215.07 [M+H$^+$], found 215.07.

Compound 14 (0.5 g, 2.3 mmol), 3-bromopropylamine (1.9 g, 13.87 mmol) and potassium carbonate (3.6 g) were combined in acetone and refluxed overnight. Acetone was removed by vacuum, then the product was extracted with dichloromethane, and washed with saturated brine for three times, and then purified by column chromatography to afford compound 15 (the compound of Formula IV-1) as an orange solid, 0.755 g (100%).

$^1$H NMR (400 MHz, CDCl$_3$, 298 K) δ 7.56 (d, J=7.4 Hz, 2H), δ 7.50 (d, J=7.4 Hz, 2H), δ 7.33 (q, J=7.5 Hz, 2H), 67.15 (d, J=7.4 Hz, 2H), δ 5.11 (s, 4H), δ 4.06 (d, J=1.37, 4H), δ 2.65 (d, J=1.4, 4 H), δ 1.98 (m, 4H). $^{13}$C NMR (100 MHz, CDCl$_3$, 298 K) δ 157.3, 153.3, 129.8, 114.6, 111.5, 109.2, 72.5, 49.8, 31.0. HRMS (TOF-ESI+) (m/z): C$_{18}$H$_{24}$N$_4$O$_2$, calcd for 329.19 [M+H$^+$], found 329.15.

Example 8: Preparation of the Azobenzene-Graphene Molecular Junction Device of Formula IV-1

A two-dimensional monolayer graphene having a nanogap array was fabricated by using a dash-line lithographic (DLL) method as described in detail in the aforementioned literatures. For molecular reconnection, the azobenzene compound of Formula IV-1 was first dissolved in pyridine at a concentration of about 10$^{-4}$ M. The solution was then radiated with visible light (>520 nm) such that the azobenzene compound of Formula IV-1 was in trans-conformation. Finally, graphene and carbodiimide dehydrating agent-activator 1-ethyl-3-(3-dimethylaminopropyl)carbodiimide hydrochloride (EDCI) were added to the solution of the azobenzene compound of Formula IV-1, and reconnected in dark for two days. Thereafter, the reconnected graphene was taken out from the solution, washed with copious acetone and ultrapure water, and dried in N$_2$ gas stream.

Characterization of the Azobenzene-Graphene Molecular Junction Device Prepared in Example 8

(1) Characterization of Switching Characteristics of Light-Controlled Molecular Junction Devices The characterization of the molecular junction devices at room temperature was performed using an Agilent 4155C semiconductor characterization system and a Karl Suss (PM5) manual probe station in ambient atmosphere. Light radiation was performed with a hand-held UV lamp (WFH-2048, Shanghai Tanghui Electronics Co., Ltd.) (~100 μW/cm$^2$, λ=365 nm) and with a monochromatic visible light (~240 μW/cm$^2$, λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device.

For typical real-time measurements of switching characteristics of light-controlled molecular junction device at room temperature, ultraviolet and visible lights were toggled back and forth at standard atmospheric conditions. For the stability measurements, the molecular junction device was kept in a dark metal box under standard atmospheric conditions for more than a year. Then, the molecular junction device was taken out and subjected to similar measurements.

The azobenzene compound represented by Formula IV-1 is in trans-conformation under visible light, the I$_D$ changes with V$_D$, which is equivalent to that the molecular junction device exhibits a high conductive state. Under ultraviolet light, the azobenzene compound is in cis-conformation, the I$_D$ changes little with V$_D$, I$_D$ value always being around 0 nA, which is equivalent to that the molecular junction device exhibits a low conductive state. The switching of the whole molecular junction device is reversible and reproducible.

Based on this, an example of the present invention provides a reversible light-controlled molecular switch device comprising at least the azobenzene-graphene molecular junction device prepared in Example 8 (containing the azobenzene compound of Formula IV-1 or Formula IV-2). The light-controlled molecular switch device exhibits a high conductive state under visible light, equivalent to switch on; and the light-controlled molecular switch device exhibits a low conductive state under ultraviolet light, equivalent to switch off. Accordingly, reversible switching is achieved. Moreover, the reversible light-controlled molecular switch device may further comprise a visible light generating means and an ultraviolet light generating means for radiating the reversible light-controlled molecular switch device with visible light or ultraviolet light. The visible light generating means and the ultraviolet light generating means can be obtained by a skilled person in the art in accordance with the invention herein, without any creative work, and are not limited herein. For example, the visible light generating means and the ultraviolet light generating means can utilize a 50 W xenon light source PLS-SXE300/300 UV light source (Beijing Bofeilai Technology Co., Ltd.) and then provide ultraviolet light at 365 nm and visible light at 540 nm using a monochromator.

(2) Characterization of Switching Characteristics of an Electrically-Controlled Molecular Junction Device (Containing the Azobenzene Compound of Formula IV-1)

Characterization of temperature-dependent I-V characteristics of the azobenzene-graphene molecular junction devices (the azobenzene compound turns to a trans-conformation under visible light radiation) was carried out by using an Agilent 4155C semiconductor characterization system and ST-500-probe station (Janis Research Company) with liquid nitrogen and liquid helium cooling. Real-time recording of random switching was performed at a low temperature and in vacuum (at a pressure of less than 1*10$^{-4}$ Pa).

The following conclusions can be drawn from the above results:

(4-1) At the temperature of 100 K to 300 K, the molecular junction device exhibits the characteristics of random switching between a high conductive state and a low conductive state under a source-drain voltage ranging from 0.2 V to 1.5 V or ranging from −0.2 V to −1.5 V.

(4-2) When the temperature is below 100 K, the molecular junction device exhibits a continuously low conductive state, and when the temperature is above 300 K, the molecular junction device exhibits a continuously high conductive state.

(4-3) At a temperature of 100 K to 300 K, the molecular junction device exhibits a low conductive state under a source-drain voltage ranging from −0.2 V and 0.2 V; and the molecular junction device exhibits a continuously high conductivity state under a source-drain voltage of greater than 1.5 V or less than −1.5 V.

Based on the conclusion (4-1), an example of the present invention provides a reversible electrically-controlled molecular switch device, comprising the azobenzene-graphene molecular junction device provided by example 8 of the present invention. The azobenzene compound is in trans-conformation, i.e., the structure represented by Formula IV-1 under visible light. When a voltage ranging from 0.2 V to 1.5 V or ranging from −0.2 V to −1.5 V is supplied across the molecular junction device, and the electrically-controlled molecular switch device exhibits random switching between a high conductive state and a low conductive state at a temperature of 100 K to 300 K. The switch device has the characteristics of random switching of conductive states, and thus can be used for performing logic operations and the like. In addition, the electrically-controlled molecular switch device may further comprise a voltage generating means connected to the molecular junction device for supplying a voltage ranging from 0.2 V to 1.5 V or ranging from −0.2 V to −1.5 V across the molecular junction device.

Based on the conclusion (4-2), an example of the present invention provides a reversible temperature-controlled molecular switch device, comprising the azobenzene-graphene molecular junction device provided by example 8 of the present invention. The azobenzene compound is in trans-conformation, i.e., the structure represented by Formula IV-1 under visible light. The temperature-controlled molecular switch device exhibits a low conductive state at a temperature below 100 K; and the temperature-controlled molecular switch device exhibits a high conductive state at a temperature above 300 K. The temperature-controlled molecular switch device can exhibit different switching characteristics at different temperatures. When the temperature is below 300 K, the temperature-controlled molecular switch device exhibits a low conductive state, and only has a very small $I_D$, equivalent to switch off; and when the temperature is above 300 K, the temperature-controlled molecular switch device exhibits a high conductive state, and has a large $I_D$, equivalent to switch on. Thus, the temperature-controlled molecular switch device can be used as a temperature sensor or a temperature sensitive switch.

The temperature-controlled molecular switch device can also comprise a temperature control means for providing a temperature below 100 K or a temperature above 300 K to the temperature-controlled molecular switch device. Thus, the regulation of the temperature-controlled molecular switch device can be achieved by adjusting the temperature.

Based on the conclusion (4-3), an example of the present invention provides another reversible electrically-controlled molecular switch device, comprising the azobenzene-graphene molecular junction device provided by example 8 of the present invention. The azobenzene compound is in trans-conformation, i.e., the structure represented by Formula IV-1 under visible light. At a temperature of 100 K to 300 K, when a voltage of −0.2 V to 0.2 V is supplied across the molecular junction device, the electrically-controlled molecular switch device exhibits a low conductive state; and the device exhibits a high conductive state when a voltage of greater than 1.5 V or less than −1.5 V is applied across the molecular junction device. That is to say, when the applied bias voltage is a low threshold voltage (~0.2 V to 0.2 V), the electrically-controlled molecular switch device is switched-off (low conductive); and when the bias voltage is at a high threshold voltage (greater than 1.5 V or less than −1.5 V), the electrically-controlled molecular switch device is switched-on (high conductive). Further, the electrically-controlled molecular switch device may further comprise a voltage generating means connected to the molecular junction device, for supplying a voltage ranging from −0.2 V to 0.2 V, or a voltage of greater than 1.5 V or less than −1.5 V across the molecular junction device.

It should be noted that the voltage generating means connected to the molecular junction devices in the above switch devices, can be implemented by using the prior art in this field, for example, a lock-in amplifier, preferably an HF2LI lock-in amplifier (Zurich Instruments Ltd.) can be used as the voltage generating means of the switch device mentioned above. The voltage generating means are not limited in the present invention. Those skilled in the art can obtain the voltage generating means according to the description herein and connect it to the molecular junction device, without any creative work.

(3) Characterization of Switching Characteristics of the Electrically-Controlled Molecular Junction Devices (Containing the Azobenzene Compound of Formula IV-2)

The same characterization method was performed as that of the diarylethene compound molecular junction device of Formula II-1, and the same conclusion as the diarylethene compound molecular junction device of Formula II-1 was obtained. The invention will not be described in details herein, and the above description may be referred to.

Flexible Non-Volatile Organic Memory Transistor Devices Prepared from the Azobenzene Compound of Formula IV-1 and Characterization Thereof The flexible substrate and the hafnium oxide dielectric layer of the organic memory tube were prepared by using the method described in detail in the aforementioned literatures. For molecule assembly, after the preparation of the hafnium oxide dielectric layer, the $HfO_2$ surface was activated with an oxygen plasma etcher (RIE) at a power of 30 W for 3 minutes to produce —OH for the self-assembly reaction. The activated substrate was immersed in a THF/ethanol mixed solution containing the azobenzene compound IV (concentration: 0.1 mM, THF/ethanol=1:1 (V/V), THF and ethanol were strictly dehydrated) in dark for 24 hours for self-assembly within a glove box under argon. The substrate was taken out, the surface of which was washed with ethanol for three times until no visible particulate impurities was observed. The substrate was annealed at 120° C. on the heating stage for 3 minutes to make the amino anchoring group and the cerium oxide substrate link more firmly. Then, a 30 nm thick of pentacene was vacuum evaporated on the above-mentioned substrate in which the azobenzene monomolecular film was assembled within a thermal evaporater. Finally, a metal electrode was evaporated at a predetermined position of the substrate by thermal evaporation.

Characterization of organic memory transistor devices was performed in ambient atmosphere using an Agilent 4155C semiconductor characterization system and a Karl Suss (PM5) manual probe station at room temperature.

The obtained flexible non-volatile organic memory transistor device uses light at 633 nm as a means for writing information. The light radiation conditions in the specific experiment are as follows: the ultraviolet light source is a hand-held UV lamp (energy density I=100 W cm$^{-2}$, wavelength=365 nm); the white light source is a halogen incandescent lamp (energy density I=30 mW cm$^{-2}$, wavelength >420 nm); the global light source at 633 nm is a 150 W halogen incandescent light source with a 633 nm cut-off light filter.

The characterization of processes of presetting, writing, erasing for the flexible non-volatile organic memory transistor device were as follows. Firstly, ultraviolet light (365 nm) was applied to "preset" the device, so as to allow the device to work as a memory device. After the device was preset, visible light radiation at 633 nm can be used to "write" the information thereto. When the device was radiated with visible light at 633 nm, the source-drain current increases linearly and reaches a high conductive state; and after the radiation was stopped, the high conductive state was continuously maintained. This result demonstrates the non-volatile storage performance of a photoactive hybrid dielectric layer. Visible light radiation (≥520 nm) makes the azobenzene monomolecular film turn to trans-conformation from cis-conformation, meanwhile make the device be back to the initial electrical state, and therefore it serves as an "erasing" means for the memory device. At the same time, when a negative gate voltage ($V_G$) was applied to the gate, the erasing of information can also be achieved.

A Photo-Responsive Organic Transistor Device Prepared from the Azobenzene Compound of Formula IV-1 and Characterization Thereof The substrate and the gold electrode of the organic field-effect transistor with a bottom gate bottom contact structure were prepared by using the method described in detail in the aforementioned literatures. For molecule assembly, the surface of the prepared gold electrode was washed with ethanol, and then etched by an oxygen plasma etcher (RIE) at a power of 30 W for 5 minutes to clean the organic substances adsorbed thereon. The cleaned substrate containing the patterned gold electrode pair was immersed in an ethanol solution of the azobenzene compound represented by Formula IV-1 (concentration: 10$^{-4}$ mol/L) for 24 hours in dark under the protection of Ar gas. The substrate was taken out, the surface of which was washed with ethanol for three times. The substrate was annealed at 60° C. on the heating stage for 5 minutes. Finally, a 50 nm thick of pentacene was vacuum evaporated on the above-mentioned substrate in which the azobenzene monomolecular film was assembled within a thermal evaporater.

The characterization of the photo-responsive organic field-effect transistor was performed at room temperature in ambient atmosphere using an Agilent 4155C semiconductor characterization system and a Karl Suss (PM5) manual probe station. Light radiation was performed with a hand-held UV lamp (WFH-2048, Shanghai Tanghui Electronics Co., Ltd.) (~100 μW/cm$^2$, λ=365 nm) and with a monochromatic visible light (~240 μW/cm$^2$, λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device. For typical real-time measurements of switching characteristics of the photo-responsive organic field-effect transistor at room temperature, ultraviolet and visible lights were toggled back and forth at standard atmospheric conditions.

The results show that the azobenzene compound becomes a cis-transformation under ultraviolet light, and conductance of the device is approximately doubled. Under visible light, the azobenzene compound becomes a trans-transformation and the conductance of the device is reduced to approximately ½ of the conductance of the high conductive state.

Example 9: Synthesis of the Spiropyrane Compound of Formula V-1

All reagents and chemicals were obtained commercially and were used without further purification, unless otherwise indicated. All reactions were carried out in a dry solvent and an inert atmosphere of argon using standard Schlenk technology (also known as Chirac technique or double row tube operation technique). $^1$H and $^{13}$C NMR spectra were recorded on Variance Mercury plus 300 MHz and Bruker ARX 500 NMR spectrometer. All chemical shifts of $^1$H were referenced to tetramethylsilane (TMS, δ=0.00 ppm) or CDCl$_3$ (δ=7.26 ppm), and chemical shifts of $^{13}$C NMR were referenced to CDCl$_3$ (δ=77.00 ppm). Mass spectra were recorded on a Bruker APEX IV mass spectrometer. Elemental analysis was performed by using the Flash EA1112 analyzer.

The synthetic route of the spiropyrane compound of Formula V-1 is as follows:

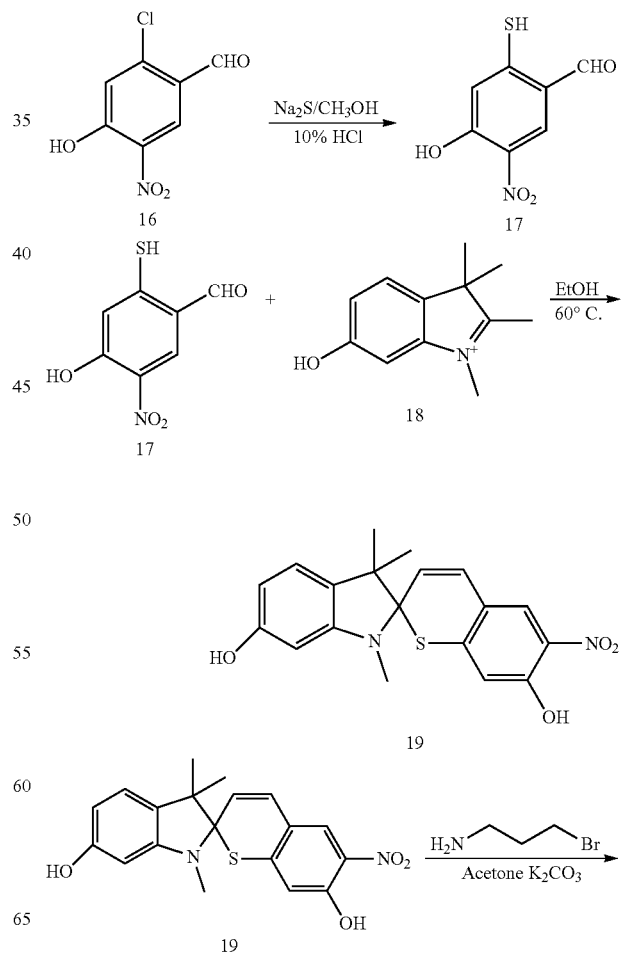

-continued

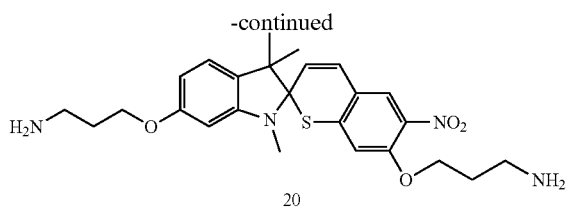

Compound 16 (2.01 g, 10 mmol) was dissolved in 15 mL methanol, heated to 50° C., and Na$_2$S.9H$_2$O (2.4 g 10 mmol) was dissolved in 10 mL methanol. The solution was cooled to 0° C., and pH of which was adjusted to 1 with 10% HCl solution and then filtered to afford compound 17 as a white solid (1.39 g, 70%).

$^1$H NMR (400 MHz, CDCl$_3$, 298 K) 610.36 (s, 1H), δ 8.10 (S, 1H), δ 7.08 (S, 1H), δ 5.36 (s, 1H), δ 3.42 (s, 1H). $^{13}$C NMR (100 MHz, CDCl$_3$, 298 K) δ 189.9, 159.3, 136.5, 134.0, 125.3, 124.3, 117.1. HRMS (TOF-ESI$^+$) (m/z): C$_7$H$_5$NO$_4$S, calcd for 199.99[M$^+$H$^+$], found 200.00.

Compound 17 (2.39 g, 12 mmol) and compound 18 (1.9 g, 10 mmol) were dissolved in 30 mL ethanol, refluxed for 5 h. The reaction system was cooled to room temperature, and filtered to obtain residue. The residue was then re-dissolved with DCM and purified by column chromatography, to afford compound 19 (2.89 g, 78%).

$^1$H NMR (400 MHz, CDCl$_3$, 298 K) δ 7.65 (s, 1H), δ 7.10 (d, J=7.26 Hz, 1H), δ 6.83 (S, 1H), δ 6.66 (d, J=10.5 Hz, 1H), δ 6.19 (s, 1H), δ 6.00 (s, 2H), δ 5.35 (s, 2H), δ 2.93 (s, 3H), δ 1.10 (s, 6H). $^{13}$C NMR (100 MHz, CDCl$_3$, 298 K) δ 152.5, 151.2, 146.2, 133.33, 127.3, 127.0, 126.5, 121.6, 121.3, 121.1, 119.2, 118.9, 113.9, 109.5, 94.3, 52.8, 34.0, 21.1. HRMS (TOF-ESI$^+$) (m/z): C$_{19}$H$_{18}$N$_2$O$_4$S, calcd for 371.10[M+H$^+$], found 371.12.

Compound 19 (0.5 g, 1.35 mmol), 3-bromopropylamine (1.9 g, 13.87 mmol), potassium carbonate was mixed in acetone. Then acetone was removed by vacuum, the product was extracted with dichloromethane, washed with brine for three times, and then purified by column chromatography to afford compound 20 (compound of Formula V-1) as a brown solid, 0.654 g (100%).

$^1$H NMR (400 MHz, CDCl$_3$, 298 K) δ 7.75 (s, 1H), δ 7.14 (d, J=7.26 Hz, 1H), δ 6.85 (S, 1H), δ 6.66 (d, J=10.5 Hz, 1H), δ 6.24 (m, 2H), δ 6.00 (d, J=10.5 Hz, 1H), δ 5.11 (s, 4H), δ 4.06 (d, J=7.1 Hz, 4H), δ 2.90 (s, 3H), δ 2.56 (d, J=7.0 Hz, 4H), S 2.00 (m, 4H), δ 1.16 (s, 6H). $^{13}$C NMR (100 MHz, CDCl$_3$, 298 K) δ 158.1, 150.6, 150.3, 145.4, 135.8, 127.0, 125.5, 121.1, 120.8, 120.5, 117.9, 112.4, 103.5, 95.6, 94.3, 72.5, 71.5, 52.8, 49.8, 34.0, 31.0, 21.1. HRMS (TOF-ESI$^+$) (m/z): C$_{25}$H$_{32}$N$_4$O$_4$S, calcd for 485.21[M$^+$H$^+$], found 485.19.

Example 10: Preparation of the Spiropyrane-Graphene Molecular Junction Device of Formula V-1

A two-dimensional monolayer graphene having a nanogap array was fabricated by using a dash-line lithographic (DLL) method as described detailedly in the afore-mentioned literatures. For molecular coupling, the spiropyrane compound of Formula V-1 was first dissolved in pyridine at a concentration of about 10$^{-4}$ M. The solution was then radiated with visible light (>520 nm) such that the spiropyrane compound of Formula V-1 was in closed configuration. Finally, graphene and carbodiimide dehydrating agent-activator 1-ethyl-3-(3-dimethylaminopropyl)carbodiimide hydrochloride (EDCI) were added to the solution of the spiropyrane compound of Formula V-1, and and reconnected for two days in dark. Thereafter, the reconnected graphene was taken out from the solution, washed with copious acetone and ultrapure water, and dried in N$_2$ gas stream.

Characterization of the Spiropyrane-Graphene Molecular Junction Device Prepared in Example 10

(1) Characterization of Switching Characteristics of Light-Controlled Molecular Junction Devices The characterization of the molecular junction devices at room temperature was performed by using an Agilent 4155C semiconductor characterization system and a Karl Suss (PM5) manual probe station in ambient atmosphere. Light radiation was performed with a hand-held UV lamp (WFH-2048, Shanghai Tanghui Electronics Co., Ltd.) (~100 μW/cm$^2$, λ=365 nm) and with a monochromatic visible light (~240 μW/cm$^2$, λ=540 nm). The monochromatic light was generated by a grating monochromator with a 150 W halogen incandescent lamp (TLS 1509-150A, Zolix instruments Ltd., Beijing). To avoid heating during radiation, visible light was focused and guided by a long optical fiber up to about 2 cm from the molecular junction device. For typical real-time measurements of switching characteristics of light-controlled molecular junction devices at room temperature, ultraviolet and visible lights were toggled back and forth at standard atmospheric conditions. For the stability measurements, the molecular junction devices were kept in a dark metal box under standard atmospheric conditions for more than a year. Then, the molecular junction devices were taken out and subjected to similar measurements.

The spiropyrane compound turns to a closed configuration under visible light, the $I_D$ changes little with $V_D$, which is equivalent to the molecular junction device exhibiting a low conductive state. Under ultraviolet light, the spiropyrane compound turns to a open configuration, the $I_D$ changes largely with of $V_D$, which is equivalent to the molecular junction device exhibiting a high conductive state. The switching of the whole molecular junction device is reversible and reproducible.

Based on this, a reversible light-controlled molecular switch device was prepared in an example of the present invention, comprising at least the spiropyrane-graphene molecular junction device prepared in Example 10. The light-controlled molecular switch device exhibits a high conductive state under ultraviolet light, equivalent to switch on; and the light-controlled molecular switch device exhibits a low conductive state under visible light, equivalent to switch off. Accordingly, reversible switching is achieved. Moreover, the reversible light-controlled molecular switch device may further comprise a visible light generating means and an ultraviolet light generating means for radiating the reversible light-controlled molecular switch device with visible light or ultraviolet light. The visible light generating means and the ultraviolet light generating means can be obtained by a skilled person in the art in accordance with the invention herein, without creative work, and are not limited herein. For example, the visible light generating means and the ultraviolet light generating means can utilize a 50 W xenon light source PLS-SXE300/300 UV light source (Beijing Bofeilai Technology Co., Ltd.) and then provide ultraviolet light at 365 nm and visible light at 540 nm using a monochromator.

(2) Characterization of temperature-dependent I-V characteristics of the spiropyrane-graphene molecular junction devices (the spiropyrane compound turns to an open configuration under UV radiation) was carried out by using an Agilent 4155C semiconductor characterization system and ST-500-probe station (Janis Research Company) with liquid nitrogen and liquid helium cooling. Real-time recording of random switching was performed at a low temperature and in vacuum (at a pressure of less than $1*10^{-4}$ Pa).

The following conclusions can be drawn from the above results:

(5-1) At the temperature of 100 K to 300 K, the molecular junction device exhibits the characteristics of random switching between a high conductive state and a low conductive state under a source-drain voltage ranging from 0.2 V to 1.5 V or ranging from −0.2 V to −1.5 V.

(5-2) When the temperature is below 100 K, the molecular junction device exhibits a continuously low conductive state; and when the temperature is above 300 K, the molecular junction device exhibits a continuously high conductive state.

(5-3) At the temperature of 100 K to 300 K, the molecular junction device exhibits a low conductive state when the source-drain voltage is between −0.2 V and 0.2 V; and the molecular junction device exhibits a continuously high conductivity state when the source-drain voltage is greater than 1.5 V or less than −1.5 V.

Based on the conclusion (5-1), an example of the present invention provides a reversible electrically-controlled molecular switch device, comprising the spiropyrane-graphene molecular junction device provided by example 10 of the present invention. The spiropyrane compound turns to an open configuration, i.e., the structure represented by Formula V-2 under ultraviolet light. When a voltage of 0.2 V to 1.5 V or −0.2 V to −1.5 V is supplied across the molecular junction device, the electrically-controlled molecular switch device exhibits random switching between a high conductive state and a low conductive state at a temperature of 100 K to 300 K. The switch device has the characteristics of random switching of conductive states, and thus can be used for performing logic operations and the like. In addition, the electrically-controlled molecular switch device may further comprise a voltage generating means connected to the molecular junction device for supplying a voltage ranging from 0.2 V to 1.5 V or ranging from −0.2 V to −1.5 V across the molecular junction device.

Based on the conclusion (5-2), an example of the present invention provides a reversible temperature-controlled molecular switch device, comprising the spiropyrane-graphene molecular junction device provided by example 10 of the present invention. The spiropyrane compound turns to an open configuration under ultraviolet light, i.e., the structure represented by Formula V-2. The temperature-controlled molecular switch device exhibits a low conductive state at a temperature below 100 K; and the temperature-controlled molecular switch device exhibits a high conductive state at a temperature above 300 K. The temperature-controlled molecular switch device can exhibit different switching characteristics at different temperatures. When the temperature is below 300 K, the temperature-controlled molecular switch device exhibits a low conductive state, and only has a very small $I_D$, equivalent to switch off; and when the temperature is above 300 K, the temperature-controlled molecular switch device exhibits a high conductive state, and has a large $I_D$, equivalent to switch on. Thus, the temperature-controlled molecular switch device can be used as a temperature sensor or a temperature sensitive switch. The temperature-controlled molecular switch device can also comprise a temperature control means for providing a temperature below 100 K or a temperature above 300 K to the temperature-controlled molecular switch device. Thus, the regulation of the temperature-controlled molecular switch device can be achieved by adjusting the temperature.

Based on the conclusion (5-3), an example of the present invention provides another reversible electrically-controlled molecular switch device, comprising the spiropyrane-graphene molecular junction device provided by example 10 of the present invention. The spiropyrane compound turns to an open configuration, i.e., the structure represented by Formula V-2 under ultraviolet light. At a temperature of 100 K to 300 K, the electrically controlled molecular switch device exhibits a low conductive state when a voltage of −0.2 V to 0.2 V is supplied across the molecular junction device; and the device exhibits a high conductive state when a voltage of greater than 1.5 V or less than −1.5 V is supplied across the molecular junction device. That is to say, when the applied bias voltage is a low threshold voltage (−0.2 V to 0.2 V), the electrically-controlled molecular switch device is switched-off (low conductive); and when the bias voltage is at a high threshold voltage (greater than 1.5 V or less than −1.5 V), the electrically-controlled molecular switch device is switched-on (high conductive). Further, the electrically-controlled molecular switch device may further comprise a voltage generating means connected to the molecular junction device, for supplying a voltage of −0.2 V to 0.2 V, or a voltage of greater than 1.5 V or less than −1.5 V across the molecular junction device.

It should be noted that the voltage generating means connected to the molecular junction devices in the above switch devices, can be implemented by using the prior art in this field, for example, a lock-in amplifier, preferably an HF2LI lock-in amplifier (Zurich Instruments Ltd.) can be used as the voltage generating means of the switch device mentioned above. The voltage generating means are not limited in the present invention. Those skilled in the art can obtain the voltage generating means according to the description herein and connect it to the molecular junction device, without any creative work.

(3) Characterization of Switching Characteristics of the Electrically-Controlled Molecular Junction Devices (Containing the Spiropyrane Compound of Formula V-1)

The same characterization method was performed as that of the diarylethene compound molecular junction device of Formula II-1, and the same conclusion as the diarylethene compound molecular junction device of Formula II-1 was obtained. The invention will not be described herein, and the above description may be referred to.

Flexible Non-Volatile Organic Memory Transistor Devices Prepared from the Spiropyrane Compound of Formula V-1 and Characterization Thereof The flexible substrate and the hafnium oxide dielectric layer of the organic memory tube were prepared by using the method described in detail in the aforementioned literatures. For molecule assembly, after the preparation of the hafnium oxide dielectric layer, the $HfO_2$ surface was activated with an oxygen plasma etcher (RIE) at a power of 30 W for 3 minutes to produce —OH for the self-assembly reaction. The activated substrate was immersed in a THF/ethanol mixed solution containing the spiropyrane compound (concentration: 0.1 mM, THF/ethanol=1:1 (V/V), THF and ethanol were strictly dehydrated) in dark for 24 hours for self-assembly within a glove box under argon. The substrate was taken out, the surface of which was washed with ethanol for three times until no visible particulate impurities was observed. The substrate was annealed at 120° C. on the heating stage for 3 minutes to make the amino anchoring group and the cerium oxide substrate link more firmly. Then, a 30 nm thick of pentacene was vacuum evaporated on the above-mentioned substrate in which the spiropyrane monomolecular film was assembled within a thermal evaporater. Finally, a metal electrode was evaporated at a predetermined position of the substrate by thermal evaporation.

Characterization of organic memory transistor devices was performed in ambient atmosphere using an Agilent 4155C semiconductor characterization system and a Karl Suss (PM5) manual probe station at room temperature.

The obtained flexible non-volatile organic memory transistor device uses light at 633 nm as a means for writing information. The light radiation conditions in the specific experiment are as follows: the ultraviolet light source is a hand-held UV lamp (energy density I=100 W cm$^{-2}$, wavelength=365 nm); the white light source is a halogen incandescent lamp (energy density I=30 mW cm$^{-2}$, wavelength >420 nm); the global light source at 633 nm is a 150 W halogen incandescent light source with a 633 nm cut-off light filter.

The characterization of processes of presetting, writing, erasing for the flexible non-volatile organic memory transistor device were as follows. Firstly, ultraviolet light (365 nm) was applied to "preset" the device, so as to allow the device to work as a memory device. After the device was preset, visible light radiation at 633 nm can be used to "write" the information thereto. When the device was radiated with visible light at 633 nm, the source-drain current increases linearly and reaches a high conductive state; and after the radiation was stopped, the high conductive state was continuously maintained. This result demonstrates the non-volatile storage performance of a photoactive hybrid dielectric layer. Visible light radiation (≥520 nm) makes the spiropyrane monomolecular film be switched from On to Off, meanwhile make the device be back to the initial electrical state, and therefore it serves as an "erasing" means for the memory device. At the same time, when a negative gate voltage ($V_G$) was applied to the gate, the erasing of information can also be achieved.

A Photo-Responsive Organic Transistor Device Prepared from the Azobenzene Compound of Formula V-1 and Characterization Thereof The substrate and the gold electrode of the organic field-effect transistor with a bottom gate bottom contact structure were prepared by using the method described in detail in the aforementioned literatures. For molecule assembly, the surface of the prepared gold electrode was washed with ethanol, and then etched by an oxygen plasma etcher (RIE) at a power of 30 W for 5 minutes to clean the organic substances adsorbed thereon. The cleaned substrate containing the patterned gold electrode pair was immersed in an ethanol solution of the spiropyrane compound represented by Formula V-1 (concentration: 10$^{-4}$ mol/L) for 24 hours in dark under the protection of Ar gas. The substrate was taken out, the surface of which was washed with ethanol for three times. The substrate was annealed at 50° C. on the heating stage for 10 minutes. Finally, a 30 nm thick of pentacene was vacuum evaporated on the above-mentioned substrate in which the spiropyrane monomolecular film was assembled within a thermal evaporater.

The characterization of the photo-responsive organic field-effect transistor was performed at room temperature in ambient atmosphere using an Agilent 4155C semiconductor characterization system and a Karl Suss (PM5) manual probe station. Light radiation was performed with a hand-held UV lamp (WFH-2048, Shanghai Tanghui Electronics Co., Ltd.) (~100 μW/cm$^2$, λ=365 nm) and with a monochromatic visible light (~240 μW/cm$^2$, λ=540 nm). Monochromatic light was generated by a grating monochromator with a 150 W halogen incandescent lamp (TLS 1509-150A, Zolix instruments Ltd., Beijing). In order to avoid heating during radiation, visible light was focused and guided by a long optical fiber up to about 2 cm from the molecular junction device. For typical real-time measurements of switching characteristics of the photo-responsive organic field-effect transistor at room temperature, ultraviolet and visible lights were toggled back and forth at standard atmospheric conditions.

The results show that the spiropyrane compound becomes an open configuration under ultraviolet light, and conductance of the device is approximately doubled. Under visible light, the spiropyrane compound becomes a closed configuration and the conductance of the device is reduced to approximately ⅓ of the conductance of the high conductive state.

The above are only the preferred examples of the present invention and they are not intended to limit the scope of the present invention. Any modifications, equivalent substitutions, improvements, and the like obtained within the spirit and scope of the present invention are included in the scope of the present invention.

REFERENCES

H. Chen, N. Cheng, W. Ma, M. Li, S. Hu, L. Gu, S. Meng, X. Guo, Design of a Photoactive Hybrid Bilayer Dielectric for Flexible Nonvolatile Organic Memory Transistors. ACS Nano 10, 436-445 (2016). doi: 10.1021/acsnano.5b05313

H. Zhang, H. Chen, W. Ma, J. Hui, S. Meng, W. Xu, D. Zhu, X. Guo, Photocontrol of charge injection/extraction at electrode/semiconductor interfaces for high-photoresponsivity organic transistors J. Mater. Chem. C, (2016). doi: 10.1039/c6tc00387g F. Meng, Y. Hervault, L. Norel, K. Costuas, C. V. Dyck, V. Geskin, J. Cornil, H. H. Hng, S. Rigaut, X. Chen, Photomodulable molecular transport junctions based on organometallic molecular wires. Chem. Sci. 3, 3113-3118 (2012). doi: 10.1039/C2SC20323E L. N. Lucas, J. van Esch, R. M. Kellogg, B. L. Feringa, A new class of photochromic 1, 2-diarylethenes; synthesis and switching properties of bis (3-thienyl) cyclopentenes. Chem. Commun. 2313-2314 (1998). doi: 10.1039/A806998K Y. Chen, B. Zhu, Y. Han, Z. Bo, Self-assembly of cationic pyrene nanotubes. J. Mater. Chem. 22, 4927-4931 (2012). doi: 10.1039/C2JM15997J C. Jia, J. Wang, C. Yao, Y. Cao, Y. Zhong, Z. Liu, X. Guo, Conductance switching and mechanisms in single-molecule junctions. Angew. Chem. Int. Ed. 52, 8666-8670 (2013). doi: 10.1002/anie.201304301

Y. Cao, S. H. Dong, S. Liu, L. He, L. Gan, X. M. Yu, M. L. Steigerwald, X. S. Wu, Z. F. Liu, X. F. Guo, Building high-throughput molecular junctions using indented graphene point contacts. Angew. Chem. Int. Ed. 51, 12228-12232 (2012). doi: 10.1002/anie.201205607

What is claimed is:
1. A diarylethene-graphene molecular junction device, wherein the molecular junction device comprises a diarylethene compound linked to a gap of a two-dimensional monolayer graphene having a nanogap array via an amide covalent bond, wherein the diarylethene compound has any one of the following formulae:

Formula 1
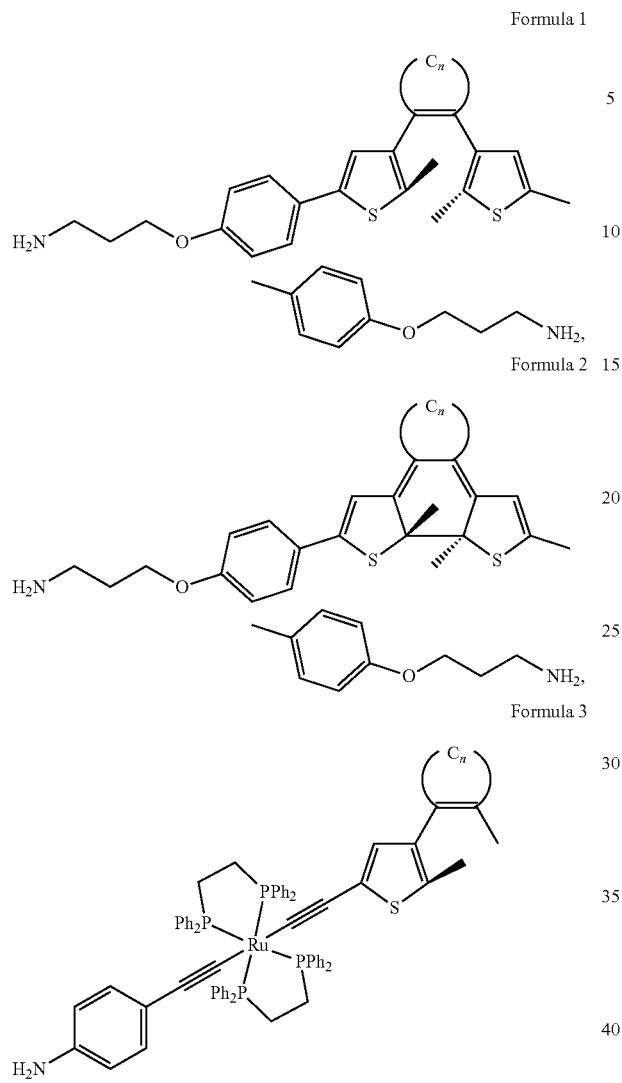
Formula 2
Formula 3
-continued
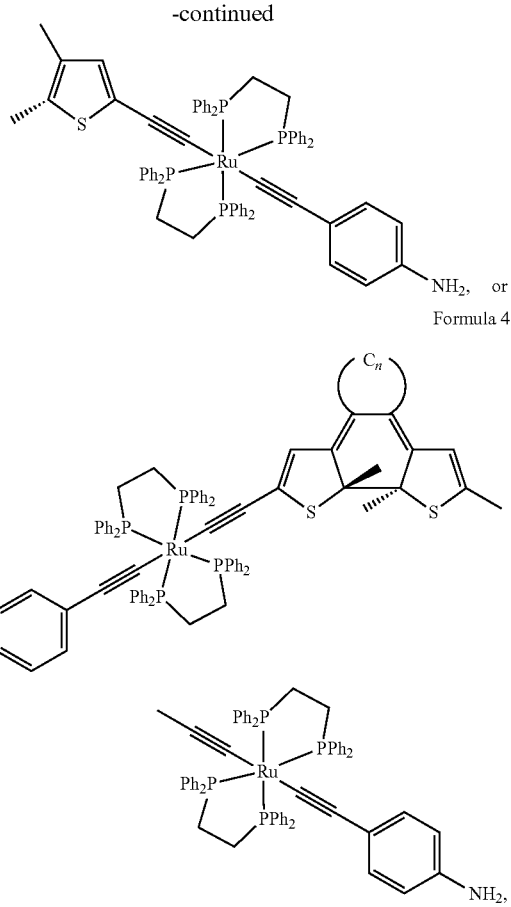
Formula 4
wherein $C_n$ represents a linear alkylene group having 3-4 carbon atoms, and H of the alkylene group may be substituted with at least one selected from F, Cl, Br or I.
2. The diarylethene-graphene molecular junction device of claim 1, wherein the diarylethene compound is any one of the following formulae:
Formula I-1
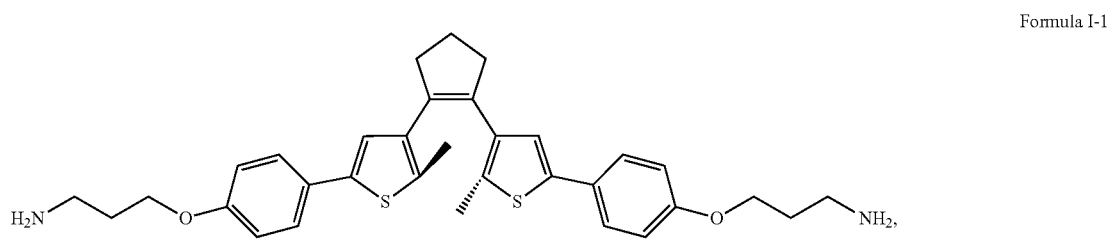
Formula I-2
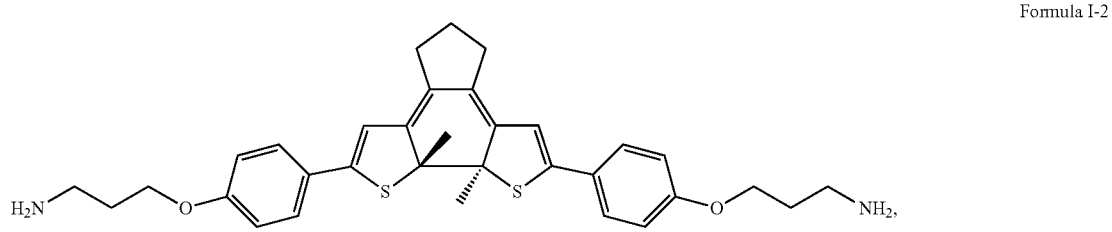

Formula II-1

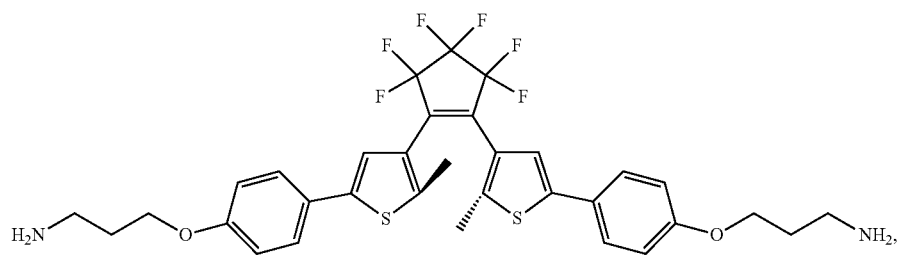

Formula II-2

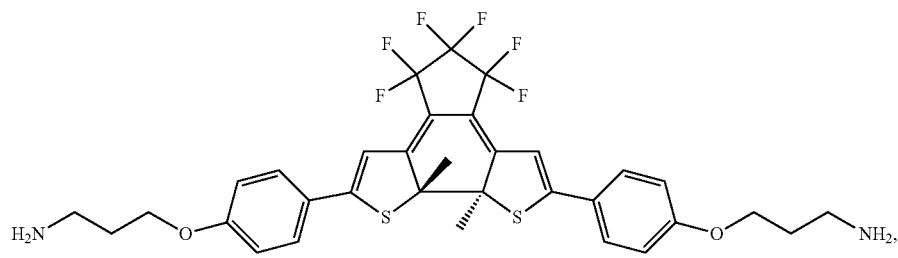

Formula III-1

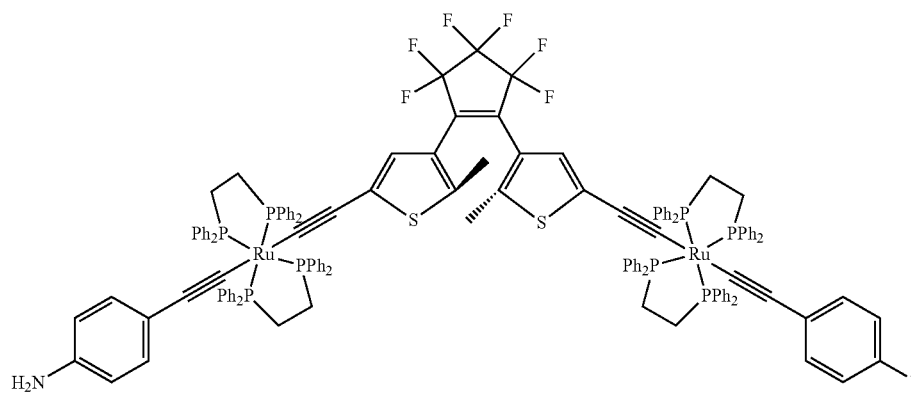

or

Formula III-2

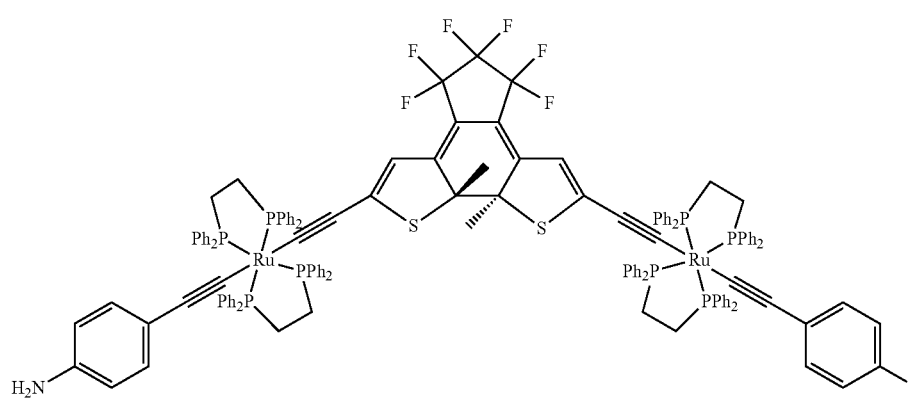

3. A reversible molecular switch device or a transistor device comprising the diarylethene-graphene molecular junction device of claim 1, wherein:
(1) the reversible molecular switch device is a reversible light-controlled molecular switch device, wherein the reversible light-controlled molecular switch device exhibits a high conductive state under ultraviolet light; and the reversible light-controlled molecular switch device exhibits a low conductive state under visible light;
(2) the reversible molecular switch device is a reversible electrically-controlled molecular switch device comprising a voltage generating means connected to the molecular junction device; wherein the voltage generating means is used to supply:
(a) a voltage of 0.9 V to 1.5 V or a voltage of −0.9 V to −1.5 V; or
(b) a voltage of −0.9 V to 0.9 V, or a voltage of greater than 1.5 V or less than −1.5 V, across the molecular junction device;
provided that the voltage generating means supplies the voltage of 0.9 V to 1.5 V or the voltage of −0.9 V to −1.5 V across the molecular junction device, the reversible electrically-controlled molecular switch device exhibits random switching between a high conductive state and a low conductive state at a temperature of 100

K to 300 K when the electrically-controlled molecular switch device comprises a diarylethene compound of any of Formulae 1-4; and provided that the voltage generating means supplies a voltage of −0.9 V to 0.9 V, or a voltage greater than 1.5 V or less than −1.5 V across both ends of the molecular junction device, the reversible electrically-controlled molecular switch device exhibits a low conductive state in a voltage range of −0.9 V to 0.9 V and a high conductive state in a voltage of greater than 1.5 V or less than −1.5 V at a temperature of 100 K to 300 K when the reversible electrically-controlled molecular switch device comprises a diarylethene compound of any of Formulae 1-4; or (3) the reversible molecular switch device is a reversible temperature-controlled molecular switch device; wherein when the reversible temperature-controlled molecular switch device comprises a diarylethene compound of any of Formulae 1-4, the reversible temperature-controlled molecular switch device exhibits a low conductive state at a temperature below 100 K, and a high conductive state at a temperature above 300 K; or (4) the transistor device comprises the diarylethene-graphene molecular junction device assembled between a dielectric layer and a semiconductor layer of an organic field-effect transistor, or between an electrode and a semiconductor layer of an organic field-effect transistor.

4. The reversible molecular switch device or a transistor device of claim 3, wherein the reversible light-controlled molecular switch device further includes a visible light generating means and an ultraviolet light generating means, for respectively radiating visible light or ultraviolet light to the reversible light-controlled molecular switch device.

5. The reversible molecular switch device or a transistor device of claim 3, wherein the diarylethene compound in the reversible electrically-controlled molecular switch device is one of the following formulae:

Formula I-1

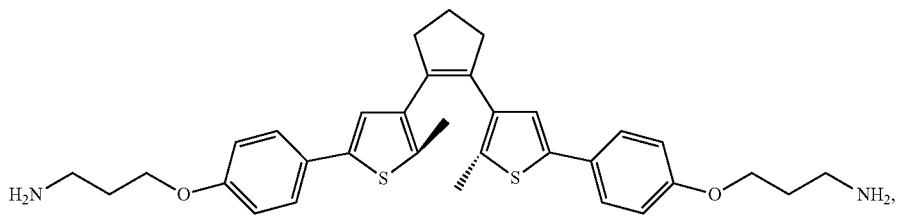

Formula I-2

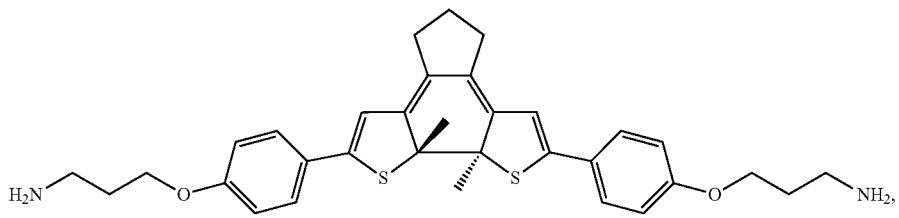

Formula II-1

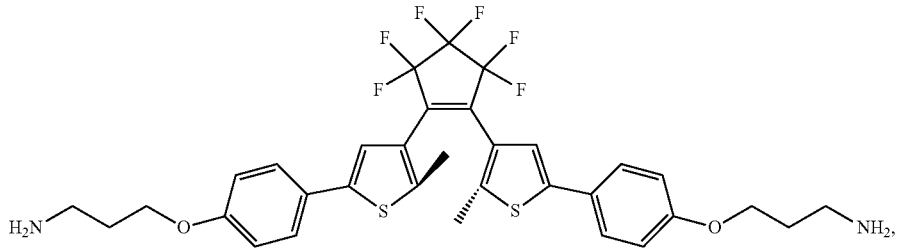

Formula II-2

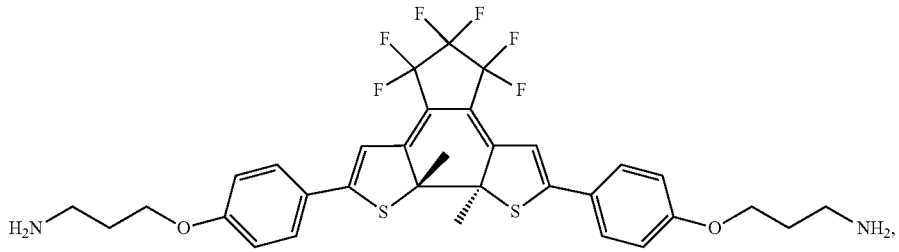

Formula III-1
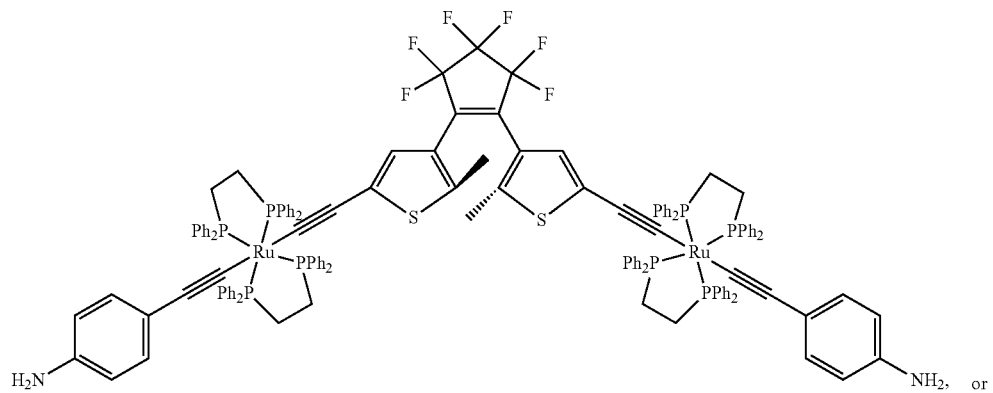
or
Formula III-2
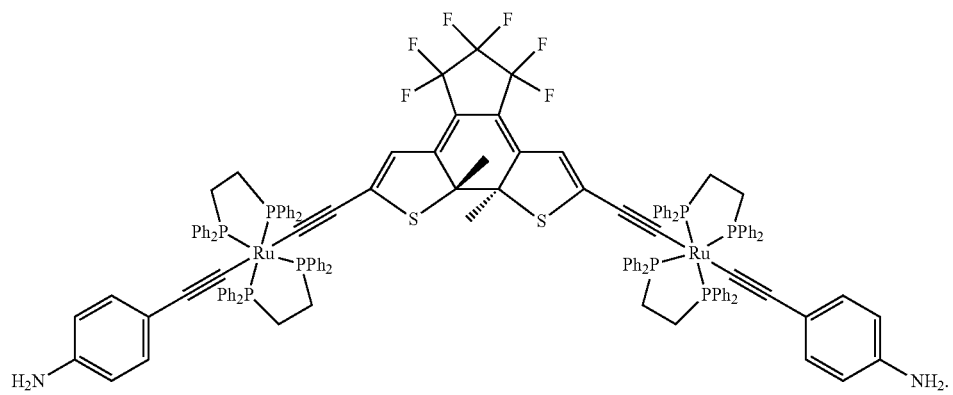
6. The reversible molecular switch device or a transistor device of claim 3, wherein the reversible temperature-controlled molecular switch device comprises the diarylethene compound of:
Formula I-1
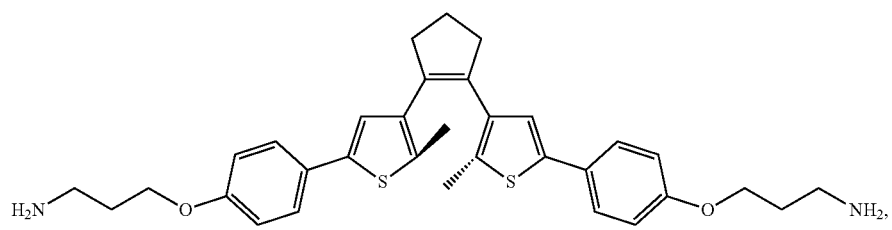
Formula I-2
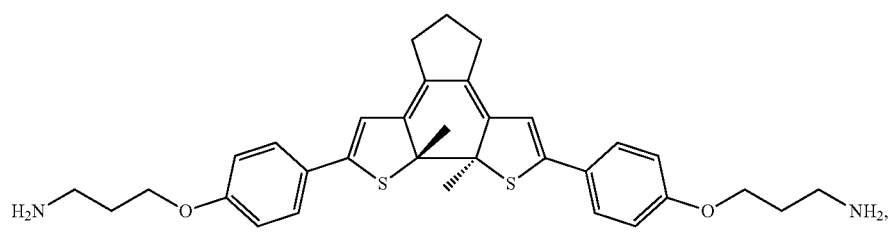

Formula II-1

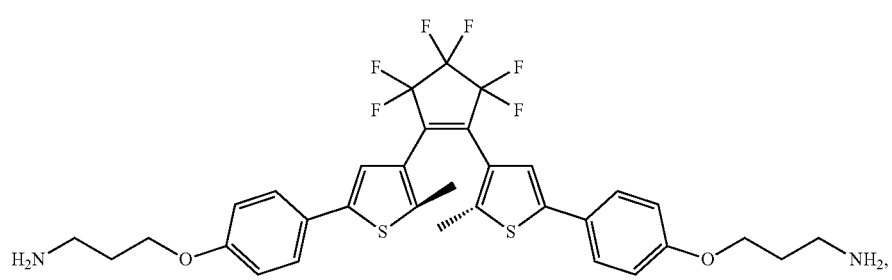

Formula II-2

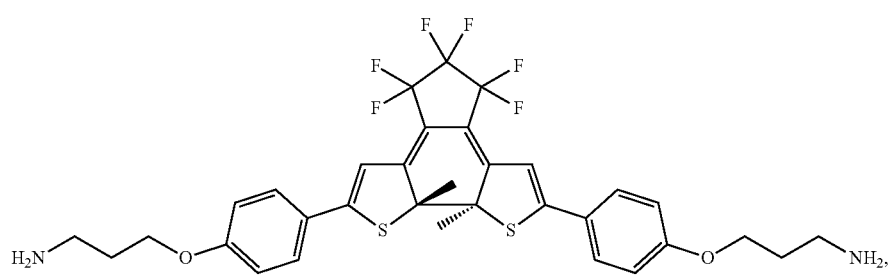

Formula III-1

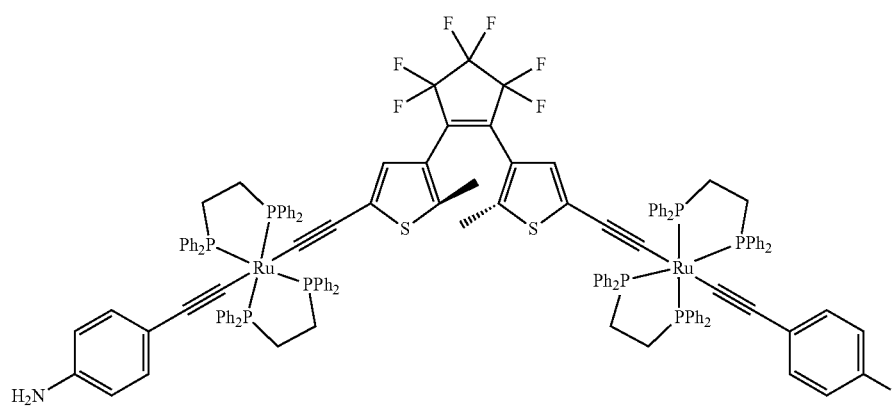

or

Formula III-2

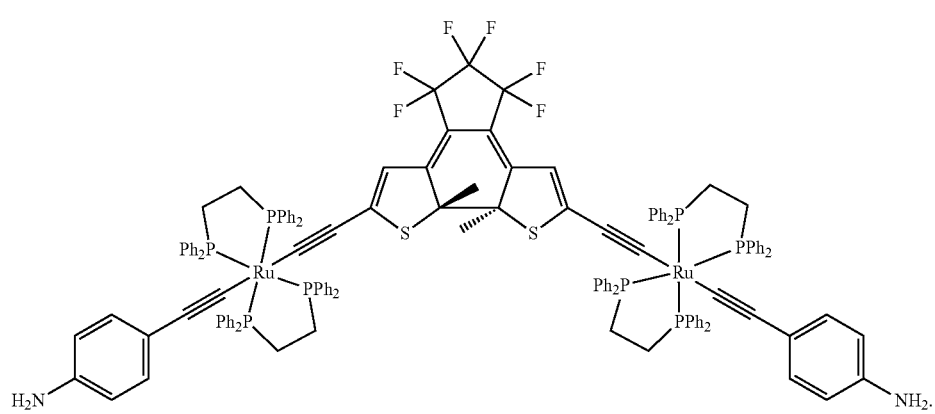

7. The reversible molecular switch device or a transistor device of claim 5, wherein:
(2) the reversible molecular switch device is the reversible electrically-controlled molecular switch device;
provided that the voltage generating means supplies the voltage of 0.9 V to 1.5 V or the voltage of −0.9 V to −1.5 V across the molecular junction device, the reversible electrically-controlled molecular switch device exhibits random switching between a high conductive state and a low conductive state at a temperature of 160 K to 220 K when the reversible electrically-controlled molecular switch device comprises the diarylethene compound of Formula I-1 or Formula I-2; and provided that the voltage generating means supplies a voltage of −0.9 V to 0.9 V, or a voltage greater than 1.5 V or less than −1.5 V across both ends of the molecular junction device, the reversible electrically-controlled molecular switch device exhibits a low conductive state in a voltage range of −0.9 V to 0.9 V and a high conductive state in a voltage of greater than 1.5 V or less than −1.5 V at a temperature of 160 to 220 K when the reversible electrically-controlled molecular switch device comprises the diarylethene compound of Formula I-1 or Formula I-2.

8. A reversible temperature-controlled molecular switch device comprising the diarylethene-graphene molecular junction device of claim 2, wherein when the reversible temperature-controlled molecular switch device comprises the diarylethene compound of Formula I-1 or I-2, the reversible temperature-controlled molecular switch device exhibits a low conductive state at a temperature below 160 K, and exhibits a high conductive state at a temperature above 220 K.

* * * * *